(12) United States Patent
Yoon et al.

(10) Patent No.: US 11,596,659 B2
(45) Date of Patent: Mar. 7, 2023

(54) **COMPOSITIONS AND METHODS FOR INHIBITING THE PROLIFERATION OF PATHOGENIC *ESCHERICHIA COLI***

(71) Applicant: iNtRON Biotechnology, Inc., Seongnam-si (KR)

(72) Inventors: Seong Jun Yoon, Seoul (KR); Jee Soo Son, Seoul (KR); In Hwang Kim, Gyeonggi-do (KR); Hyoung Rok Paik, Incheon (KR); Hyun Joo Im, Gyeonggi-do (KR); Hyun Jin Yu, Incheon (KR); Cheol Ahn, Gyeonggi-do (KR); Tae Yeol Kim, Gyeonggi-do (KR); Soo Youn Jun, Seoul (KR); Sang Hyeon Kang, Seoul (KR)

(73) Assignee: iNtRON Biotechnology, Inc., Seongnam-si (KR)

( * ) Notice: Subject to any disclaimer, the term of this patent is extended or adjusted under 35 U.S.C. 154(b) by 304 days.

(21) Appl. No.: 15/930,394

(22) Filed: May 12, 2020

(65) Prior Publication Data

US 2021/0353695 A1 Nov. 18, 2021

(51) Int. Cl.
*A61K 35/76* (2015.01)
*A61K 45/06* (2006.01)
*A61P 31/04* (2006.01)

(52) U.S. Cl.
CPC .............. *A61K 35/76* (2013.01); *A61P 31/04* (2018.01)

(58) Field of Classification Search
None
See application file for complete search history.

(56) References Cited

U.S. PATENT DOCUMENTS

2017/0035817 A1* 2/2017 Shin ................ A61P 31/04

FOREIGN PATENT DOCUMENTS

WO 2019/051603 * 3/2019

OTHER PUBLICATIONS

Jurczak-Kurek et al. (Scientific Reports, 2016, vol. 6(34338), pp. 1-17).*
Wang et al. (International Journal of Molecular Medicine, 2006, vol. 17(2), pp. 347-355).*
https://www.sciencedirect.com/topics/agricultural-and-biological-sciences/myoviridae (Myoviridae—an overview Science direct topics 2012).*

\* cited by examiner

*Primary Examiner* — Jennifer E Graser
(74) *Attorney, Agent, or Firm* — SIMI Law Group, P.C.

(57) ABSTRACT

A composition for preventing or treating an infection or disease caused by a pathogenic *Escherichia coli* includes a Myoviridae bacteriophage Esc-COP-18 having an ability to lyse the pathogenic *Escherichia coli* and a pharmaceutically acceptable carrier. A method for preventing or treating an infection or disease caused by a pathogenic *Escherichia coli* includes administering to a subject a Myoviridae bacteriophage and lysing the pathogenic *Escherichia coli* by the Myoviridae bacteriophage.

8 Claims, 4 Drawing Sheets

Specification includes a Sequence Listing.

COMPOSITIONS AND METHODS FOR INHIBITING THE PROLIFERATION OF PATHOGENIC *ESCHERICHIA COLI*

BACKGROUND OF THE INVENTION

Field of the Invention

The present invention relates to compositions and methods for inhibiting the proliferation of pathogenic *Escherichia coli*, more specifically, a composition containing a Myoviridae bacteriophage and a method of using the same.

Discussion of the Related Art

*Escherichia coli* is a Gram-negative, facultative anaerobic, rod-shaped, coliform bacterium of the genus *Escherichia*. It is serologically subdivided according to whether it contains a somatic (O), flagellar (H) or capsular (K) antigen, and these antigens are known to be associated with the pathogenicity of *Escherichia coli*. Pathogenic *Escherichia coli* refers to *Escherichia coli* that has acquired a small number of the virulence factors capable of being expressed in *Escherichia coli*, and, depending on the onset characteristics and the kind of toxin, there are five types of pathogenic *Escherichia coli*, namely enterohemorrhagic *Escherichia coli*, enterotoxigenic *Escherichia coli*, enteroinvasive *Escherichia coli*, enteropathogenic *Escherichia coli*, and enteroaggregative *Escherichia coli*.

Pathogenic *Escherichia coli* causes various diseases, such as food poisoning, acute pancreatitis, urinary tract infection, septicemia and cancer. Among pathogenic *Escherichia coli*-associated cancer, colorectal cancer is one of the most common cancers, accounting for approximately 10% of all cancer cases and approximately 8% of all cancer deaths. Also, colorectal cancer is very common globally and develops through accumulation of colonic epithelial cell mutations that promote transition of normal mucosa to adenocarcinoma. As one of major causes leading to colorectal cancer occurrence, colonic polyp refers to a condition in which the colonic mucosa grows abnormally and becomes a wart-shaped bump that protrudes into the intestine. It is often divided into neoplastic polyps that are likely to develop into cancer and non-neoplastic polyps that are unlikely to develop into cancers. Among various types of polyp, adenomatous polyps are more likely to develop cancer over time. Although diarrhea caused by pathogenic *Escherichia coli* is a notable disease, colonization of some pathogenic *Escherichia coli* is related to promotion of colorectal cancer development by promotion of the formation of adenomatous polyps.

Generally, vaccines and antibiotics are used for the prevention and treatment of infectious diseases of pathogenic *Escherichia coli*. Here, the effectiveness of antibiotics has been continuously decreasing due to the increase of antibiotic-resistant pathogenic *Escherichia coli*, and the development of effective methods other than currently prescribed antibiotics is required.

Recently, the use of bacteriophages as a countermeasure against bacterial infectious diseases has attracted considerable attention. Bacteriophages are very small microorganisms infecting bacteria, and are usually simply called "phages." Once a bacteriophage infects a bacterial cell, the bacteriophage is proliferated inside the bacterial cell. After proliferation, the progeny of the bacteriophage destroys the bacterial cell wall and escapes from the host bacteria, suggesting that the bacteriophage has the ability to kill bacteria. The manner in which the bacteriophage infects bacteria is characterized by the very high specificity thereof, and thus the number of types of bacteriophages infecting a specific bacterium is limited. That is, a certain bacteriophage can infect only a specific bacterium, suggesting that a certain bacteriophage can kill only a specific bacterium and cannot harm other bacteria. Due to this bacteria specificity of bacteriophages, the bacteriophage confers antibacterial effects only upon target bacteria, but does not affect commensal bacteria in animals including human being. Conventional antibiotics, which have been widely used for bacterial treatment, incidentally influence many kinds of bacteria. This causes problems such as the disturbance of normal microflora. On the other hand, the use of bacteriophages does not disturb normal microflora, because the target bacterium is selectively killed. Hence, the bacteriophage may be utilized safely, which thus greatly lessens the probability of adverse actions in use compared to any other antibiotics.

Owing to the unique ability of bacteriophages to kill bacteria, bacteriophages have attracted attention as a potentially effective countermeasure against bacterial infections since their discovery, and there has been a lot of research related thereto.

Bacteriophages tend to be highly specific for bacteria. Because of this specificity, bacteriophages frequently exhibit an antibacterial effect only for certain strains of bacteria, even though the bacteria belong to the same species. In addition, the antibacterial strength of bacteriophages may depend on the type of target bacterial strain. Therefore, it is necessary to collect many kinds of bacteriophages that are useful in order to get effective control of specific bacteria. Hence, in order to develop the effective bacteriophage utilization method in response to pathogenic *Escherichia coli*, many kinds of bacteriophages that exhibit antibacterial action against pathogenic *Escherichia coli* must be acquired. Furthermore, the resulting bacteriophages need to be screened as to whether or not they are superior to others from the aspect of antibacterial strength and spectrum.

SUMMARY OF THE INVENTION

Accordingly, the present invention has been made keeping in mind the problems encountered in the related art and is intended to solve such problems.

In one embodiment, a composition for preventing or treating an infection or disease caused by a pathogenic *Escherichia coli* includes: a Myoviridae bacteriophage having an ability to lyse the pathogenic *Escherichia coli*, and a pharmaceutically acceptable carrier.

In another embodiment, the Myoviridae bacteriophage includes a sequence as set forth in SEQ ID NO: 1.

In another embodiment, the Myoviridae bacteriophage has a concentration of $1 \times 10^1$ pfu/ml to $1 \times 10^{30}$ pfu/ml or $1 \times 10^1$ pfu/g to $1 \times 10^{30}$ pfu/g.

In another embodiment, the Myoviridae bacteriophage has a concentration of $1 \times 10^4$ pfu/ml to $1 \times 10^{15}$ pfu/ml or $1 \times 10^4$ pfu/g to $1 \times 10^{15}$ pfu/g.

In another embodiment, the pharmaceutically acceptable carrier is lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, or mineral oil.

In another embodiment, the composition further includes one or more selected from the group consisting of a lubricant, a wetting agent, a sweetener, a flavor, an emulsifier, a suspending agent, and a preservative.

In another embodiment, the pathogenic *Escherichia coli* is enterohemorrhagic *Escherichia coli*, enterotoxigenic *Escherichia coli*, enteroinvasive *Escherichia coli*, enteropathogenic *Escherichia coli*, enteroaggregative *Escherichia coli*, or carcinogenic *Escherichia coli*.

In another embodiment, the infection or disease is food poisoning, gastroenteritis, diarrhea, urinary tract infections, neonatal meningitis, hemolytic-uremic syndrome, peritonitis, mastitis, septicemia, Gram-negative pneumonia, shigellosis, dysentery, or cancer.

In another embodiment, the composition is a solution, suspension, emulsion in oil, water-soluble medium, extract, powder, granule, tablet, or capsule.

In another embodiment, the composition further includes a second bacteriophage having an ability to lyse a pathogenic *Escherichia coli* or a non-*Escherichia coli* bacterial species.

In another embodiment, the Myoviridae bacteriophage has major structural proteins in the sizes of approximately 37 kDa, 48 kDa, 75 kDa, and 135 kDa.

In another embodiment, the Myoviridae bacteriophage has a latent period of 20-40 minutes and a burst size of 120-220 PFU/infected cell.

In another embodiment, the latent period is 25-35 minutes and the burst size of 145-195 PFU/infected cell.

In one embodiment, a method for preventing or treating an infection or disease caused by a pathogenic *Escherichia coli* includes administering to a subject a Myoviridae bacteriophage; and lysing the pathogenic *Escherichia coli* by the Myoviridae bacteriophage.

In another embodiment, the Myoviridae bacteriophage includes a sequence as set forth in SEQ ID NO: 1.

In another embodiment, the Myoviridae bacteriophage has a concentration of $1\times10^1$ pfu/ml to $1\times10^{30}$ pfu/ml or $1\times10^1$ pfu/g to $1\times10^{30}$ pfu/g.

In another embodiment, the Myoviridae bacteriophage has a concentration of $1\times10^4$ pfu/ml to $1\times10^{15}$ pfu/ml or $1\times10^4$ pfu/g to $1\times10^{15}$ pfu/g.

It is to be understood that both the foregoing general description and the following detailed description are exemplary and explanatory and are intended to provide further explanation of the invention as claimed.

Advantageous Effects of Invention

The compositions and methods for inhibiting the proliferation of pathogenic *Escherichia coli*, of the present application have high specificity against pathogenic *Escherichia coli*, compared with conventional compositions and methods based on antibiotics. The compositions can be used for preventing or treating pathogenic *Escherichia coli* infections without affecting other useful commensal bacteria and have fewer side effects. In general, when antibiotics are used, commensal bacteria are also damaged, thus entailing various side effects owing to the use thereof. Meanwhile, each antibacterial property of the bacteriophages such as antibacterial strength and spectrum (host range) are different in the case of bacteriophages exhibiting antibacterial activity against the same bacterial species and bacteriophages are usually effective only on some bacterial strains within the same bacterial species. Thus, the compositions and methods of the present application provide different effects in its industrial applications.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
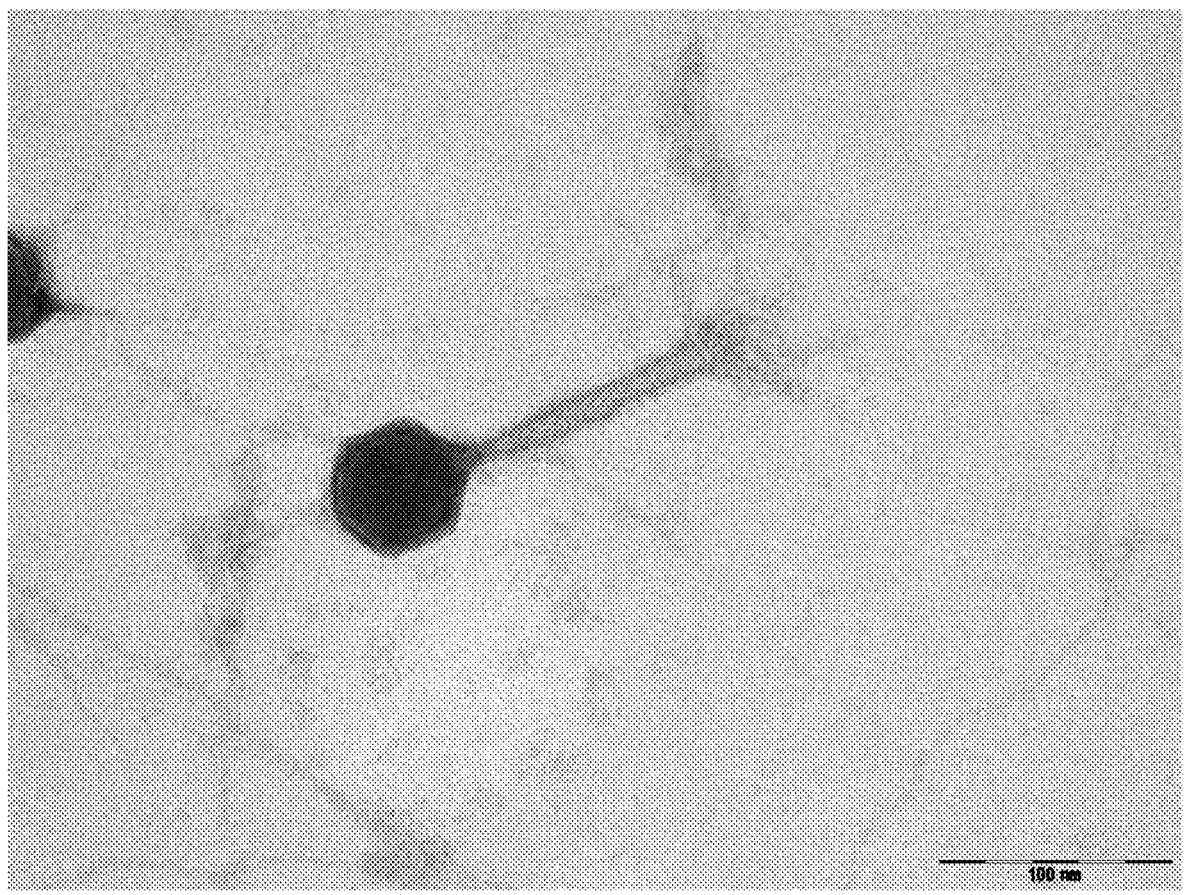
FIG. 1 is an electron micrograph showing the morphology of the bacteriophage Esc-COP-18.

Reference will now be made in detail to embodiments of the present invention, example of which is illustrated in the accompanying drawings.

In accordance with one aspect of the present invention, the present invention provides a Myoviridae bacteriophage, named as Esc-COP-18, which has the ability to specifically kill *Escherichia coli* and has a genome including a sequence as set forth in SEQ ID NO: 1. The present invention also provides a method for preventing and treating infections or diseases caused by pathogenic *Escherichia coli* using a composition including the same as an active ingredient.

The bacteriophage Esc-COP-18 was isolated by the present inventors and then deposited at Korea Collection for Type Cultures, Korea Research Institute of Bioscience and Biotechnology on Nov. 15, 2019 (Accession number: KCTC 14028BP).

The molecular weight of major structural proteins of the bacteriophage Esc-COP-18 is approximately 37 kDa, 48 kDa, 75 kDa, and 135 kDa.

The latent period and burst size of the bacteriophage Esc-COP-18 are 20-40 minutes and 120-220 PFU/infected cell, respectively, preferably 25-35 minutes and 145-195 PFU/infected cell, respectively, but are not limited thereto.

Also, the present invention provides a composition applicable for the prevention or treatment of infections or diseases caused by pathogenic *Escherichia coli*, which include the bacteriophage Esc-COP-18 as an active ingredient.

Because the bacteriophage Esc-COP-18 included in the composition of the present invention kills pathogenic *Escherichia coli* effectively, it is considered effective in the prevention of pathogenic *Escherichia coli* infections or treatment of diseases caused by pathogenic *Escherichia coli*. Therefore, the composition of the present invention is capable of being utilized for the prevention and treatment of diseases caused by pathogenic *Escherichia coli*.

The diseases caused by pathogenic *Escherichia coli* in the present invention include food poisoning, gastroenteritis, diarrhea, urinary tract infections, neonatal meningitis, hemolytic-uremic syndrome, peritonitis, mastitis, septicemia, Gram-negative pneumonia, shigellosis, dysentery and cancer, but are not limited thereto.

The pharmaceutically acceptable carrier included in the composition of the present invention is one that is generally used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil, but are not limited thereto. The composition of the present invention may additionally include lubricants, wetting agents, sweeteners, flavors, emulsifiers, suspending agents, and preservatives, in addition to the above ingredients.

In the composition of the present invention, the bacteriophage Esc-COP-18 is included as an active ingredient. The bacteriophage Esc-COP-18 is included at a concentration of $1\times10^1$ pfu/ml to $1\times10^{30}$ pfu/ml or $1\times10^1$ pfu/g to $1\times10^{30}$ pfu/g, and preferably at a concentration of $1\times10^4$ pfu/ml to $1\times10^{15}$ pfu/ml or $1\times10^4$ pfu/g to $1\times10^{15}$ pfu/g.

The composition of the present invention can be formulated according to a method that can be easily performed by those of ordinary skill in the art to which the present invention pertains using a pharmaceutically acceptable carrier and/or excipient in the form of a unit dose or in a multi-dose container. Then, the formulation may be in the form of a solution, suspension, or emulsion in oil or a water-soluble medium, extract, powder, granule, tablet, or capsule. A dispersing agent or stabilizer may be additionally included.

In order to improve the effectiveness of above purpose, bacteriophages that have antibacterial activity against non-*Escherichia coli* bacterial species may be further included in the composition of the present invention. In addition, other kinds of bacteriophages that have antibacterial activity against *Escherichia coli* may be further included in the composition of the present invention. These bacteriophages may be additionally included so as to maximize antibacterial effects, because each antibacterial property of the bacteriophages such as antibacterial strength and spectrum (host range) are different in the case of bacteriophages exhibiting antibacterial activity against the same bacterial species.

In this description, the terms "prevention" and "prevent" indicate (i) to block pathogenic *Escherichia coli* infections; and (ii) to inhibit the progression of diseases caused by pathogenic *Escherichia coli* infections.

In this description, the terms "treatment" and "treat" indicate all actions that (i) suppress diseases caused by pathogenic *Escherichia coli*; and (ii) alleviate the pathological condition of the diseases caused by pathogenic *Escherichia coli*.

In this description, the term "pathogenic *Escherichia coli*" indicates enterohemorrhagic *Escherichia coli*, enterotoxigenic *Escherichia coli*, enteroinvasive *Escherichia coli*, enteropathogenic *Escherichia coli*, enteroaggregative *Escherichia coli* and carcinogenic *Escherichia coli*, but are not limited thereto.

In this description, the terms "diseases caused by pathogenic *Escherichia coli*" and "pathogenic *Escherichia coli* infections" indicate food poisoning, gastroenteritis, diarrhea, urinary tract infections, neonatal meningitis, hemolytic-uremic syndrome, peritonitis, mastitis, septicemia, Gram-negative pneumonia, shigellosis, dysentery and cancer, but are not limited thereto.

In this description, the term "Latent period" indicates the time taken by a bacteriophage particle to reproduce inside an infected host cell.

In this description, the term "Burst size" indicates the number of bacteriophages produced per infected bacterium.

In this description, the terms "isolate", "isolating", and "isolated" indicate actions which isolate bacteriophages from nature by applying diverse experimental techniques and which secure characteristics that can distinguish the target bacteriophage from others, and further include the action of proliferating the target bacteriophage using bioengineering techniques so that the target bacteriophage is industrially applicable.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Isolation of Bacteriophage Capable of Killing *Escherichia coli*

Samples were collected from environmental or clinical samples to isolate the bacteriophage capable of killing *Escherichia coli*. Here, the *Escherichia coli* strains used for the bacteriophage isolation had been previously isolated and identified as *Escherichia coli* by the present inventors.

The procedure for isolating the bacteriophage is described in detail hereinafter. The collected sample was added to a TSB (Tryptic Soy Broth) culture medium (casein digest, 17 g/L; soybean digest, 3 g/L; dextrose, 2.5 g/L; NaCl, 5 g/L; dipotassium phosphate, 2.5 g/L) inoculated with *Escherichia coli* at a ratio of 1/1000, followed by shaking culture at 37° C. for 3 to 4 hours. Upon completion of the culture, centrifugation was performed at 8,000 rpm for 20 minutes and a supernatant was recovered. The recovered supernatant was inoculated with *Escherichia coli* at a ratio of 1/1000, followed by shaking culture at 37° C. for 3 to 4 hours. When the sample contained the bacteriophage, the above procedure was repeated a total of 5 times in order to sufficiently increase the number (titer) of the bacteriophage. After repeating the procedure 5 times, the culture solution was subjected to centrifugation at 8,000 rpm for 20 minutes. After the centrifugation, the recovered supernatant was filtered using a 0.45 µm filter. The obtained filtrate was used in a typical spot assay for examining whether or not a bacteriophage capable of killing *Escherichia coli* was included therein.

The spot assay was performed as follows: TSB culture medium was inoculated with *Escherichia coli* at a ratio of 1/1000, followed by shaking culture at 37° C. overnight. 2 ml ($OD_{600}$ of 1.5) of the culture solution of *Escherichia coli* prepared above was spread on TSA (casein digest, 15 g/L; soybean digest, 5 g/L; NaCl, 5 g/L; agar, 15 g/L) plate. The plate was left on a clean bench for about 30 minutes to dry the spread solution. After drying, 10 µl of the prepared filtrate was spotted onto the plate culture medium on which *Escherichia coli* was spread and then left to dry for about 30 minutes. After drying, the plate culture medium that was subjected to spotting was incubated at 37° C. for one day, and then examined for the formation of clear zones at the positions where the filtrate was dropped. In the case of the filtrate generated a clear zone, it is judged that the bacteriophage capable of killing *Escherichia coli* is included therein. Through the above examination, the filtrate containing the bacteriophage having the ability to kill *Escherichia coli* could be obtained.

The pure bacteriophage was isolated from the filtrate confirmed above to have the bacteriophage capable of killing *Escherichia coli*. A conventional plaque assay was used to isolate the pure bacteriophage. In detail, a plaque formed in the course of the plaque assay was recovered using a sterilized tip, which was then added to the culture solution of *Escherichia coli*, followed by culturing at 37° C. for 4 to 5 hours. After the culturing, centrifugation was performed at 8,000 rpm for 20 minutes to obtain a supernatant. The *Escherichia coli* culture solution was added to the obtained supernatant at a volume ratio of 1/50, followed by culturing at 37° C. for 4 to 5 hours. In order to increase the number of bacteriophages, the above procedure was repeated at least 5 times. Then, centrifugation was performed at 8,000 rpm for 20 minutes in order to obtain the final supernatant. A plaque assay was further performed using the resulting supernatant. In general, the isolation of a pure bacteriophage is not completed through a single iteration of a procedure, so the above procedure was repeated using the resulting plaque formed above. After at least 5 repetitions of the procedure, a solution containing the pure bacteriophage was obtained. The procedure for isolating the pure bacteriophage was generally repeated until the generated plaques became similar to each other in size and morphology. In addition, final isolation of the pure bacteriophage was confirmed using electron microscopy. The above procedure was repeated until the isolation of the pure bacteriophage was confirmed using electron microscopy. The electron microscopy was performed according to a conventional method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics, the novel bacteriophage isolated above was confirmed to belong to the Myoviridae bacteriophage.

The solution containing the pure bacteriophage confirmed above was subjected to the following purification process. The *Escherichia coli* culture solution was added to the solution containing the pure bacteriophage at a volume ratio of 1/50 based on the total volume of the bacteriophage solution, followed by further culturing for 4 to 5 hours. After the culturing, centrifugation was performed at 8,000 rpm for 20 minutes to obtain a supernatant. This procedure was repeated a total of 5 times in order to obtain a solution containing sufficient numbers of the bacteriophage. The supernatant obtained from the final centrifugation was filtered using a 0.45 μm filter, followed by a conventional polyethylene glycol (PEG) precipitation process. Specifically, PEG and NaCl were added to 100 ml of the filtrate until reaching 10% PEG 8000/0.5 M NaCl, and then left at 4° C. for 2 to 3 hours. Thereafter, centrifugation was performed at 8,000 rpm for 30 minutes to obtain the bacteriophage precipitate. The resulting bacteriophage precipitate was suspended in 5 ml of a buffer (10 mM Tris-HCl, 10 mM $MgSO_4$, 0.1% gelatin, pH 8.0). The resulting material was referred to as a bacteriophage suspension or bacteriophage solution.

As a result, the pure bacteriophage purified above was collected, was named the bacteriophage Esc-COP-18, and then deposited at Korea Collection for Type Culture, Korea Research Institute of Bioscience and Biotechnology on Nov. 15, 2019 (Accession number: KCTC 14028BP).

Example 2: Separation and Sequence Analysis of Genome of Bacteriophage Esc-COP-18

The genome of the bacteriophage Esc-COP-18 was separated as follows. The genome was separated from the bacteriophage suspension obtained using the same method as in Example 1. First, in order to remove DNA and RNA of *Escherichia coli* included in the suspension, 200 U of each of DNase I and RNase A was added to 10 ml of the bacteriophage suspension and then left at 37° C. for 30 minutes. After being left for 30 minutes, in order to stop the DNase I and RNase A activity, 500 μl of 0.5 M ethylenediaminetetraacetic acid (EDTA) was added thereto and then left for 10 minutes. In addition, the resulting mixture was further left at 65° C. for 10 minutes, and 100 μl of proteinase K (20 mg/ml) was then added thereto so as to break the outer wall of the bacteriophage, followed by reaction at 37° C. for 20 minutes. After that, 500 μl of 10% sodium dodecyl sulfate (SDS) was added thereto, followed by reaction at 65° C. for 1 hour. After reaction for 1 hour, 10 ml of the solution of phenol:chloroform:isoamyl alcohol, mixed at a component ratio of 25:24:1, was added to the reaction solution, followed by mixing thoroughly. In addition, the resulting mixture was subjected to centrifugation at 13,000 rpm for 15 minutes to separate layers. Among the separated layers, the upper layer was selected, and isopropyl alcohol was added thereto at a volume ratio of 1.5, followed by centrifugation at 13,000 rpm for 10 minutes in order to precipitate the genome. After collecting the precipitate, 70% ethanol was added to the precipitate, followed by centrifugation at 13,000 rpm for 10 minutes to wash the precipitate. The washed precipitate was recovered, vacuum-dried and then dissolved in 100 μl of water. This procedure was repeated to obtain a sufficient amount of the genome of the bacteriophage Esc-COP-18.

Information on the sequence of the genome of the bacteriophage Esc-COP-18 obtained above was secured by performing next-generation sequencing analysis using Illumina Mi-Seq equipment from the National Instrumentation Center for Environmental Management, Seoul National University. The finally analyzed genome of the bacteriophage Esc-COP-18 had a size of 130,787 bp, and the sequence of whole genome was expressed by SEQ ID NO: 1.

The homology (similarity) of the bacteriophage Esc-COP-18 genomic sequence obtained above with previously reported bacteriophage genomic sequences was investigated using BLAST investigation, the genomic sequence of the bacteriophage Esc-COP-18 was found to have a relatively high homology with the sequence of the *Escherichia* bacteriophage vB_EcoM-Pr121LW (Genbank Accession No. MH752840.1) (identity: 94%). However, the topology of the bacteriophage Esc-COP-18 genome is circular, whereas *Escherichia* bacteriophage vB_EcoM-Pr121LW has linear genome. In addition, the number of open reading frames (ORFs) on the bacteriophage Esc-COP-18 genome is 195, whereas *Escherichia* bacteriophage vB_EcoM-Pr121LW has 222 open reading frames.

Based upon this result, it is concluded that the bacteriophage Esc-COP-18 must be a novel bacteriophage different from conventionally reported bacteriophages. Further, since the antibacterial strength and spectrum of bacteriophages typically depend on the type of bacteriophage, it is considered that the bacteriophage Esc-COP-18 can provide antibacterial activity different from that of any other bacteriophages reported previously.

Example 3: Analysis of the Major Structural Proteins of Bacteriophage Esc-COP-18

Figure 2:
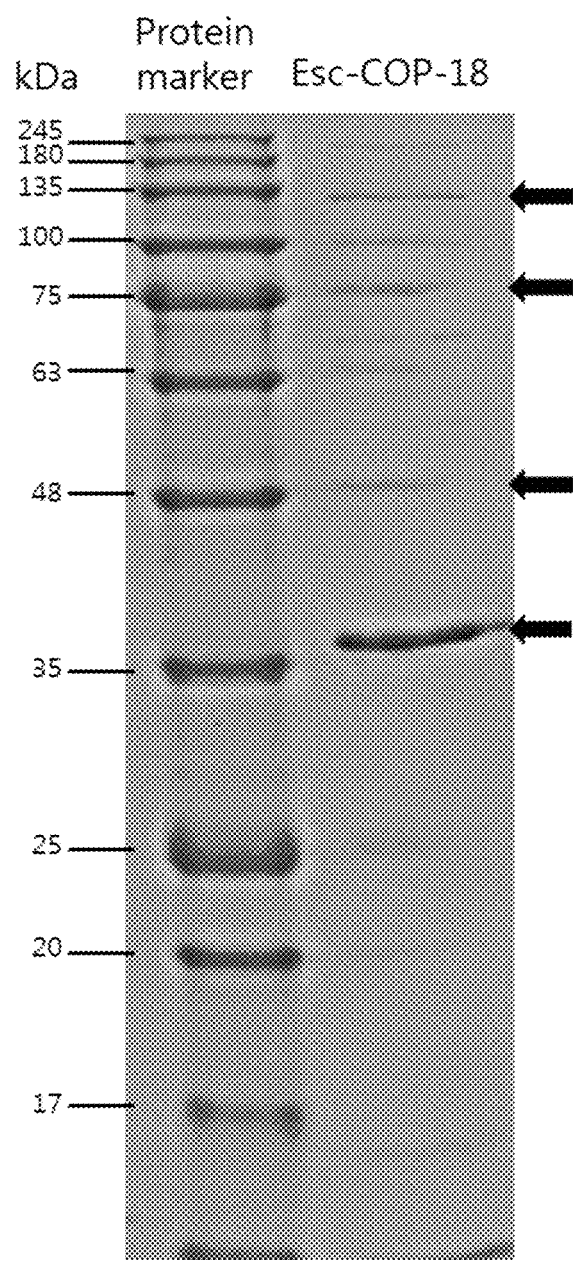
FIG. 2 is a result of the analysis for major structural proteins of bacteriophage Esc-COP-18.

One-dimensional electrophoresis was performed to analyze the major structural proteins of the bacteriophage Esc-COP-18. To obtain the proteins constituting the outer wall of the bacteriophage Esc-COP-18, 200 μl of the bacteriophage suspension prepared in Example 1 was mixed with 800 μl of acetone, which was vortexed vigorously. The mixture stood at −20° C. for 10 minutes. Centrifugation was performed at 13,000 rpm at 4° C. for 20 minutes to eliminate supernatant, followed by air drying. The precipitate was resuspended in 50 μl of electrophoresis sample buffer (5×), which was then boiled for 5 minutes. The prepared sample was analyzed by one-dimensional electrophoresis. As a result, as shown in FIG. 2, the major structural proteins in the sizes of approximately 37 kDa, 48 kDa, 75 kDa, and 135 kDa were confirmed.

Example 4: Investigation of Ability of Bacteriophage Esc-COP-18 to Kill Pathogenic *Escherichia coli*

Figure 3:
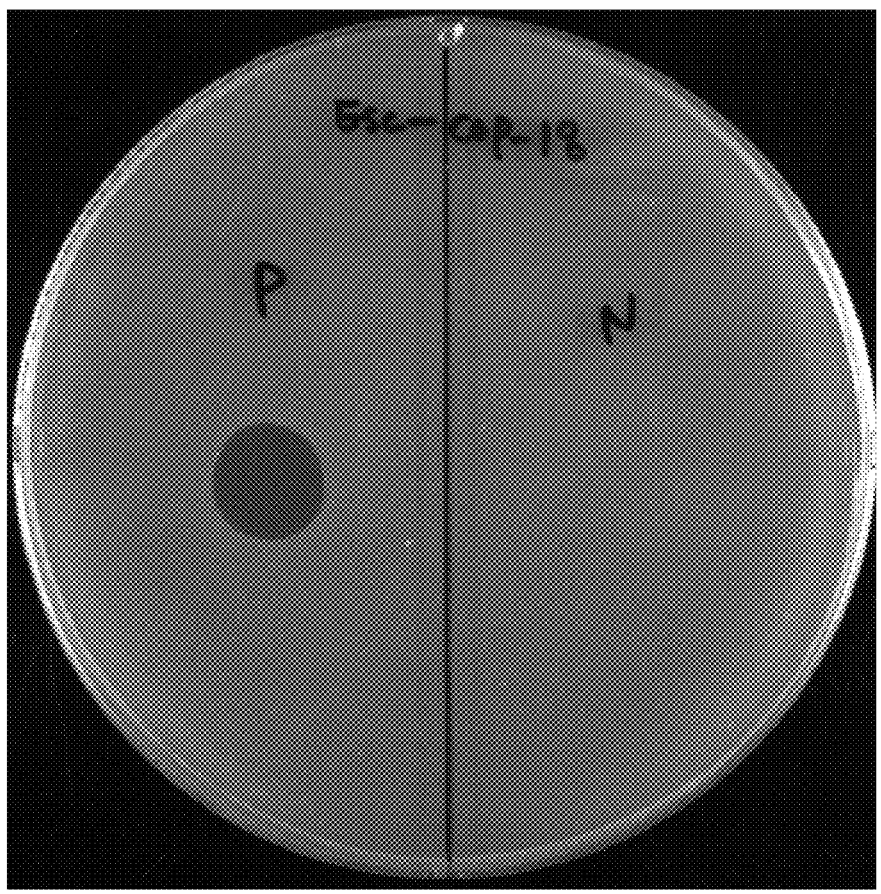
FIG. 3 is a photograph showing the results of an experiment on the ability of the bacteriophage Esc-COP-18 to kill *Escherichia coli*. The clear zone is a plaque formed by lysis of the target bacteria.

The ability of bacteriophage Esc-COP-18 to kill pathogenic *Escherichia coli* was investigated. In order to investigate the killing ability, the formation of clear zones was observed using the spot assay in the same manner as described in Example 1. A total of 5 strains that had been identified as pks positive *Escherichia coli* strains that are positive carriers of the pks genomic island were used as pathogenic *Escherichia coli* for the investigation of killing ability. The bacteriophage Esc-COP-18 had the ability to lyse and kill a total of 4 strains among 5 strains of pathogenic *Escherichia coli* as the experimental target. The experimental result thereof is presented in Table 1 and the representative result is shown in FIG. 3.

TABLE 1

Test of antibacterial activity of bacteriophage Esc-COP-18

| Tested *Escherichia coli* strain | Test result |
|---|---|
| *Escherichia coli* CCARM 1G930 | + |
| *Escherichia coli* CCARM 1G931 | + |
| *Escherichia coli* CCARM 1G932 | + |
| *Escherichia coli* CCARM 1G936 | + |
| *Escherichia coli* CCARM 1G939 | − |

* +: clear lytic activity, −: no lytic activity;
CCARM: Culture Collection of Antimicrobial Resistant Microbes (Seoul, Korea)

Meanwhile, the ability of the bacteriophage Esc-COP-18 to kill *Bordetella bronchiseptica*, *Enterococcus faecalis*, *Enterococcus faecium*, *Staphylococcus aureus*, *Streptococcus pneumoniae* and *Pseudomonas aeruginosa* was also investigated in a separate experiment. As a result, the bacteriophage Esc-COP-18 did not have the ability to kill these bacteria.

Therefore, it is confirmed that the bacteriophage Esc-COP-18 has strong ability to kill pathogenic *Escherichia coli* and a broad antibacterial spectrum against pathogenic *Escherichia coli*, suggesting that the bacteriophage Esc-COP-18 can be used as an active ingredient of the composition for preventing and treating pathogenic *Escherichia coli* infections.

Example 5: Growth Characteristic of Bacteriophage Esc-COP-18

Figure 4:
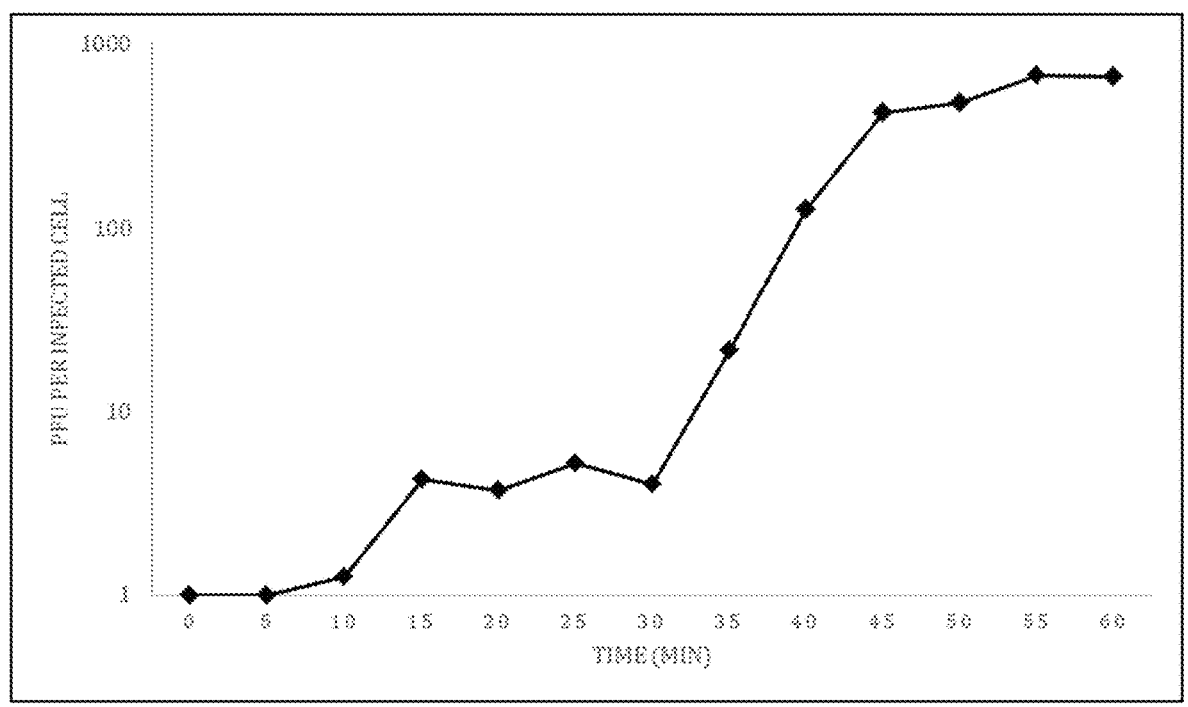
FIG. 4 is the one-step growth curve of bacteriophage Esc-COP-18.

The growth characteristics of bacteriophage Esc-COP-18 was analyzed by one-step growth curve analysis. One-step growth curve analysis of bacteriophage Esc-COP-18 was performed as follows: 50 ml of TSB (Tryptic soy broth, Difco) culture medium was inoculated with *Escherichia coli* at a ratio of 1/1000 and followed by shaking culture until exponential phase ($OD_{600}=0.3\sim0.4$). Upon completion of the culture, centrifugation was performed at 8,000 rpm for 5 min and a bacterial cell pellet was recovered. The recovered pellet was suspended in 50 ml of TSB. The resulting material may be referred to as a bacterial suspension. The bacteriophage Esc-COP-18 was mixed with the bacterial suspension at a multiplicity of infection (MOI) of 0.1 and incubated at room temperature for 10 min, and then centrifuged at 12,000 rpm for 30 seconds. After supernatants were removed, the pellets containing bacteriophage-infected bacterial cells were suspended in 50 ml of TSB and incubated at 37° C. with shaking. Aliquots were taken at 5 min intervals for 60 min, and the titers in the aliquots were immediately determined by the conventional plaque assay (FIG. 4).

The latent period of bacteriophage Esc-COP-18 was estimated to be approximately 30±5 min with average burst size of about 170±20 pfu/infected cell.

Example 6: Experimental Example Regarding Prevention of Pathogenic *Escherichia coli* Infection Using Bacteriophage Esc-COP-18

100 μl of a bacteriophage Esc-COP-18 suspension ($1\times10^8$ pfu/ml) was added to a tube containing 9 ml of a TSB culture medium. To another tube containing 9 ml of a TSB culture medium, only the same amount of TSB culture medium was further added. A pathogenic *Escherichia coli* (pks positive strain CCARM 1G931) culture solution was then added to each tube so that absorbance reached about 0.5 at 600 nm. After pathogenic *Escherichia coli* was added, the tubes were transferred to an incubator at 37° C., followed by shaking culture, during which the growth of pathogenic *Escherichia coli* was observed. As presented in Table 2, it was observed that the growth of pathogenic *Escherichia coli* was inhibited in the tube to which the bacteriophage Esc-COP-18 suspension was added, while the growth of pathogenic *Escherichia coli* was not inhibited in the tube to which the bacteriophage suspension was not added.

TABLE 2

Test for bacterial growth inhibition of bacteriophage Esc-COP-18

| | $OD_{600}$ | | |
|---|---|---|---|
| Classification | 0 minutes after initiation of cultivation | 30 minutes after initiation of cultivation | 60 minutes after initiation of cultivation |
| Bacteriophage suspension was not added | 0.5 | 0.9 | 1.2 |
| Bacteriophage suspension was added | 0.5 | 0.4 | 0.3 |

The above results indicate that the bacteriophage Esc-COP-18 of the present invention not only inhibits the growth of pathogenic *Escherichia coli* but also has the ability to kill pathogenic *Escherichia coli*. Therefore, it is concluded that the bacteriophage Esc-COP-18 can be used as an active ingredient of the composition for preventing a pathogenic *Escherichia coli* infection.

Example 7: Preventive Effect of Bacteriophage Esc-COP-18 on the Infections of *Escherichia coli* in Animal Model Preventive effect of the bacteriophage Esc-COP-18 on weaning pigs affected by *Escherichia coli* was investigated. 4 weaning pigs at 25 days of age were grouped together; total 2 groups of pigs were raised in each pig pen (1.1 m×1.0 m). Heating system was furnished and the surrounding environment was controlled. The temperature and the humidity of the pig pen were controlled consistently and the floor was cleaned every day. From the 1$^{st}$ day of the experiment, pigs of the experimental group (adding the bacteriophage) were fed with feeds adding the bacteriophage Esc-COP-18 at $1\times10^8$ pfu/g according to the conventional feed supply procedure, while pigs of the control group (without adding the bacteriophage) were fed with the same feed without adding the bacteriophage Esc-COP-18 according to the conventional procedure. From the 7$^{th}$ day of the experiment, the feeds of both groups were contaminated with $1\times10^8$ cfu/g of pathogenic *Escherichia coli* for 2 days and thereafter provided twice a day respectively for the experimental and the control groups so as to bring about the infections of pathogenic *Escherichia coli*. The administered pathogenic *Escherichia coli* suspension was prepared as follows: Pathogenic *Escherichia coli* (strain CCARM 1G932) was cultured at 37° C. for 18 hours using a TSB culture medium, after which the bacteria were isolated and adjusted to $10^9$ CFU/ml using physiological saline (pH 7.2). From the next day after providing contaminated feeds for 2 days (the 9$^{th}$ day of the experiment), pigs of the experimental group (adding the bacteriophage) were fed again with the feeds adding the bacteriophage Esc-COP-18 at $1\times10^8$ pfu/g without contaminating pathogenic *Escherichia coli* according to the conventional feed supply procedure as before, while pigs of the control group (without adding the bacteriophage) were fed with the same feed without adding the bacteriophage according to the conventional procedure. From the 9$^{th}$ day of the experiment, diarrhea was examined in all test animals on a daily basis. The extent of diarrhea was determined by measuring according to a diarrhea index. The diarrhea index was measured using a commonly used Fecal Consistency (FC) score (normal: 0, soft stool: 1, loose diarrhea: 2, severe diarrhea: 3). The results are shown in Table 3.

TABLE 3

Fecal Consistency score

| | Fecal Consistency score | | | | | |
|---|---|---|---|---|---|---|
| | D 9 | D 10 | D 11 | D 12 | D 13 | D 14 |
| Control group (bacteriophage suspension was not administered) | 2.5 | 2.0 | 1.75 | 1.75 | 1.5 | 1.0 |
| Experimental group (bacteriophage suspension was administered) | 1.0 | 0.75 | 0.5 | 0.25 | 0 | 0 |

From the above results, it is confirmed that the bacteriophage Esc-COP-18 of the present invention could be very effective to suppress the infections of pathogenic *Escherichia coli*.

Example 8: Example of Treatment of Infectious Diseases of Pathogenic *Escherichia coli* Using Bacteriophage Esc-COP-18

The therapeutic effect of the bacteriophage Esc-COP-18 on diseases caused by pathogenic *Escherichia coli* was evaluated as follows: 40 of 8-week-old mice were divided into a total of 2 groups of 20 mice per group, after which subgroups of 5 mice each were separately reared in individual experimental mouse cages, and the experiment was performed for 7 days. On the second day of the experiment, 0.1 ml of a pathogenic *Escherichia coli* suspension was administered to all mice through intraperitoneal injection. The administered pathogenic *Escherichia coli* suspension was prepared as follows: Pathogenic *Escherichia coli* (strain CCARM 1G932) was cultured at 37° C. for 18 hours using a TSB culture medium, after which the bacteria were isolated and adjusted to $10^9$ CFU/ml using physiological saline (pH 7.2). At 2 hr after administration of pathogenic *Escherichia coli*, $10^9$ pfu of bacteriophage Esc-COP-18 was administered through intraperitoneal injection to mice in the experimental group (administered with the bacteriophage suspension). 0.1 ml of saline was administered through intraperitoneal injection to mice in the control group (not administered with the bacteriophage suspension). Both the control and experimental groups were equally fed with feed and drinking water. Whether or not the mice survived was observed daily starting from the administration of pathogenic *Escherichia coli* until the end of the test. The results are shown in Table 4 below.

TABLE 4

Survival rate

| | Survival rate (%) | | | | | |
|---|---|---|---|---|---|---|
| | D 2 | D 3 | D 4 | D 5 | D 6 | D 7 |
| Control group (not administered with bacteriophage suspension) | 100 | 75 | 55 | 25 | 15 | 15 |
| Experimental group (administered with bacteriophage suspension through intraperitoneal injection) | 100 | 85 | 80 | 80 | 75 | 75 |

As is apparent from the above results, it can be concluded that the bacteriophage Esc-COP-18 of the present invention is very effective in the treatment of diseases caused by pathogenic *Escherichia coli*.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

Accession Number

Name of Depositary Authority: KCTC

Accession number: KCTC 14028BP

Accession date: 2019 Nov. 15

What is claimed is:

1. A composition for preventing or treating an infection or disease caused by a pathogenic *Escherichia coli*, comprising:
   a Myoviridae bacteriophage Esc-COP-18 having an ability to lyse the pathogenic *Escherichia coli* and a genome represented by a sequence as set forth in SEQ ID NO: 1 and
   a pharmaceutically acceptable carrier,
   wherein the Myoviridae bacteriophage Esc-COP-18 has a latent period of 25-35 minutes and a burst size of 145-195 plaque-forming units (PFU)/infected cell and is deposited in the Korean Collection for Type Cultures (KCTC) under accession number KCTC 14028BP;
   wherein the Myoviridae bacteriophage Esc-COP-18 has major structural proteins in the sizes of approximately 37 kDa, 48 kDa, 75 kDa, and 135 kDa; and
   wherein the Myoviridae bacteriophage Esc-COP-18 has a concentration of $1 \times 10^4$ pfu/ml to $1 \times 10^{15}$ pfu/ml or $1 \times 10^4$ pfu/g to $1 \times 10^{15}$ pfu/g.

2. The composition of claim 1, wherein the pharmaceutically acceptable carrier is lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, or mineral oil.

3. The composition of claim 1 further comprising:
   one or more selected from the group consisting of a lubricant, a wetting agent, a sweetener, a flavor, an emulsifier, a suspending agent, and a preservative.

4. The composition of claim 1, wherein the pathogenic *Escherichia coli* is enterohemorrhagic *Escherichia coli*, enterotoxigenic *Escherichia coli*, enteroinvasive *Escherichia coli*, enteropathogenic *Escherichia coli*, enteroaggregative *Escherichia coli*, or carcinogenic *Escherichia coli*.

5. The composition of claim 1, wherein the infection or disease is food poisoning, gastroenteritis, diarrhea, urinary tract infections, neonatal meningitis, hemolytic-uremic syndrome, peritonitis, mastitis, septicemia, Gram-negative pneumonia, shigellosis, dysentery, or cancer.

6. The composition of claim 1, wherein the composition is a solution, suspension, emulsion in oil, water-soluble medium, extract, powder, granule, tablet, or capsule.

7. The composition of claim 1 further comprising:
   a second bacteriophage having an ability to lyse a pathogenic *Escherichia coli* or a non-*Escherichia coli* bacterial species.

8. A method for preventing or treating an infection or disease caused by a pathogenic *Escherichia coli*, comprising:
   administering to a subject a Myoviridae bacteriophage Esc-COP-18; and
   lysing the pathogenic *Escherichia coli* by the Myoviridae bacteriophage Esc-COP-18,
   wherein the Myoviridae bacteriophage Esc-COP-18 has a genome represented by a sequence as set forth in SEQ ID NO: 1;
   wherein the Myoviridae bacteriophage Esc-COP-18 has a latent period of 25-35 minutes and a burst size of 145-195 plaque-forming units (PFU)/infected cell and is deposited in the Korean Collection for Type Cultures (KCTC) under accession number KCTC 14028BP;
   wherein the Myoviridae bacteriophage Esc-COP-18 has major structural proteins in the sizes of approximately 37 kDa, 48 kDa, 75 kDa, and 135 kDa; and
   wherein the Myoviridae bacteriophage Esc-COP-18 has a concentration of $1 \times 10^4$ pfu/ml to $1 \times 10^{15}$ pfu/ml or $1 \times 10^4$ pfu/g to $1 \times 10^{15}$ pfu/g.

* * * * *

SEQUENCE LISTING

<160> NUMBER OF SEQ ID NOS: 1

<210> SEQ ID NO 1
<211> LENGTH: 130787
<212> TYPE: DNA
<213> ORGANISM: Unknown
<220> FEATURE:
<223> OTHER INFORMATION: Myoviridae bacteriophage

<400> SEQUENCE: 1

```
ggacaagttt ttctcctctt tgtcaagtac tacattaaaa atttacaatc tggtatggta     60
gtattttttc ggccctgttt acattcagga gtgtatgtat aatccttgtg gtgtgggcgt    120
ttggacgtct agacggtcag aagtccgcag gttaataact aatctattgg ttgctaacta    180
tatccccac aaataataag aaatacaatt gttatatgcg taaacagtaa cccatgttat     240
caatccctgt atgtatctcc agtggtgcgc ataatgggta ttatgttaaa ttgcccgtaa    300
tgataacagt tctcacaatg ataggtattc tcattcaccc gcccaagata ggctgcaaat    360
gttgtgccac tgtgtgaacg gcctcgccta ttaatttgcc tcactgcccc gatatttgag    420
aattgttata agaatgagaa gtattcccat tccgtccgcc tggcagcgct cctgtaggtc    480
aggtcaaaat cgtggcagaa ctgggccccc ttcagatatt tctggctgac tcttcaggtc    540
tgtgtgggaa aagccaacct ctccggcggc ggggagggga caattaaaaa atttacgtgg    600
tgtatgaagc gctcttcagg taaggcaggt attatgggat gaaaccctct tcaggcaatg    660
atatttgtag gtgtgatatt tgctggaaag ccagatatga cgggactccc ggcggggatg    720
gggtagtaca gacagggaaa atgtggagaa tgtggtgggt aaattgatca ggcaggtaga    780
gtatggaata tgttacaggt atgttaaata tggaggtaag atatttgtaa gatttgtgtg    840
taaaatcaaa gacttaagtg gtgttgtggt attttctata aataattcaa gtttaatagg    900
taatatttgt ctctatccac tttgtgtggt aaccagattc agatgaaatt ggtttacaag    960
tgtatacata atatacaaat taaagataca agaaaccccc ctccccttc ggctaccatt    1020
cacctttttcc tctgactggt acttaaacac ttattcagac tcttcaggtt atcacccata   1080
taccatatgg cagtgactgg tgtcctccgg ccctctttc gtcacccgtc cgcttcgcca    1140
tgctaatgcc atagctaact gttcggttgt tcaccctgtt cactcaggtg tatctccata    1200
ccccttcaaa ccgaagagaa cagaaaaccc gaattactcg gtaaagaaa agagaagaac     1260
ttaatttat caagataggc aagaatgtca aggcatgact gctcactaaa caagcaaaca    1320
gtcatgtgtg ggaggtaagt gattgtggtg gtaggaaatt tagttgaaag atgtgttata    1380
ggtgcttcca gcactttagc ctggcagcta attgtgtgtc agtccagcgg ttcatcctct    1440
acttcactga aatcaatgtt catggtctct tcccaaccat cgatctcagc acaagagtgg    1500
agttctttag ggtttactcc caaagcctca gcaacagagt ctatatttaa cacctctggc    1560
aggtatgatt catcgaattc aaggtaaatc aggccacgag tgttgtcagc tccaccaaat    1620
atttctatct tcatgaaatc tcctctggaa atgagagtgt gaacagggtt atacgttcca    1680
atgcacttga atttatatac gtttgcctct tcaggccatg ctttagcatg ataaacttgt    1740
gtgggctcgg tgcttcatag tctgccacct ctgaactctt cgttctcagg catgatagag    1800
aaccagatgg ctatgatgtc ctcccacgtc aggtcatcag cctcagggtc cacctgggac    1860
ggagatagag aatcctcaga attgaagttt ttctctgcgg tcgcttcttc agatgtctct    1920
ttaggtgcat gtgtgttggt catgtcccac ccgtgagtat tcctgcaaca gctgctatgg    1980
acgtaatgat catcaggatc accaccaaaa cctcggataa tgttttcatt gcgtattcca    2040
```

```
tattctccaa acgatgtgag gatactatca caggagcggt aatgtgtcaa cagaaacgcc   2100
gcgagggttt ggttaaaatc cgagcgtatg gtgatttggg tcaaaacgga cgtgcgttct   2160
cgctacgctc gaaatagaga gttgtttgta agcggctctt aaacgctctg tagtgagatt   2220
attcatctaa ggtatgcaat cgtgcaccag ataaagaaaa ggacgccaca gagcgtccta   2280
ggtgccttaa atttgatatt ttgctatacc catgagggct tgtccagatt ggagtagctg   2340
aaaggggtca aaaggtgatt gtcaaaatct ttcaaactat ccaaatcttt ttcctcgtcc   2400
tgacaccatc tgtgcctaca tttattgttg tagtgcatag aatgcatagc gttctgcaac   2460
ttaacaggca caagtgattc aggagtagat agtattgtcg ggtatgccag aaccacctca   2520
aacagtggaa acacatcgaa actaaagtct acctctgcag aggttgatgg catataggag   2580
tatttagccg cccttgtaga cataatccac ctcacacagg tttgataata cctttaccga   2640
ataactcttc gtatctaatc ttatccggat cccactcctg gataatttcg aagacaatat   2700
ccaaccctgg gataatcact tctccagtgt caagtttggc aagaacaaaa ccagaaggct   2760
gaatggtttc ccagttgcga cgattggaat agaagacctc aaaaatatca ccgaccccga   2820
tctgttgatc aagatgttca agattctctt tcatacggac gcagcgtatt tttcgtgcag   2880
gccatagacc gcctgcatca cgttcattta gctcttttac agtgatcggt atcccatct    2940 caaatctcct tcatagatag taaaaagagg ggcccaagcc cccctctttg tcattattct   3000
acagagcgtt tgaacagaat gtctgcctcg gacatgtgtt caacctcttc ttcgatttta   3060
gctcgacgtt tttcagcctc atagcgaata tcgaactcgg tagccaccag agatttgatg   3120
aatttaggag aatacagatg atcctgcttc tcaacaagaa tgatatcctt gatggcatct   3180
ttcagatctt taatctgaag ctggagttcc accagttctt cgattgtttt gcgaaggcga   3240
tcacgttctg cagtgtcaga aggaagagag gtgaacagtt caactttaga tttagccata   3300
gtaagagtct ccttatgttg ttttaaatta acgttctaca aaaataccgt tcagttcaat   3360
aaccagaaat ttctggtctt cactatcgtc tcgtgccagc acctcacaga cgtatcggtc   3420
atccccatca tcatcgcagt caaatacaag actgaggact ttatcatggt aaaccttcgc   3480
cactaccgcc tcgtaagtat tgccgattgt gaatccaaga taatccccga tgcatttgac   3540
aacaacatgg tcgccagcat ttaagtcaat cttcgtcatt actgtgctcc ttgggtgata   3600
atatggtatg taaaacttta accagagatg tgaataacgc cccaaaacac accgacagcg   3660
ctaaaacaga taaggccatc attaaagctt cagtaaaatc agtcattcct cacctcttgt   3720
tagtaactat actatcattt atcttcgccg tcaagaactt ttttaaatct ctcaggaata   3780
tctcctgttc ttagatagct catgacctcc caaggtttcc acttgaactt cttgcacagt   3840
aaggcagccg agatcgtctc gttgcgaaaa gaaaggatat taatatccca ctctgagaac   3900
cccaatttcc gaagggtagc tacagaaatc ctcaccgcaa cccagcagca aaaacatgca   3960
acaaacgcca ctgctacaac ccacatcagg atgttcatac agccccctta atgaaataca   4020
aggcatagtg ttaaggttgc tacccagcaa ataattaaca gtgccgttgc aaccttggca   4080
agatttatca tagtgtctct aaaatttcat acccttcggg tcggaaaaca agccactcag   4140
gtgctccatt tggtcgatac gctttataca gaacaacctg atctcggcac atgcacatgg   4200
ctacatagtt ttcatcaaca cctgcctcct gcattgcatc ttcttctccg gcaacagcct   4260
tgcttacaac ttccttggta ggcaggtggg cgatcagctc gtcaccatcg ttaattccaa   4320
aatgactgag ttctccattg gtatctttaa tcttgatctt aaccaaatct ttcattagtc   4380
```

```
ttcctccagg ttcaaaggtc ctaagatttc atatgctaga ttagaagtta ccagagggtc    4440
ttctgcatct ttagtattat accatccgtg aataaccaga gtcccgctgt gttgcatgtc    4500
taactggaac tgctctgccg tttcctcatc catctccaag atctccatga ggtatttgat    4560
gttagggaga tatgcggttg ttacagtccc ctctaccaga ccttcaggcc aacctacatc    4620
cggatgacaa gtaggaacca gagaggtcag tttaataatg tatgcttttt ctgcacgagc    4680
cttcagtaac ggatcaattt tcattattct tcctcctctt cggtgcctgc ttccagtagt    4740
aagttaagaa catcttcagc agaaggttcg tagaactctt ggccttcgtt gtcgatgatg    4800
cgatagtcat caccacgaat aatcagagga tcgtcatcaa aaccttcaag acctttaaca    4860
acgacaacac gatcgattgc catcattgta agaactttat cgacatcttc ctctgctaca    4920
ccatactgca gcagaatgtt tttggtagga ggaacagcat ccaccacaac gccgttacca    4980
aaaccttctg gaagtttagc taaaatatct tccggaacca cattcacatc aaaaccggta    5040
atttctactt tcatttacag cacctcttcg tcaactactt cataaaaatg gcctgggatt    5100
gcaatagcgt tctcaccttc acctacaaac acagttccgt caagaatcaa catcataaga    5160
atttcttgaa tatcctcttc cggaacgttg ccaaaacctt taatcagctc gtaggttgga    5220
agatttacct ctaagatgtc accatcttta gagcggaaat caacaccatc ctgaatctct    5280
gccgtttcaa ggttttttcaa tttaatcttc atcaatcagt ctcctgtctt gttaagatga    5340
aggtattatt gcacacaggg ttggtgttgt caacacctgt gtgggataaa attactggaa    5400
cagtgcagat aaattacctt ctggtgggaa cttatccgcc aagaatggag tcagaacagt    5460
ggccttctga agatctggag tccactcgtt gttcagaaca tcccagtagt acgcaatgtt    5520
gctgtgtggg tgccgcatta cgaacttttt cccttcgtag tcagttgaaa cctctacaga    5580
agaaataaca acagaatctt caagagtttc ttcatagaaa gatccaccct cgaatttcca    5640
acgagatgca agagccctg ccttaaacgc tgcagataac ggactgtcgg caagaacata    5700
catttcttgc actctgtcgc tgcgatcttt gcttcttacg ttgtatacag tatctgagct    5760
atactcaaca cggtatagac ttaccattac cgcacctcct caataacttc cacatctgaa    5820
cctaccacaa atgcaaaagg gcaggtttca tgaaagacat ccggatcgcc accaagcttg    5880
ctaactattt ctccaccact aataaacaca agctcaccga tattcatcag attgctgaaa    5940
tagtatccat aatgattaaa gaatgcagca gggtcaggca gactggtagc ctcaagctct    6000
acatcggttg agattacttt cttatcatac cctctggcct tttgagatgc aagatctgca    6060
gaatcctcag gcgaccggag atgcacagga attgttcac caataaagcg tactttcata    6120
ttctcaccca acaaccatag cttcaaaagg agtcatgaac gaataaacgg catcatcatc    6180
tgcttcaggg aatgctccca aagacttcat gtctgagccc ttgacaaata caaggtttg    6240 atcaaaggct tcttgggggt caatccgata catatttcgt agaatatcgc ttacctcctc    6300
atcaagaggt gagtatgctg tgcacgtttt tccgatcaag ctttgagaat caggatatcc    6360
acctgaagtt ttaaaataaa caatcatata gtatcacctc tagtaagaga ttgggattcc    6420
tttcccacaa ataattacaa acttttcttt ttattgagag aagtatgcta atccaagcag    6480
gattactctt ctacaatctc atacacatca ggggttacaa tcaactcttc tccgttacct    6540
ggagcaacaa acactaccaa gccttcaggt gtgtgctttt tagccatctc gatgacatct    6600
tctcgcagag ctggatccat cagatcaaaa ccttcaccca gagcatcacg aaccaccttc    6660
atgtagtcca ctggttgtgc ttcaacgatc atgccttcaa ccagtccgca gttttttgtct    6720 gccagctcag ttttgaataa tttaattttc atttagaggt ctcctcaatt atttgatatt    6780
```

```
aatagccgta acctaacaca ttaactacaa ctgcgattgc aaacataatt tcaaagcatg   6840
caatctctac atttgggact aatttcttaa tcatacccat tgtagcacct caatcccaaa   6900
agtcaatctt tactttacct tttcccttac ctttctttcc accgcattta gccaactggc   6960
gtgctgcaac atccaccata cggtcagttg cctcgtaagc atcgctacct ttagctttgg   7020
cgataacttc tttcccagaa ttgtcaaaaa taaaagccat gacttcctgg tgatcatttt   7080
caacttttac actcacacgt gcatagttgg cagaggggtg caaacgctcc agcttagaca   7140
ttttgtggga aatgaaagac accataacct tcagtgattt cacgttgcca gtgatttcaa   7200
tttgcataac gtgctccttt taaggaagag agaataacaa ccatctctct ttgaaaacaa   7260
taatactata gctgaagcgt tgtgtcaaca gttttttacag cttattatcg atagtatcta   7320
aaatatctac agcaagatct gccattttc gaacatactc tgcaaactca acaggatcct   7380
tgatcaaaga attcacaggg tcgtaccta gagcgttcaa aatggctgca gcatctacaa   7440
ccttctcatc atttgcgaag atctctccgt caaacttgtg ggtccatttt gagtcaatct   7500
tggcagagca tggttggtca atgcttgtta caccatcgtc tttaaactct cctgcgttat   7560
caatattcag aactaaatcc atcatagtgg cacctcactg tttcagtcta gcttttcttc   7620
aacaaccccg tagctcgggg cagagtcaag agcttttttgg tttaaaagtg gtgtagcaga   7680
atctgcaaac ggtgtccaag ttttttgttct ggcattccag taatgcttca ctctggaatc   7740
tggatgcact ataacaaaaa cttttttcact tgtcaacaca ttaatttctt ccacacccctt   7800 gctgacaatt tctccgtcat agcccccagt ctggtaccct tcgtaccagg ttcttgcata   7860
ggcatagcca gcctgccagc atgcagcctc ctccgaggtg gagactacgt agaagtcttt   7920
ctcaaattct gggatacgtc cttgctttac gctccaagct ccgcgaattt tcattgttac   7980
tttgaaaagc ttgttcttca tactaccgct ctacaatctc tacgtctgtt cctacaccga   8040
aggcatagta atgttcttcc ccaaagtaat acttggggac accagctttg atcaggtcta   8100
acccgcgaat aaataccaca ccgtgtgata cagtggaatg cttctgacgc acaggatcgt   8160
tgtcaggcaa ccattcaaag tacaccgcag gtacaacctt cccttaaga aaggattgcc   8220 ccaagtagac gttagaatca agaattttga ccttcatgat cgtcctccac tatctccaca   8280
tcctccccta gggcaaagtt gtaggtccac tgactgtcaa agcagtcctg agatgctcca   8340
gcggcaataa gatctgcacc cttattttt aaaaggtcag gataatcttc gttagggaca   8400
gcggtaaaca cttttccaac taaaggctct tgaccaatat agaagtttga atctaaaact   8460
ttcactttca tcagcggtct ccatcgggcg gttgtggaac gtaaacactg ctacgaatct   8520
cgtcagcagt atagtaacaa gttttcccct ctctgtccct ggcagcaatg tattcagcta   8580
taccaataag tgccatagcc ttggtggcgt atctcttaag ctcgttagct ccccagcaaa   8640
atctctgcca aaacggtatg aagccgaata ggtacacctt ctgtttcact atccaataag   8700
ttcctttaca gatcactta aactctgcag cactgttact gacaccattg ctcattatct   8760 tctccttta tttttctggg tttggcagat attgcacatt ggcaggagga acaccggata   8820
gctcccaaac aaccatagtg ctgtaccctg gcacacttct aacatttaaa agagtaggag   8880
caccaacaca tttaaacttc cttttcccaa atccgttctc catcataacc cagtatcctg   8940
tatcctgatc acctggaatt tgtgttccat catcgtccac ccagcggacg gtccatttcg   9000
atacagcaac ggctcgatat ttaaactttt taaaccactc aaacagtttc ataattcagc   9060
ctcgcatagc cataataact ataaacagac aaataatgaa tccgaatgcc acgccaccca   9120
```

-continued

```
taaacgttaa tattgatgcg accataatca atcatcctcg tttggcagct cttccatttt    9180
gacataccgg aaagtgttgc cgtaatagtt gatccatgac atcagctcgc tttcttgctc    9240
ttcctctggg attgactctc ggatgctgac aagttttaag aaaatccaat cacaatctgc    9300
acccatccta ccagacaggc aatagtgctt catagaaccc tcccgaccgg tttagaatat    9360
tgcttcttcc attgcacctg agagcaacaa agaggtaata tggctaacat tcatctcaga    9420
ctccacttcc tcccctttga aaggttcgcg gcagaatagg actgtttcag gactttact    9480
tcgaacaata taatacaaat cattcaatgt gttgtagtaa taagtgttaa aacgtaagtt    9540
tttcattttc tagccccctt cttagatttt tgtgcagaaa cgctttctgc aatacgagac    9600
aggcgttctt ctgaagcttt acctaccccca ggtttcttga gtgggttatc tttatgaccg   9660
caatccaact ggatgctaga tacatcccca accttgtaag ttaattctag caaaaggttg    9720
tcgtccttgt caaatgttct tacgataaat ttttatcgt tctcctgaac ttcatatctg     9780
gtacctgcag tatacagcat ggtgccatca gcataggata tccagatcat tgagcctcct   9840
tctgctgcaa cagcattaac tctttgttgg aaatctttac tgctgtcttt attgttccat   9900
cttcacggaa ccacgaccag aattctacag tgtcaccact atcaagcaag gcatgaccat   9960
ggtaaaaatc cttgtcctta gacagtttct catctatatc tgcatcgaca cattcgtgat   10020
ccatagcatt ttgcctgaat gcatcggtta tgccaatgca tgccttgctc tcaagactgg   10080
catatccgat atcttttaat tcagtttccc aaacccagaa ccctataaaa gccacaacag   10140
ctacccacat aatatcgat ttaatctttg acattctctc tacctctttc ttaatttgtt    10200
taattatggc acatcctttg tgccttgttg cacactactt agacaacagt tcaaaatggt   10260
gcaaaattaa cagaagttga attacgccta gcacaacggc aagtatgtta atcttagaat   10320
caaaaaactt cttaactttt actctaaaag gttccttaat gtcctttacg atcctatcta   10380
tagatgacct catatctctg attaccatcc tgaacattaa agacggatgc tcccccatct   10440
ctgtaacgga atcgaaaaca tactctcttc ggtcataagg gccgccagct ctgcgtatta   10500
acctctccac agagacctcg aacgtcacac ctgtaacgta atcatctata acaagtcgtg   10560
acgggtcttt acctttacta tcaagaggta tcaaagctat cttccagat tttgttaaaa    10620
tttctccttt ttcaagcaag gtgtaccaat gctctctacc aagattgttg aggcacgttt   10680
ttacatattt aacaaacatc gtcaccccctt atcgcacgtc tgatataacc attctatgaa  10740
atcttgatac cactctccct ctgagcgctc cgtaggccaa taatcttccc cctctcttgc   10800
attaaaatct gagtattcaa cttttccactc ctttaccagc tcgtggagaa ggttttcggc  10860
ctgttctaag gatttatttt ttgtcattac tgtcccctttt tcaagataa ttatacatca    10920
gtgccgcgcc acccaaaatg gctactagca gtaatactcc ggagagcatt tcaataaaca   10980
tggcttgaaa cattagaagg tcccctctaa tttcacgcac cattttaaat acacactctt   11040
ttcccatgaa gatactgaac taaggtctgt atagaatgca atctccctaa gaacagtata   11100
aacagtttca ggcactgtta ccattcttat ctacctcctt cattttcctg acggttttac   11160
agtgatccac caagcacata accacaatga agagaacaac aggccaaaaa ggtgcggcag   11220
tgattatagt tataaagtcg tcaaacttaa tttttctaca agatatgatg caaagagttg   11280
ctaaaacaac cattgtcaga aaggtcaatg cgcaatacca aaccagcaca gtgtctatag   11340
tcatactaca tctcctggtt caaactgtta agaaaggata ttctgtcttc gctattttc    11400
tctgtgatgt accctccaaa catggaaaga atcacatgct tcaagtaatc ttttcttgg    11460
tcgcttagat gattgcgtgg ctttatttcc acatcatgat agtcgtacaa tccacaatca   11520
```

```
tgatacctcc agtatcgaca cacctcaata ctgatcggga gttttttgtc acacgaaact   11580
ttccaacagg ttacgttgtt accagggata aatcctcgcc caccttcacg aatgacaaat   11640
cgtaattcat aaacttttcg tacagtttaa gtacaaaacc ctctacctgt ggagaaacac   11700
cagccactag ctgggcgtat ctatatttac tttcaataat ttttcggcgc tttgctgtaa   11760
ggtttattgc agcaatttga ctttctgagt atctccaagg cttatatata aatgctttcg   11820
ggtctttatc gccataaaaa tctttccaat caactagcag catacctgtc actcctccac   11880
aacttcaagg cctttgccgc ctcgttctgg tagattactt aaagacaggt aatacgtata   11940
gtcaggagag atcctaccag actctgcacc tgcagatagt aaatcttttc ccttaaccat   12000
gacaacatta tcgtttgcag atagtcgttt tgcttccaca attttaccaa cgcagtcaac   12060
caaggaaggg taccctaaat ctgtaagaaa tttaactttc atgctacctc ctacttctac   12120
cgtccctggt aagataaatt attactgaac aaagcgcgga gctgggaagg ataactcttc   12180
taaagagaag atttcattcc ccacaatcca tgttgcagga tcatctgggt tgactggata   12240
gataatcatc acctcgtcag tgttacatac ccgcttttta cctgtggagt catcagcaac   12300
cagcatgcgc ggttcttcag aaatgcacag gtagcctcct cggcccactg ttccttccac   12360
agggtcttgt cctttgatca cgatgattat cttctctcct gaggcgatat taccttgcac   12420
actcaccgtt tgaccaacct tggatgtgcc aatcttagtg acttcgaaca ttacatcccg   12480
aattactgtt gcataatcgc cagacacttt cttaccttct ttagtgatct caatcttcat   12540
acactgggct cctaaaatga atctatgtaa tcaattaaat cccaagcatc cctatgacct   12600
gtcagagggt atacttctcc aaggggatc atagcaataa gtctatcaaa acccaatct    12660 ggacgcaaca ttttatgatg atattccac tcaccttcta cagattttt ctgagtgatc    12720 agaatctctg tgtagtgttt tgcctgtctt gagtaaattg aaaacgactt atacatagat   12780 gaccccctc ttgttgaaaa caaaatacac tactaccaag tcactgtcaa gtaggcaacc    12840
gtgttatttt tctccggaga gatgccaaca acatccacct gcagacctcc tgccctcaaa   12900
tccccaacga tgtgtgggaa gtagtctgag aggtgtgatg ggagatttat cgaaaatccg   12960
catcccagaa agcctgctaa cgcttttattt tgtatctccc ctacaatcgc atcataaata   13020
gagttaagct cgtcaggaag cgttacagga cgttttagcg ctaactggtg caacttgtcc   13080
ttagcactca tttttcatttc aagtctgcct ctggtggtgc caaccacata aatggcggca   13140
agtctagacg gttttttcttg tcccatacaa aataggcata tgcctgccca tccgttctac   13200
cattggattg gaatgacgga cgcttagata ttgtgatcac agtggtaggt gcattatcaa   13260
gccaccattc aaatctggcc ttgctttcca gaaaattaag acgcaaaagc ataataacta   13320
catcggcatc tttcaacgcc ttgtctacaa actcacgagc caagctgtac ggtgggttgg   13380
tgataataca gtcaacatgg ttgtattctg tattcagata gtcaacacct tcttggattt   13440
ctccccatgc agatcctaac ggcatacggg agtagaacac acctgaggca ctattcctgc   13500
aaggctctaa gtaagtccag tcttctggga acggaataag gtcatacagc ccttctgcac   13560
accactccgg tgtcacatac tcatcgtaag cgttacgttg ttcatcaggt tttctagcac   13620
aagtcatgca aatctccaga tcataaaagc cctccgaaga gggctttaga attaatgttt   13680
aagcttcttc gacaattcct gcgcccagga ttttttcatt gagctctttt gctgttttaa   13740
taatattgtc caccagacgc ttacgggtct tatctttcac ctgaacttct tcgccgccgt   13800
tcagggtggt tttcaattgg gacaaaatgt cctgaagctc taccacagag aatcgctgca   13860
```

```
gatcttccga ggtaatctca cccagtgcaa tcttaacggt ctcaccactc tccatctgca   13920
gattcaggaa cacagtgtga acatcacctt tcataccatt ttcttttgca gactcaacag   13980
catgaaccag ctcgtccaaa gatgtgcatt ggtgaatctc tggcaggcct gcttcgccta   14040
gcacaccttc ttcatcactt tttgccaaaa gcttttcgg tttctgtcca ttctgaatgc    14100
gctgaatgtt ttcatcgtcc agaatgatag caccagttct agatgccagc tcttctccat   14160
ctaaccacac ttcaccgcca gctgtgatgg atgcgatctc atcttctgtt aacaccccac   14220
catagtattt ttcaatcagg cgttcaaaac gtttcttcca gtagttgatc tgggtattca   14280
tgttcacacc gttaccatag gtgccacctt gatagtagtg aacataaat tctgtgtccg     14340 gagccacagt ccgctctttg caacccagcc ataagattgt ccctgctgag cagcacatcc   14400
cttcagcgtg tacgcaacg cttgcctgag actctcggaa tgcctgcaaa tacgccatag     14460
caatgtgaac gcaaccacca gggctgttaa tgattacacg atactttct tctggctgtg     14520 ccgtacgaat tgtttgcaaa cgggacatat gatcctgcaa atcttcaaga tcgtcaatat   14580
aaagaacgtg gtcaacaaca ggggttgggt agctgtatgt ttccataata ccacccggca   14640
taccaaacat tttgttactc ataggttcga aaccgttctg ttttctttc atgccgtgta    14700 ccatggtgct gcgaggtgtt aaattcatga gaaatcctta atattggaag ttgaaagcta   14760
tttatttaaa cctgattcac atttacctt atttagcaat cactatagaa tacttacgat     14820
tgtcagaagc atcgcagctc aatgattgcc agtctaccac ataccacgta tcattgtcaa   14880
caattacttt atcgcctgtt ctgtagcagg tgctgctttc aataatccga gactcgataa   14940
agaatctgtg tctgcgctca cgtagcaacg ctaagttgat tatgttacca ccgctgtcct   15000
tggtccacac attcttggat cccttatttg ccaaaattgt ctcgccgtta tagacaaaca   15060
ggcagtatat tttattcagt ctctcttgta ttgtagccat actgtgccct tctccttgtt   15120
ttgtccaata ataatatcta aagctcacct gtttgtcaac aactgttta gatatttaag     15180 ggtgaataa ccaccttct gtattactcg gaaacaggag tccaaatatg gtttgcacga     15240
tcctcaataa gattgagtgc aatctgacgg cccaacccag aacgaacgac atcgtctgga   15300
ctatcaaagc taatcattcc aacctcagga tctggatggc gagtaaagaa atctgtcacc   15360
catgcaaggc cagatttacc agggatgtca cgttggctat tatcacccat aattacaagg   15420
gtggcctgat cagagatcct tgtgataatt gacaacattt cttcagggtt agttgctgt    15480 gcttcatcaa taagtacaaa gcatcgttca tcaaaactac gaccacgaat gctttcaact   15540
tcacaaatct cgatacggct gttctgacca tctcccagca ttgcggcaaa agcacctttg   15600
ccaacacgac gacaaatagt gtccgtcata ctacgaaggt aaggccaaag cttctgcatt   15660
gacgttcccg gtttgtatcc gcttgatttt ccggtctgta cataaggacg tgcaacaatg   15720
atcttatcaa tctcgttctt gcgcagaaga tcacctgcat atgcagatgc catgaatgtc   15780
ttaccggatc caaacacacc gtttacaatg ataatcttac gcgaccctag ataatcaaga   15840 tactttgct gcttttattt cattggtcgg agagctggag cggtgtgctc tcgttcgtca    15900
gcaaattttt cagcagcctt acgcaggcga tcagatttgc gagcctctct agcttcatca   15960
cgcatgcgtt ttgtttcttt agctcgaccc atgttgggac tcctttcaga ttgagatgtg   16020
ccaagtgctt ttactgcaat agtttttcaa tagccgcttc catgctgctt gcaacagcct   16080
gaactcggat attcatctct tcttggtgga tcagctcctt aagctcttta atggtaaatt   16140
ctttagagaa accttccacc ataatcttgt gtaaggcttc ttgcgtgtct acctgcaaga   16200
acttttccag tttgttggca gaggcttcta aatcagcccg aatacgaggg tcatctgtgc   16260
```

```
gattcagcat caggcgtaag ccatcaagat tagtagaaat agcgtctgca tgttgagtaa   16320
ctaaccgtgg caaaatgaga tctacaaact tattagccaa atcgatacgt tcttgtgtca   16380
ctgttgcacc ccctcttcat cctcatgatg tttcttttca cgcttgtgtt ttttcttaag   16440
ctcaagcgca atctcttttt tgtacgcctt cttcaaggcc tttttagcca tttggcacct   16500
cctctgcttt cattacgcta attataacca acttaacaag gctttgtcaa caattagtca   16560
acctgaaccc aaccgcctgc tacctttta aacattcttt ggttatcgct gcctcggaat   16620
ggtttcttgg ttggtaaatc ttttacatac tttccatcaa tgacgatatc agccagttta   16680
agaacatcac tagagatatg ctcaaatgtg aacccagtat acacaagaat agttttcttg   16740
tcaccaaact tttccttaat tctcctcata aggttaataa tacctggcgc attataagta   16800
gccaaaggct ctccaccaag taaagaaata ccgcatacag attcattgtc caagtccgac   16860 aaaatttct gcaaatcttc ttcggtgaac tctcttcctt tatctttga ccaaaatgct   16920 tgattaaagc aaccaggaca agcgtgtggg cacccagata cccacaaagc tgtcctaata   16980
cccggccctt cggtgtaaga tatctctgtg tatccgacaa tattcatacg tactccgcat   17040
cgcatttagg acaatgccaa ataaaatcgt ccagtgcctt acaccaacga agattgcaat   17100
gacaaccgca cttgcaaatt ttataaatac ctgatgacat actgcacctc ctagctcact   17160
gtgtgtcaat aatatgccac atccttgtgg cttttgtcaa gaatcagcaa ccacaacttc   17220
cgtagtgctt aactcgctcg ataacttccg cttgcttacc tttattgtaa ggacgggagt   17280
tagggctgga aagtatcca gacacacgtc gaattacact gatcgttccc tcttcatggt   17340
ttccacaccc tgggcataca aagcctttag ctgttgcact gaactcacca gagaaaccgc   17400
acttgagaca tttatctaca ggttggttaa taccaaaata cataatgtgt ttatatccga   17460
aatcaacaag agcttccaaa gcatctaagt tgtttttcag atttggtgtc tctatgtacc   17520
cgatgttgcc accagaggag atcatagcaa aaccttcctc atactcccac ttatcaaaag   17580
gagagctatt tatccatact ggctgatgga aactgttggt gagatattca tgctcgtgct   17640
tcaacacttc cggatattca cgatccagac aggttgcagc tttatagcat aaactctcag   17700
aaggggtgcc gtacaagcta aatgctagtc cactttcctt cttatatcgc tcacaagcat   17760
ctttcatgtg ctgaaggatt ccaagagcta aagccttgtc accctccctg cccaaaatct   17820
gacaggtttc atacacacca atataccaa tactgatgga agcgtaccct tcatagaaga   17880
gtttatcaat actctcttca ggatccaggc gagcaagagc tccctcacac cacataatag   17940
gattctgccc agccttggtg cctttcaaac gattaactct tacaaggtga gcctcatatg   18000
ccaaatccaa atattcgtca agaactgcaa agaaatcaac accttccgtt ttagcttttg   18060
ccgcaatcat tggtaggtta aggctaacaa cacccaagtt gaatctgcca aggtattct   18120 cctcgcctgt tacagggtcg ctatatttcg ataagaaact tctacacatt atgttcaagg   18180
tggttcgcaa ggccacccc gcacctttac gtgctgctgc atgttcccat gcagatcaga   18240
ctatatcttc acacttagtg tgtctaccat ttcgagtgtc atcagcttac accctacacc   18300
gctacattca tcacggttag tcgttaggca tttcgtaaca gaactcgtaa tcatagttat   18360
taggtgcacc acgtttcagg atagcagata gtctttttct atctattcct aaaacatcag   18420
cacaacatct cagactctta aagtgaataa ccacaccagt taatttgttg gtggctttca   18480
ccccgtgaca tcttgtgtaa aaagcataac agttgttgtc gtatccttct tgagtattgt   18540
ctgggcaagc tccccactca aggttgtata cgctgttatc tttcctgttg tcacctttgt   18600
```

```
gcttaacata tggtaaattg tctggatttg gtaaaaacgc ttcagcaaca agtctgtgaa    18660
cccttaggca aacagtctttt ttgttcttgc gtatcctgac aagacggtaa cctgtgttta    18720
tctcttccca cgaatgaata attctttcat tttcgtatcg ggtgcaataa acattgccca    18780
tctcgtcaat ttcataacct tcaaaatcac gaatttgttt tctcatttca ggactcctct    18840
tagtcaggag ttctgttacg tttagcacgg gattgtccgt tctggagttt ccccgtttag    18900
atagatttta catgagcagt tatagtttac ccatgcttgt tactttgccg tctgttgaac    18960
ctgtcacttt acgatttagc ggaacagaaa caaagtcagg ataaatccgc tctgcagagc    19020
attctaaggc caatcgtttc aaatcatagt taggatcccc agggttcatg ttgacaccct    19080
cctctaagaa gaacagcact ttagggaaca caggtgtgat ccgttcttca ccgagaccca    19140
ttttgtgaac tttcaagtag ttttttggtaa tcattctacc aaagaccgag gtatccagcc    19200
ctaaacttag tgtgatgaat ggagtttgcc cgttgacaga agttaacgta ttgatttggt    19260
agagcaaagt ttgcatacta tcaaacacgt cttttatctgt catttgcatt gcaacagtct    19320
cagcatctgg caaccaatgt tcctgacaaa atttaaggtt cttctcatag gttgcttcag    19380
catactgtgc cagataatga tcaatatggc tcatggtctg accgccatat tgagcactag    19440
ctactgcact agagatttgg ctaaggattg ttgttgcaac ccctattgac ttcggcttac    19500
tgacatgggc gttgccaatg ttgaatccgt tttccagcat atccggataa ttccaccaaac   19560 aacagtttgt taacgggctg atcaagtagt caagatcatg cacatggatg aagcccttgt    19620
tgtgctcttc tgagacacga tctggcagga tctgtgttga tgcaaggtgt ttgctaagga    19680
tgcctgcaag caggtcacga tgagtgtgta catgattagt aggcttattt gcgttttctt    19740
ttgtaaattc atcacaagta cgatccaaga agccactaat atctgcaagc agtttttccac   19800 ctgcctctct gttattatct cttgtctgtc tatactggat gtattctctg gctgcacatt    19860
ttaaacccat atccataaga gcatcttcaa caaggatatg gatattttt acagagatcg     19920 tgcactggtc ggttggcaga ttgttggcaa caacttcatt aaccgcacag gcaatccggt    19980
aagcttcttc ttcagtatgt ccagactcaa gtaaggcgga ctctgccgcc ttgatcacct    20040
taattccgtt ataaaactct tctctaccgt cccgttttac aactttcact ttttctctcc    20100
aaaaccattc ttaacaaaag agatgaaatc gtcagcacca cctatgtgga tactgtcaag    20160 gttgcttttcc aagaagatct gaggcaacgt tctgggaaca aatgggctac acttctcgat    20220
aagctcttct tttgtgtatc cctcacctag cgtcttgtat acgaaaggta tgcctttgct    20280
gactgcaaat tctttttgctc ttacacaatg tgggcagtta tccttgccgt aaatgatgat    20340
gaaaaaagat ttttcgcagc tcatatatta aaactcccaa atttcttctt cagcgtcgtt    20400
aacggttgtg ttgacgcggt agtcggtgtt agacatttcc tggttagccg tctgttgcag    20460
tgaaggtttc atccacacct gcataaacgg tagcgggtct tttgttggcg gcacaaagtc    20520
tttgtcgatg tcgtaataat cataaatcgg tgagcagtta tagtcaaccc attctttaag    20580
caacggtgaa ttaagaccta taatcgctct tccttcgctg aaaatatagt cactccaacc    20640
gtactccttg gtccgcactt cgtcaagaat ttcttttaac tcacccttaa tctcaaggaa    20700
gctttgctcc catgcaggat catcaagcag gatatcgatg atagcaaaat cacctttcga    20760
atgcagcatt tcatcaagca taattttttg aacaagttgt gccacttgaa caaaaatacc    20820
ttgctcagct actgcgaacg tacatgcaaa acttgcaata aactcaatac tttctagagc    20880
taaaagtgca aaaagtgctc taaggataca tttccgtaca acatcttctt caacactgga    20940
aggatccagt cggtattttg caccaataac ctcaagctct tgcatatatt tgacaataac    21000
```

```
tccagatctg ctcagcacgt tctggttttc ctgaatctct tctataatct cacgagcatt   21060
aggaaggcat tgtctaacaa tctctgagta agttagtgca tgaagaacct caatctcaga   21120
ctgcttcatc aacaaggtga aaagctcact attggtgata aatggtgaaa acaggcaaat   21180
gatagatctt gctgcaacac tgtctgcctc ccattgccac atcagtgtct gcaccatcac   21240
atcgtaagtt gactttgagc atgttacgaa atccgaaata gactgtgaca aatctacttc   21300
gtcctctgcc caatcctgtt ctttttgttt tttatatagt tcaaacagtt gtgggtactt   21360
tttgttaata gagtcgtaca tccccatctg ctgtcctaga aacagtggat aatcaccagt   21420
tttatgagca gtgttctcag tattaaatac ggacattatt ctacctctaa aatgggggccg  21480 aagccccttt taaattacag tgcacaactt tcgcaatacg gatcttcaac tgaactatct   21540
gcaatcaaag gatagttctt tctggtttca tcttcagcct gtttcttcgc atgaagctcc   21600
tctgtcaagg agtcaccagc accaacccga gagtttaagt aataccatgt cttcattccg   21660
aatttggtag cacggataag ataccccagc tgctccttca ttgaaatttt accatctttc   21720
aacttggtgt aatcaatata taggtcagca ctgattgcct gtcctgtgaa ttttttgaatc  21780 acagcataca tatcgatcat gtcgttagta tcaacgtccc aagctgaggt ataatactct   21840
ttcagctcat catattcagg aacgataaac agcacctgcc cttgtggcga ctttttaaag   21900
ataatgtgct cacggacagg ataaaccccg ttagttgtgt tgttgccaa cgaagagctt    21960 tcattaggca tatatgcttc aagaacgcta ttacgtagtc caccgttttc aataatttct   22020
ttacgtaacc cttcccaatc ctgcttaaga gaaggatctt tcaccacact atcgacctct   22080
ttgttataag tgtcgattgg taaccaacca tctgggtatt ttgttttatg catccactcg   22140
cagacaccac gctctttttgc caatcgtaaa cttgccttat gcaagctgta gctgtgaagc  22200
tctgcaagat cgtgaacaag ctgtttactt tcaggagacc cgtaagcaac cttgtggctg   22260
gcaataaaat gtgcaatatt ggtaaggcca accccgatgg atctgcgttt tttaacagtg   22320
ctctccatat tttcatacgg atatgtcatg atttccataa cattgtcaat cataagcaca   22380
gtgtagtatg caacatcctc atactcctct ggagtaaccc ttccagctac aagagatgat   22440
aggaagcaca atgcaacctc accatcatca gcatcgtact tgaagatatt acgcatatct   22500
gaatagcctt ttgtcggaag agctatctct gcacacagat tacttgaata gattacatct   22560
ttaaaaggtg tatgtctatt catctcatct gtccagtaca catacagcct gccaacctcg   22620
gtacgctgcg tgatcagttc aacagcaagg tctctagcac ggatccatgt tttaggaatg   22680
ctatcatctt tagcgatacg atcaacctct gcatcaaact cctccataga catggtgaag   22740
ataccctcgt gcagttgagg cgcgtgctta taggaaacaa gcatccaatc taaattctta   22800
gccacacggt tgataaatga cctattaata cctatagagt agtccatagt gttgattctt   22860
tttgaagcaa cagtcatagg gtttctcaaa cggattagct catcaatctg tgggtctagc   22920
gcaagaaatg ataccgttgc cgaacctcca cgtgattgtt gtctattctc cttaacccca   22980
gcatcaatac ctcgataata tggaagctta cccatatgtt taatagtgtt accacgaaca   23040
ccatcacctg cagatcttga tgataaatag tagccaatac ctgcttggtt aaccgtcatt   23100
gtgtacgcaa cttcacgtgc cacaccaata gattttgctg tatcgtcagc ttttattaca   23160
caacaagatg catacccctgt cttacctgtg cgtagaccgt ttaagtacgg tgtcggggca   23220
ttgatcttta agtctgacag ataagtgtat aatttttacaa catcgtcaat acggcgttct   23280
ttcggcatat ttttcatgac agccatcgct atccccataa acatcatctg tggagattca   23340
```

```
aacagggtgt ctttaagagt atccttgatc ccgtatttgt cgcgaaactg tttaaggact    23400
gcatagccat aaccgagatc tttactgtga tcaataacag cgtctaaagt gtttaactcg    23460
gtaaagctat aacccatatc ctcccaatac cctttatcaa ccatggtatt gtaaaatgag    23520
ggtaaggaag ggatctttgt aaatcctcca aaagcctctt tataaatctg accaataaga    23580
acacgaccag ccatgcggga atgtgcttcg tctttacggc taacacagga gtctatgata    23640
gcttggttaa cttcttttgt tgtacatcca tcatacagcc gtttgtatgc atcgagtgca    23700
atatgtgacc aatttccgtt accgtcgtca ccgaaaatag ctgccttatt taaacgttct    23760
ggatcgaatg tcacttcaca tccgttgctt ttaattacct tggtgatcaa tttgcttcct    23820
ccacttcatc aacgtattta tcaaggcagg tatcagtatc ttgttggata aaggtatcct    23880
cttctacgga gatatttata attttacctg tatactcgtc ataataaaca tcatcataca    23940
ttttaatatc gtttgtcaga ccgttgaacc aaagccaacc aacatattct gcccgacttg    24000
caaaaccaag atccttccac ttggagttat gactcatctt caccaccttta gctttcaata    24060 ccgaataatt tttccaggcg atgcagatct tcaaaattga aaggttcatc aacaatatga    24120
atatcttcag cctttttcaga ttgttttgta tactttctta cattaacacg atcctctacg    24180
gggatatcat acggaagatc ttgaacaagc attgcctcac cgggtgcttt atctacatct    24240
aaaatatcta caccgttata catttgcggg tatctaaagt ctgcacgcat gacaccagca    24300
aatacatctg ccttttctata atgtgttggc ttattttttgc atcgaacgtt ttttccacga    24360
agaacatcaa tattttttaa atcaaacccct acagcaaaga gtgcagctcg gagaccgttt    24420
cgtgtgcgaa cgttaaatct gggaacagta gataggaaat ctaaagtaac tgaaataaat    24480 gtcttttttag gaatcataac attactcata tctgtctcca tttctggctc accaacaaag    24540
tgagccatta ttatagacta tctaatacta ttagtcaaca caaagttac ctatcgctgt    24600 gataggatta acctttcatg aagtggttat taagcagctg tctgtgctga acccacccac    24660
aaaagttggc agaccagaat ttaccatcac ggtcttgatg ggttacacct tcctgccaaa    24720
cacagctgtc ctgtgtgatt tcacatgaag acaggtagta gtttaaacgt tccattgcgt    24780
tatcgtgatc cataggtgtt gcctggtgct cgtaagggct tgcatgaata cgatccccac    24840
caatcaattt tttagccaca ctgtctgcct tttcaaacgt gctgtcaata tttcgataag    24900
atacttgtgc acagcaacta gcactaatac acagagcttc tttagtatcg agaatgcaga    24960
gctttccttc tgtgtcacgt acagcgtagt taaactctcc gtccaaataa acatgctcta    25020
catatggggt gtgccattga cccggtttaa ggatttcagg agtgctattc ataatagcat    25080
cctgcatgca attagccaac atctgaatcg taggatccgc atcgtgccag caacgcaggt    25140
ggaaaaaatt attccactcg gtgcttgtta caactgtttt catgcgctga aacggctcta    25200
ctaagcggtt acatacttgc ttatggtaac cagcaagggc gaacttctct gcatgccaag    25260
cggcgttttt tgcagcttct ttccaaaact cttcagggg catctccatg tcagtgtatt    25320
ctacacggat cttttgatcg tgttcccctc catcttccat tcctcgctta tttacaccga    25380
agcgaactgg cattgccgga ttctccacaa tctgctgcag catcttgctg acaggcactg    25440
cacgagaaga catagcgttt cggctgaaca ttcgatgtgt cataagctct gagtgaataa    25500
ttcgaggata ttctagctca aaagtagtga tacgcttacc tttctcggaa atgctgtcgg    25560
caataatctt tgcagtgcac agttttagca ttattttagct ctccttgttt taattttgga    25620
aatttcgtct gggtttatgt tggccttaaa tgcaaggtat ctgttaaaca tatcggagca    25680
catatcttgg gtgatcctag aggcatacac cagcttaccg cccagatcat acacctctat    25740
```

```
ccagtcaccg tatctgacta caggatcgcc acctttagaa catctgccca tttcaaatac   25800
cttctaaaaa cttccctatt ttataccagc tgttagcggt atagtcaaca ctaaccttca   25860
actcctcgaa ttgctcgtaa ggagtgtctt ttaagatttt aataacttca ggacgtgaag   25920
cgaattgatt caggtattca tgcctgtcgt caattataac atctacagcc acattacctt   25980
tgaaatgtgt ggcgtagaag ccgtgaccct gggtgtgatc gtccagatcc ataaaatcgc   26040
tggtccaacg ctttaagaac cttgatttag atgcaaggtg acctttctta catacagaga   26100
taaatgcaag cttgtgacca cgagccacca aatctttcat aacctcaata gcccctctt    26160 caggcttaag aaagtcgtag aggaacgggt cactccagaa atcaaaaggc cctatgatgt   26220
tttctttggg gcgatcaggc caatactttg acagatcgta atacatcagt ccgttagaag   26280
gtttagcgac tgtcttgctg gctgggccat acaaacgctc tagccattcc caccatgctg   26340
ttcctgagtc taccagtgtt aaatctacat caattccgat cagcattgtt ctcagccctc   26400
tttagcatca atatacttgc acacaatctc agatgcgcac tcccaaggag ctccctcggg   26460
gttaacaaca tcaaactcga tacctttat cccgttcttc tctagactaa ggtaagttct     26520
ggaatcattt ccccaatcat atcctgcacg gtggatacgg aacagtagaa gatcgccacc   26580
tgtgctgtat gcgtactcgc caaggcatgc cagctcctct ttgaagccac catcggagta   26640
aacaacaacc cctttacctt cagggaaatc tttcttcaag gatgcgactg cggccttacc   26700
gaaagcatct tcaccaaaga taggtttaat cagattttca ctacaatgga tcatccattc   26760
tcgcggagaa acatgcttgc cgtctatcat taagaacggg cacggttctt ctttgtagcg   26820
gcgatcataa agtgcattcc acaactgggg tgaaatacca gctgccttaa ttgccacact   26880
gaatagcatt tcctttacct cgcggtgatg cgagtttgga atggcttcca acaaaagatc   26940
tgcgatatgg tcttttccag aacttggtgg agcattaaga acaataatat ccattaaaaa   27000
cctccgtggt attcttcaac tgcatcaata atacttttac acttatctac cagctcgtta   27060
gctactacag catcgtcttc ccaaacagcc tcctcaatct gatcaagcag tgatcgcatc   27120
ttcttcatca tttctgggat aaagcttttct gaaaagctgt ctggaattgt taactctggt   27180
gtcattgcgg tctccaatca tactgcacgt tattagaagt ttgttttttac acgtcccttt   27240 tcatccactt cgttgttagc taaaagcgtt acaaagtctg taaaacgaac atgaagaact   27300
cttttcttat ccaggtaccc taaagccaca cctgagaaat ttagcatcaa aggggctaaa   27360
gaagctctag cactgagatg ctgctgttcc actcttccaa caccctttagt ataagaaggg   27420 ttgagattgt aagttctgaa tccaagtttt gttggagctt tagaattaaa acaacttta    27480 taacgtttct tactcagctt atgttccaga ataagcattc cctttttcgcc tcggataagc   27540 tgaaaatctg taaatgctc ttttaagaca aaggtagtg ccagccccat agcctgtccc     27600
ctttgcacgg ctgtttcacc aaaagccttt gcatcagtaa gctctttagt caagtctata   27660
cttttgatca tacctggtct ccaaaatgta ttgtagttct ttcttgccta tactcttcat   27720
tccagcagtc ttacctgctt cttcttgaaa agaagaatag cattcagcaa acactctgtc   27780
aacaccatca actaaagatt ttatgaaata tgttgattct tcagattttg ggtcatcctc   27840
ccccaatact tttccagcat tatacccaac acgccttatg cagaagtcgt agtcatctgg   27900
tgtgctaaaa gaaataacc tattctcccc aatctctaca ggatccctat tgcacacctt    27960
tttctcccaa atttggaaaa cacatggcac gtcataaggt ttgccgttaa gtaaaaacga   28020
gttcttgggg caactttcgc tgtaaataag gtgcatcgac atgtcaagcc tgtttgcaaa   28080
```

-continued

```
aaatatttttt tcaaatgtcc gtggcaagat gaaggctata gccccaccag gctctagcaa   28140
tgatgcacag tggttaaaga acttgcaagc taaagacgaa tttttgccga atggaggatt   28200
gcctatgaag acatcagcct tagggtacac ctctaagaag tttgccttaa tacacggtgt   28260
tgggccttca aactcaggat ctggtaccaa atcgtacgac agtatctctg aaaatagttt   28320
tgaaaagaa cctttttccag cagaaggctc aacgtatgca caattcccat acctaccttt   28380
tactttacca acaagatatt ctgcatactc agggtctgtg taatatttgt cgttggactc   28440
tttcttgctc aaagtgcctc caaaatgaaa agggaggcgc aagcctccct ctacttgtca   28500
gattatctga atcagggtgt ttttcatctc ttctcgggta cggatgttgt tacgatcacg   28560
aacaacagat ccacaacctt cgcagcggta ggttttaaat gcactcagct gagtatacgc   28620
caaagcctct cctcgtgaa ggtgttctcc accacaacgt gggcaacgaa cttttgactc   28680
ctcatcttgg tagtacaacg acatgttggg gtgctgctta gcaaacggac gcgccagcaa   28740
ataggcct tccagagaca agatgtcccc aacattatac tcccgcatct gtttaaacgc   28800
ctcaagatca ccatgaacac acttgatcca catttcaaat gtgtggtcaa ttagtttctg   28860
tcgggccagt tggaagtatt tacatgcata ctctaacgtg tttgcattca aacggaatgc   28920
ctttttaatc atcttgaggg tgtcaacctc tttgtatggg cttgttggcg gcaaaccgtg   28980
aaatgcaaat cgttggttgg cccacccaca gtcaaaacca gagttgtgtg ctactgctac   29040
atcacattta tccagataat accacaaatc ttgaatcagc tcaagatcgt tgtggatatc   29100
ctcgccccac attttgtaat caggaagagc acagtcaacc acactggggc tgtctaacca   29160
tttacctgcg aaagttagca tatagggcat aatttcaata ccgcaggttt gaatgttggg   29220
cttataatgc ccaaagaacc agccgttgt tgggatgtc tctgtatcat acacccaaac   29280
tttagccct ttgtgttctt caaggaagcg ctccgttgcc tctcctacaa tctctgacat   29340
attctcttgt gcacgtttaa gctgtagccg gatccagctc tcacgtgact cacgacctag   29400
aaattcacga gcaatttgtc tattggtgta tccctgttgc tttagtgtta aaatttgctc   29460
aagagttaac tttgtcatca tcgttaagat tccttagtaa aactgaagaa tgtcttttaa   29520
agcgaagtca cgatattcgc ccttgtctac atcaaatgca tgcatcaacc actgatcttc   29580
tttatgataa tctgtagagc caaaccataa actaggctca gtaacgcagc gatctgcaac   29640
aacacctttc cagttacggt atttcatcct gatcagaact gaatcacaag gattgaatac   29700
cttttcgtc tccatagaaa tctctctcct cagttttctt tataaactcc tgcatgtagg   29760
cctcaatagc ctcatgcttg gtgtactctg aattaatgac aagatcgaga tccgattctg   29820
cccgtgcaat aatcgtagct ttagagcatc tcctcaagaa cttgtcata tcgtccctgt   29880
agttttgtg gagcgggaag tcgctatagt ctttctccag atagtcagcc atccggcgca   29940
acgcctctga taactgcaa tctgtatact cgttacagta tttcatccag tatttaagca   30000
cataccctc aaaggtatta gtgcattggg acaaacacc cctgcaatga ccagtcagat   30060
gatcatgatc taaacaaggc ttacgaagtg gttcgcacaa gatcggatca agaccatcct   30120
gctcttctga caattctttc cgaaagttgg ctatatcctt agaatctttt agccacccgt   30180
tatgaacggg ggcttgaca gcttttcttc ttatttacg ctttgcgata atccctccag   30240
atgcgccctg cctatccaat aagcatctgc gagatcggcc ttaccttgta ccaaattgat   30300
cccatctagg aacccaggtt cagatacttc acaggcctta accatcaact ttttatccat   30360
cgtaacaggc ttcttcacag tatgctcttt acccgtcttt ttgtcaagct ttttcttctc   30420
ctcaaaagca agttcttcag gaagatgact acgagcaaac tttttggcag ttgttggtgt   30480
```

```
cactgtgtgg accttaaaca ggccgtcatt ttcacaatct gctaaagcat cccagagcat   30540
aacttcaaga ccgtaaaaca acccagccag ttcacgtgtg gcatctcctc gcgatccaaa   30600
ggagagccct tccatgacca cggtgtcaac gtggtgcgtg tggatataat atctaacctg   30660
tttgcagatc cagtcaatac gctcagcagc tgttgcaaaa gaaaccgtcc ctggtttctt   30720
ctcttttgca gacgagcttt gggttcgtaa cacaacctta tgaacaggcc taccatcgtc   30780
ccatacaacg caggccgtgt gggtaagaga ctggtctata gacagcagtc tttctctcat   30840
actgtttcct cttcatctgg ggcataagct ttgtctttga acaacacaag agagcaaagc   30900
ttaacatctg tttccacact ggtaaacatg cataaccgct caccctcgat cagctcacag   30960
tcctctttta aaacagcaga ccatacacga tcatctgcgt aatcatcagt atacaagatg   31020
tatgcaatag tgtcatcttc atacaaccgc cacatacctg tggcaacaat aaatgtattt   31080
tttgtttta tggtgcctgt tgtatggtca tcctcaaaaa cagcttccat aattgcatta   31140
tctacagagt ttttagtcat caaattgctc caacatttct aagaacatta acaagttttg   31200
tttggtcatt gaatgatcgc ttcatataca aacagtcgaa aattatactc atccactgac   31260
ctacggaaat cctacggtcg ataccattga aatcagtata cttaacgcca cctttcggaa   31320
accattttt atactgatcg atgattgcta accacatctc cttaggtgtg ctgcactgag   31380
acagcaagga gaatgcagat gcatctccaa acttcccttt accaataagc ccttggtaag   31440
gcttaatatt gtcagctgag tcaccacata gcatttgata accgaagaac aacattccat   31500
acccaccaac atctccgttt ggtttcatga atatgttacc cataccgtta tcaataagca   31560
taggagtttc tcttacaaaa tcacctttat cgttcctcat cggatcgaat acaagcccag   31620
gaagtgttcg ctggtcctta tctatagaga taataaactt gttgaactta cctgttttct   31680
ggtagtggtt ccaaccttca aattgctgga tagctaacca gtcgtcagct tcaataccgt   31740
tgatcacctg agcgttatac tgcttttgga gatactgtct tgcatcttca agcaacagtg   31800
gtcgaagagt attgttacgg ttggctttgt atcgttccgg catgggaaga tctagtctga   31860
aattacctgt tcctccaagc actcctacgc accgatcttc aggaatacca agatagttaa   31920
ggactgcatt agctttacac ttaattgtgt gcaagcagtt ctctacagga tcaggggttt   31980
ggatatccaa gacatcgaaa tcttcgcgtg tccacggaat aaactccttg ccagcttttt   32040
tacatgcagc ttcacggttg gtgttctcag ccttaaccaa ccgccaact gcgttcttct   32100
gcctccccca aaactctgtt cgtgtttga acaccttctt acgtccggag ctttatgtg   32160
ttacctcaat tgtccttttt tcacaacttg ctgcagcttg atatgcaacc tgatcgaagt   32220
cataatagac tatagcgtca ggttcaagaa gatcggcaag acaatctatg gactcaataa   32280
gtggatattc tctactcaaa gaccctcctg ttagttattc tgcaagatgg ttggatgctg   32340
taatggaatg catcatcact ttctgcaata agtgactcaa catcccaata ctttcaaaa   32400
aggaacggat tggaaccca atgatgagtt attttcatca aggagtctgg tatcagataa   32460
ccagagatct taattacatc gccaggttga attgtgtttt catgaaggtt gcttgccttc   32520
ttcaggatca tacctttatg attctcgttt gcatacaact ggacaatatc tttatcttca   32580
acaataaaa ttttaagcat atctagttct cctagtttat aaatatctga acgataatat   32640
cagattaata acacttttgt caagactttt tagtcttcct tggggagctt tttgttgatt   32700
ttttcctttt gtggtagatt ccaagtgcag cgttttcttg ggcgcacgtt ttaacagttc   32760
tcagacaaga actttcagct ttaggcaggt ttaactccca ccaaccaagc cagtaaagtt   32820
```

```
ctgattcaga caactgctca gattcagcct tccgatacaa tgattgcata cccctaataa    32880
tatcgtccag aggtgtatcg aatacaaaag ctgtcttatc aaatttctct tttacaggtt    32940
tcttagccat caaggtaacc ctctatccac gaaaagtcag tcttccattc cggaacttta    33000
ctaagttcac gccactctgc aaagcagtct cggtaataag cctctgccat acccttagtg    33060
atcttattca ccttagccag ctgattaact gcctgagcat actttccacg gatatttgct    33120
aacccaggat gcaccgatgt gtgacaatcc gggcacagcg ctatcagtcc aacaagccgg    33180
atcacccctt cctcgaaagt gtaaagttca tgacactcca ctgggtgttt gctgccttta    33240
ccgccacaca cctcacaagt gtagttggct tctctgtagc acttcttacg gatcttatcc    33300
cactcactct tcttcacagc gtttcggagg ttattatacc aagctgtttc tgggatcagt    33360
tgcacaataa gcctgcgttc agacttcatt aaacgtccgt cttccacgta tcctcctcat    33420
tcaaagaaat gggtgcgagg gcaggaacct gcctcaccct gtttcacaag ctcatatagc    33480
tcaccttggc ttgtctcata aaggcaaata cgtttaccat tgtcccgata tacatctaca    33540
aggtacgctg tctcacctgc aaacacgaca ccacagacaa ggcatgctgc catgaacaaa    33600
attgccaaca gaaaatcttt catggttaaa ccctcttgat cactttatga ggtaacaata    33660
ccacgtccat gtggtcatgt caatgatact gttacaatct ttcagcaaga gcctttgcgt    33720
aacacgcttc agcagactct ttggtgtcaa acctgcctag cgttttttcct ctgaaagtta    33780
cttttccattt gcctctatct gcttcaaatc tgacacctct agatttatcc ctccctaaag    33840
gctgtccacg atattccctg acaaacgtgc cactttcaaa agactttga gcagcaaggg    33900
cctcttctaa ggtatcgtat tctcctaggt ctttcttata gtaatgacct accttaccaa    33960
aagcagcata ccttccagtt ctagcatgaa aatatacacc caagtgtcca gtgttagatt    34020
taggtatctt gcgtgccagg catccgtcat ctgccgcctt ttttgcgttt tcttctggtg    34080
ttaacagttg taggttttct atcctgtcat cagcaacacc atcggaatag aaaagtggct    34140
ttatgtgatc aacttcgtac ccttctggaa ttggtccata atgcatctcc cacaccaatc    34200
tatgcctgta gtaatgcact ccgcgataga ttatatccct gtacccgtcc atgttagtac    34260
atccagcctc ctttcccatc agttgaggtt tgttttttgg tggggacttc caaaacaacc    34320
ttccagtgcc tgtatcgtat ctaaagacac tccaccagtc aatcccgtta ctcatctgta    34380
acaactccac ctgccttctt aaagatctcc agcatcttgt ctatactttc tgctcgctga    34440
ttgtacagct ttcagccccc tggcggtggt gggaagcttg cccagcggct gcggcattta    34500
tagatggcct ggtgaatacg gccttcatca atatcatcga gcgccttaca ctcacggatc    34560
agttgcaacg caatcttgtc ctggctggca gggccaaaat ctggtaatcc taactgtttc    34620
atatagtgtt tagcaaactt ctccaaaatc tggtaacgcc cagcagcaga agaggtaagt    34680
ttagcattta gcttaacgta aacacctgga tgcttgctgt aatcgctgaa cagcttgccc    34740
ccgactatga catcgtagcc ccgatccttg gtaggttgtc taccattatc tgtaccttct    34800
gaatatgcga tcatatccaa gaaagctttt cgttgaacat ttttatcaag tttcattttt    34860
catactctcc agttcactca taacgagccc tgatcagcac gtggctaggt tgcacagtgc    34920
atacatcagg gcatatgtag gtgccaattg aaaacactca ttcaattggc taccgttatc    34980
tactaaacat acctaaatta ttccagcacc tcccaagtgt ctgggttaac atttcggacg    35040
cagataccga cagggaattg gtagttgttg tcttctgtcc ttgcttgata tttgaaggtg    35100
acaaacttgc cgatcatttc ctgcatcctg tcatagctac gctcctcgtg cgtacctttc    35160
atcttcattt taacaacaat accttccttg tcaacacaga taagaacacc ttcatcattc    35220
```

```
ttatctttct caacgtcaat aactttcacc tcagcatcgt tgaactttt  ccatttcaat   35280
gcttcagatg ttcgctgacc gtattcgtat ttaccacaga agttacgcat gatagtacct   35340
tcataccctt cggacatgaa tacaccgaca gattcttcgc aatgatcaac tgtgtacgca   35400
agctctgcgt caacaacctt gatatggtca agcatcagag tggtaatggt atcttctaca   35460
tccataagat ccttgcagcg tccagattct gtttctggat cccaccacac cttgtcacta   35520
ggaatatcaa aaatgtgata ctctagatcg tagctacagt acccaccgta acgcaaatca   35580
tcacgaacag gctcaacatc aacaggaata tctaccttgt tgaagttttt gtatgttgat   35640
aagcctgcct taattgcggc atgacggcgt tttttatctg cctcgtagtc tttatcgatc   35700
tcggcctgaa tctcttcctg tgtgcgccac cgtttagcaa gagacactat tttctgcaga   35760
ggcagaccat gaatatagat ctctccgtcg agctgtttaa tcctggtggt gaagtggaaa   35820
gaacgaagtt gctccagaag cttccttga  atagggtagg acttattacc acgggaaata   35880
aatttaggct caccgttttg gaaaacaact agtagacgaa ggccatctaa cttacgcaag   35940
atccagcaag gtaatttaag tgcctttcca cgcttcaggt agtcatgcac cagcatgggt   36000
aaaaggtcaa caccctgctc gcaatcttcc atattttcaa catacccag  acggacttgt   36060
ttttcccact tactgatcgc ttccagctca gcctgttgct cagctgtagt ttcattggca   36120
cgacccacgt tcttaggtgt gcagatcgtc tctttgtatt gcagtttacc atcaagcttg   36180
ccaaactcta cgataacctt atcaccatcc gtgaatactt tccactgttg gtagctgcca   36240
tctttgttca gtgcgtacag tgttgttttg atctgatgca ttactcagcc tcttccttaa   36300
aaatttaaa  catctcttct ttgctcatta ccaaccagtc tcccataaag tcaactaacc   36360
aatccccttg gtacaagacc aggttaccaa acggctcgac aagctcacac atgcgaagaa   36420
tatctctggt tcgaacaggt gacgatgtaa acacacctgt atcaatccac cgttgcagat   36480
cagatactga tgaagagctt ccgtcaaact ggtgtgcttc tacaggttta gcaagattaa   36540
ataacggcat tgcagtcctc cttctctaat aggtctttta tcgggtaaac aagcaggtgc   36600
ggatcgtaat aacttatagt cttattctgc cacactatga acttaattac aactaaattt   36660
accacatctt tatccccatg tagtccaaca cacaaatttg tccatatttt gtggttgaat   36720
actttgctgt cgatgtagat cttagtgtca aacttatcct ctatcctacc tataagttta   36780
accaattctt tcatctgatc accaaacaca gcatcgtttt caagatctct agagtgcttg   36840
tacataactt tctacctcac ttgcatactt tccgaaacaa gtaaagccgg gatcaccccg   36900
gctatgttgt taaatatacc ctgttacatc cttgaagctt gaaggcttca tgatcttacc   36960
tttactgtca aggaatatga taactttatt accgttgtag aattcttcct tagcaacaaa   37020
accttcatat cgaccatcaa agcgtcgctc aagatcttta atctccaact cgatgagttg   37080
ttcagcaggc atatctgcac tggcaccgtg tgaataccgt agatggttga cccgtgcaaa   37140
cttgctgtca ttcgatttga gaaccttacg catcatcccg cacacatcgc cgcgaagctg   37200
gaacagcaaa gctgttgaca actctgctaa gcggtaagca gacgctcttt gcttagaggt   37260
gttttcgca  gcgatcagtg tatcatagaa ctcaccaatc ttgaacttaa cacctcgtgg   37320
attatcaaac aggtttgacc acttttcgtg attgtcatta acaagataag cggcataact   37380
tgtgacaaca tgaagatcgc aggcctcttt tagcaagtga tctccaccat cacctttctc   37440
cagctcttcc aaaacttcat tgaactcttc ctcaatgaag ctaagctgta attcgaatgg   37500
tgtgtatgat ttttttcacct tagctgccac acggttccag ttctccaccc agttggcaga   37560
```

```
ccaaaggtag ttttcaggct gagacagttt ttccaggttg tcgatcagtt tagtattcag   37620
cattaaaggt ctccttttaa agttccataa agttttctac agtttcaata aatactttat   37680
cagagaaagc gtcaacagca ccgttaaacc atacagggat cccgcgatcc tcatattgat   37740
aaaggtcgct acgtgaaatg ccacttccat ctgcactctg cgaatcatac ttgtttacaa   37800
tcagcagttt tgtgccttta caagtagcag gaaacaattc ccagttaaaa ttaataactg   37860
tgttagaaca acctaccagg atcaccatat cattgcttgt gagagatgtc aacaggtcat   37920
acatgtctgt atacttagga gcaacctcac cgaagaacac tacattgggc ttaacccagg   37980
tatacttacc tgtatctacc tccgtgtatc cgatattttt aattcatca ttaccttcag   38040 catcttcgta ggtgatttca ggcaaatacc cgtggacatg taaaatatct tcatgtttta   38100
caccagcacg ctccagcaaa tcatctacat tggtggtaag gttgatcaca cgaccagacc   38160
agcgggaata ccactcagcg atccgaagat gtgcaaggtt aggatcaaca ctgcccagag   38220
ctacacgacg tgcattgtaa aagtcatgca ccttatagta gttcttggca aaggtgtgga   38280
tgttgcacac ctcatcgatg ctgaaattct cccacattgc agtgctacca gatcggaaag   38340
tgggaatacc agattcagcg ctcaaaccag caccggagat aataatcagt cgtcgcataa   38400
gtgtcctcag tagatgtttt gtttaatctc tattccaaac tttttaaacg agtcagctgc   38460
aagcatgaat ttacgagccg ctgatggatt agaagtatgt acgaaaatct tcacgttgtc   38520
aaccacggga ggcttaccga atacaaattt ttcctccaac atggataggc aatcatatcc   38580
ttcgaatact tctcctaagt cgttgtccat atgccactca gaaacgcgtc tgtagagctt   38640
tcccttatcg ttaataaaat ccataaactc ggaggaattc ttcagccaaa cagcgtctgg   38700
gagtccataa tttgacggat ctctcaaatc atccagccac acaatcaact tcttcattgc   38760
atatagtcct cgttgtggaa atagtggtcg agtatctccc tgcgttcctg ctccagtagg   38820
cagttccaca catcttctgt gtaattgcta cgaatgaagt ttaccatgcc gtaaaactct   38880
tcgtcaacac gtttaaagat atcatcatcc caaatcttcc aagctttacc cctcattacg   38940
gccttccgtg ccagatagta tggagacttg atcttcagct gcagatcata agggtagtaa   39000
ggcttacgaa tcatataccc ttcacctctt gtttctgcag ccaattcttt tgcatagctg   39060
aacggaattt cacgcacagt gtgaggacgt tttgcgccaa ggtatttggc aatcccatct   39120
aaagctgctt ctggcagcat tattccagaa tcattatatc tgcaacctat caaatatgcg   39180
ccatgatcat gatcttcctg aacaatatgc ggatctgaag ggtgacaaat ttcaaacatg   39240
aatgtcatgt tttcattgcc cataaccttc ttgataagat ctaaattacc acattgctcc   39300
cggatggttt cctttgtgag gttacaatat ggggaatcaa gagatccggt tgttgagaac   39360
aatagttcac ctttatgaga tgacaccaca ccgaggaatc cgttcttttt ctctaccgcc   39420
gtcacaagct tattgtcagg caggttggtg tgattttctc ccaagttaaa cacttttgtg   39480
aagggccatg ccacaacatt tccttcatta ccgacaacaa tgcctcggca ctccagcaaa   39540 cgagggggaca aatgccacag attgttgtag aatactttc tggcatattt atagatcttt   39600
aatccaagat ctggataata tcgactggtt acaagacctt tgtcaactag atcgtctgca   39660
ttaaaatact tcatcatacg ttcctcattt gtcattttgt tccacaatct tcccacacaa   39720
acagcatcat gtcaacactt gaaatgttca aaagagcacg ctatactatc attaaaatta   39780
aaacggaggg tcgctatgtc taaaatgcta tatatcgtgc gtggtctacc agggtctggc   39840 aaaatcaacac tggcaaatgc gctatcttta gaaggtctat atccacattt tgagaacgac   39900
atgttctggt acgacgatga cggcaattac aactgggatg caagtaaagt aacacttgca   39960
```

```
gcaaaatggt gcaaagataa cgtagaagat atgatgcgta tgggatacga ccgtatcgtg    40020
gtaagtaata cgtttacaaa agaaaaacat gtgcaagaat atggtgacat ggcaatcagt    40080
catgggtata gttataccgt aatcgtggtt gaaaaccgcc acggtaataa aagcattcat    40140
gatgttccag acagggtcgt ggatcgtatg gaacgccagc ttaaaaactg cattaaactt    40200
aaatgaggaa tgtatgaaat actttgtaac aagtgacaca cactttctcc accagcgggt    40260
catggagttt gactcgtgtc aaaaacacag atctcagtat gatcacaatc ttgacagtat    40320
gaatgctgga atcatcaccg agtggaactc tgttgtgtca cctgcagaca ctgtgttcca    40380
cttgggggat attgcgtgca ctaatgataa gaatatcaac aacttacttc cagatattct    40440
aaatatgttg aacggacata ttattcttgt tcgtggcaac catgacacaa ggacgactgt    40500
cagaattatg aaagagttct atcatgaggt tgtagattat tacgagtttc gccacaacaa    40560
gaatttgatc tgtatgagtc attaccagtt tgcaacgtgg aacagaaagc atcacggatc    40620
agtccaactg ttcggtcatg ctcacggaac cacgcaacag ttgtttggca ggcagtttga    40680
tgtcggttgg gatgtgtggg ggagactctt accattagaa gaggcatacc gtattgcaat    40740
gagtcttgct attgacagcg gggagtaatc cctgctattt aaagaaaat tgccacacaa     40800 ggagaatcag gagatatgaa agatgtggat aagctgctat atcttaaagt ccccttgaa     40860 atactgtcta tgtcaaaagt tttgaatgac acaaccgggg aggttgttgt tcttgacttg    40920
tatgacaaga tcgtatactg ctacctgcac aactggtata gcttggagg aaattcacgc     40980 ttcacaccca gcacaaggaa aattgcagca gatgttggga taaagaaaac aaaagcagca    41040
gcgtgcgtta aaactttaga atgtgcagga gtggttgaaa tatccacaca agggagaggt    41100
aaaagatgca cattttccaa agttttgcca ccagaagagg ttattcgaat gtcaacaact    41160
ggttagacca gtgaaaactt aaatatctgt actataagga ttcgtatgtt ttatgtccat    41220
ccaagagcag agggtagtaa ctgtccgtga tacggacact actgtccgtc acgcggacac    41280
atctgcccgt aatacggaca ctaactgtcc gcaatacgga cacataaaga atataactaa    41340
aataactaaa taataaaaaa taaaagatct agtacttatg gtactaaagt acatatactt    41400
aacttatgta gaatatacta gatcctaagt accatgtttt aaatttatta cttactattg    41460
gtagtgtcgg cccttcattg gcactcgcct acgaggggcg agatgccggg cctccatagt    41520
gcacacaatg acaggagtgc atacatgcag gactgttaac atgtgtggga gcgaagcgat    41580
agcgcaggcc aaaggccgag cactaatgtg gaccaccgac gaaagcttgc cagcgccgta    41640
aggagtcggt tgagagcctc ccgcgcgagt ttagttaaag tttatgtgtg gaaacggaca    41700
ggaaggcccc taaatcgcca cacagctgcg taaactatac caagtaaggc aatcgcacca    41760
gtttgataga aaagctcgtt acaaagcgat acagtgagtt tttctataac ttgaaggaga   41820
ggcagttatg agttcacgca agatgaccg cgaaaagatt gcaaaacgtt atcagaatga     41880
agaacagatg gagaaaactt tcaagtggaa gccaggtttc cagcgtaatc attctaacgc    41940
tcgtgatcgt aagcatccgg ataagtggct aacaccgcca aatgatggca tgcaggttgg    42000
tgatgagaag gagctatcgc ctggaaaaga tggcaactac attcgcacta aggacgctgg    42060
tccaaaggat gacagctatc ttgtagataa ggttcttgat ggtattgatg tagatgttga    42120
caccacacgg aacttttttc ttgggtggta tcgcacaggt tttttcgaca tcaaggccat    42180
tcgtcgtgtt tgtgatatta aaagtctgc atatgatgac gactcgttac atcgcaccct    42240
gaggcaatat tcagaaagat atggtcatcc ggttatcact cttgacgatg ttgacgaagt    42300
```

```
gatgtatcat gcagaggttg ttgcaggcag atttggtgat gcatatcttg atatcctttc    42360
tgcaaacgat gaggtaatgt tgaataagat ttactacgaa cgttgaggag agcttaatga    42420
acaatccggt agcaaagaac tgtaataagt tcaacaagtc tgcaattcac actgacagga    42480
aaaagagctg gtcaccggac attgacgagg agcttgagaa ttactttgaa gatctggtta    42540
ccaatgcagg tgaggttgcg attaaagaat acgcagacag gagggataag gccggaatct    42600
gttgacaaaa ataatgttac ctgataagat ctgcaatatg atgtgataca attttaactt    42660
acgaggtcta caggtaatgc tatgtttaag gttaagctcg ttttccgttc catgaatgag    42720
gattatttag aagatgaagg tgaatttcgt gcactagatg atgcaataga ttttgccaac    42780
gacttagctt gtatgaatac gggttatggt ttatgttgtt gggatggtgg tgttcagatt    42840
ggtgatagca agatcttcta cttctaccct gagcccgata acaaacaaat taagtatgtt    42900
ttatttattt gtgctttaca atgaggttgt tttcgtgtat catgatgaat atccaattta    42960
aagatgagtt tgatggcttt atctccggat gctttgaaac agggttcgga gaatgctgag    43020
ttccccttag agggcttgat agtgcaccac acttaaaatg gtaggggcag ccagcacatg    43080
acgatgtgac cccagccaac ctgtaataag gtcgagccaa agcgcggtaa tgggtctctg    43140
gtaacccact tgttgggtct ttctggtcca ggacgctggg caagtcgcag gaataccac     43200 cctgcggcga acttgacaat cagtatttgc cgtgataaaa tccacctatc acgtgataat    43260
ggaggaaaca tggcggatac aactaaaaag cgtcgccgta gaggcagacc tctgaaagag    43320
gagtccaacg ccattcagct agagaagaac attcttgata tgaaggaatc ttttatagcg    43380
atggttccag aagctcacaa agttttaaga gagctgatgt tggatccgaa aaccaagcaa    43440
aatattcgtc aaagcattgc agagtatgtc cttgataagg cagaccgaat gcaggaagaa    43500
tatgatgaga tgtttggtga agaggaagag gtggtagtag aagaggctga aaaaccagca    43560 cctttttatgc catttaccac agagatacag cctgttggca atagttaaaa tatttttcttg   43620 acaaactttg cttaacagtg taatattgta aacatggtct cccaccttt ctggcggctc     43680 aggtgtaaaa gaaagccacc cagtgccctg ttagcttagt ggataaagca gcggccttct    43740
aagccgttga cactggttcg agtccagtac ggggtgccaa gttcttttta atgtagctta    43800
ctttagcaga gtaaatcttc ggcaagtggc ggtaaccact ttaccgatac ctcatagtta    43860
gtggtgagaa cactagctat tttaaaaaga atttaaatat tagtatttag gtgagttaat    43920
tccgtagggg tagcggggca gactgtaaat ctgttatcat tgcgattcgg gtggttcgac    43980
tccatcactc accaccaaat ttatatttt aaatgcataa atcatacaga taatggcatt     44040
gatatttatc gtcgtttata ctagtcacta actgctcgaa aatcagtgtc attatcaata    44100
ttgtttataa aagagggtag ggagcaatgg tgctcaagcg gtcttgaaaa ccgtcccgtt    44160
gaggatgact cgatgatggt tcgattccat tatcctctgc catattgttg accttgtaat    44220
taagcgaaag ccggaagcag aaccggatta tcaaatgtta cagtcgtcat cgccgactag    44280
caacatggtc aacatattgc gctaggtaag ccctttggca agggcgagga tttttaatcc    44340
tgaaaataga cgaggtagtc gttgaataca taggtggttc gattccacca cctagcacct    44400
ttttgctgat gtagcacaag tggtagtgca attgatttgt aatcaatagg ttgcaggttc    44460
gagtcctgct atcagcacca tggccctgta gctggaaggt tcaagcaagc gactcataat    44520
cgccagacgg tggttcaatt ccacccaggg ccaccaaata taaatactc cgcgtagctc     44580 agcttggtag agcgcctgat ttgggatcag gaggtcgagt gttcgaatca ctccgtggag    44640
accactttca gttatacttt aaacatatac aaacaaaagg aaccttaaa atgtatacac     44700
```

```
ttaaaattgt agagcgtgta aatccaaccc ataccgtaga ttttcgtgac gatttcaatc   44760
ctctggctgt aaatcttcga gagtcatatc atgaactcag ctgcgatgca gtggtggtct   44820
tttttgaaga caactctgaa ggggcggtag cttgtgttgt tgatagtgag cagaagtttt   44880
atatttacag agatgtagat gcatacttga tgaatgaaaa tgcagttact gttagaatca   44940
tccaccgagt gcctcgataa gtattagtct cctttagtt agtttcgatc tatttaggtt    45000
actcaatttt aacccgcccc gttagctgta tagctgcggg ttttttcgt ttctggagcc     45060 ttaaaatgat ttcagtttta acatggctga gcaggtatag agggatcata aaaggtttag   45120
tttttgcagc tgcgctaggt acagcttatc ttggggccgt gtattggttt aactctaagc   45180
ttaatgatgc ctaccaagaa ggtgtgtcag caacagagtt aaagtgggaa cggatccttg    45240
atcagcaaca aaagcaggcc gacaaaatta aatgggcca cgcagaggag gttaaaaacc     45300
ttgaaaaatc cctttctgat ctgcaggata aattaaatat ggctgagaag gcaggtaaag   45360
aaaagcagat tatctacctc cagtcacctg aaggcaagaa gtcaacactt cctgatcagc   45420
ttatagatat ttataatgag agtatcaatc aggaggatca atgagagttg ctacactgtt   45480
tattgtgtgc ttgttattat gtgggtgtgc aaccagcgtt gagagagaat ataagattga   45540
ccctcctgat gtaggaaggt tgattgttaa accccagaa ggtgccatga aaccacctgc     45600
taaagctatg cctttgaaga aaggtgcgcc agatgcagtg aattctggca ttatgaggga   45660
taataatctg tcttgtagca atgatagagc taaattgatc atttttgcaag actatattag   45720 aacactgttt ccaaaggaga gaggttaatg tctaagattt acggaccgtg ttctgaaaag   45780
cagaagatga tcctcgaaaa cgatgcagat attttggtaa tcggcggtgc cgcagggtct   45840
ggcaagtcgt tcctcttgca gctgatgcca cttaaaatta ttgatgaccc ccacagctct   45900
gtggttatgt tccgaagaac aaccccacag ttggaaggtg agggtggact atggcctaaa   45960
gcagtagcta tttatagtga tctgcctgaa aacattaagc caaagttcag agagaaggat   46020
cataagttca tttttccacg gtttgatccg aacactggca gtgggatag aagcaaaaag    46080 ggagctgttg taaaatactg ccacatggag tacgtacaag ataagcttaa ccatcaaggg   46140
cttgagtaca ccatggtttg cttcgatgag ggttaatttg tagctctcgt aaaacctccc   46200
taattgcggg gaaatcttta ctattaatac caccaacctg tcatggtaac atgatagagg   46260
cttcgaagag agatcgaagg tatggtaaca gtgtgttaat ttagataatc cgcagcgaag   46320
catccgagag gatgaacgtt caacgactag tcgaaagacg tagaatcaag cgattcgaaa   46380
cgggagggta agcggttgtt gtcgcttata agatatagtc tggtctgcat ggagacatgc   46440
agctgtctga aaatggcggg gcaagactag cgaccttgcc cgaacataaa cgacacaatt   46500
cgaatgggag cagatagact atctaatgtc tcgtctgcga tctcagtcaa agtatccatc   46560
aagaatggtt atcagctgta accccgattc agaacacatg cttgccaaac tggttagatg   46620
gtggttggac gatgaagggt atccagatcc ggaaaaatgc ggtaagaaaa gatattttat   46680
ccgacgcgac ggtgaattta tctggggaga ctctaaagaa gagttgatag agaaatacac   46740
cacagttaac ggactgggtg tggagatcaa gccaagaccg ttgtcattct cgtttatagg   46800
tgcaacaata ttcgataatc ctgtctgcct gagagacaac ccagaatacc ttgctttcct   46860
tgaaggtctg cctgagcttg aaaaagccca gcttcttcat ggcaactggt ttgccaaacc   46920
tgagggtgca aactatttcc aaagatcttt ccttcgtgat gctgatagag tgcccttgg    46980 atcagtatct tgcagagcat gggataaggc aggaaccgag agaacttccg gtaataaatt   47040
```

```
tcctgactttaccgccagcgttaaggtaagtaaagatagtgacggcttttattacctgtc    47100
cggcgattattgtcctgagaacgtggatgacgggaggtattccacaggtctggaaggtaa    47160
gttctgtaaaaaggctggtgaacgagatgtgatcatcaggaaacaggcgcagtttgatgg    47220
tgatgattgtataatcgtattctctgtggaccccggtcaggcaggtaagagtgagttctt    47280
aacctcatccagatccttgctcgccgaagggttcagggttgaagaagaccaatgccttc    47340
caacaaatctaaactgacaaggttctcaccttttgccaatcttgcccaacaagggatggt    47400
gaggattgtaaaatccagttccatcctgatactctggaagcatttctgactgaacttga    47460
aaaattcaacggggaaaggtcaacatttaatagaaaagacgactgggctgactgtgtagc    47520
ttctgcgattaatttcctggagaaagaggaggtagcacttccttgtgtgattccatcaat    47580
ctcatcacctctatgttcaagcgttttatctaagtgttgccaatcttaattagatgtgg    47640
tagaatagagtaatcggagatactagccctctgacacgaggctattttgttatactgtt    47700
ttgagggtaaagcttgtgtccaaaaagaaccgcaggaaacacaacgccacagccaaaac    47760
tgtgaataaatctgggaacgcaggcgcaccaactcataatgttcgtatgagtgagatcgg    47820
ttctggcgcacttcccaaattatggcagaatcacaatctatgatggttgaggaattgcg    47880
ttggcctcagctgattgccacagtggaaactatgaaatgtgattccacagttgctactgc    47940
cttagatacaaaatatgttttcatcacgaaagcatttaatgattttaagatcctttataa    48000
tgttaaaagtgaagactctaagaaagctgcgagcttatagagtattctttgcgtaattt    48060
ggcaaaccagcaaactcttcgagatattgcacgaagtgcagctacctttaatgagtatgg    48120
ttttttcactgtttgagaaagtataccgcagagagaaagaaggtaaatacgccgggatgct    48180
tcttattgataaaattgcattccgacctcaggccagtttgtccagatcagagccgtttgt    48240
cttttgacaagaatagtagaacactgacaggtatttatcaatcacctaatgcatttctaaa    48300
cacgcagaatgcacgctgggctggtcctcttgctgcaatgccttcaaaagctttaatga    48360
gcctgaaattttcatccctgctaaaaagctatgctcatgactctgtcaggaacagaatc    48420
taaccctgcaggtgtgtcaccaatgataggttgctacagatcttccgtgagaaagtctt    48480
gattgaaaaccttgaggtagttggctgctccaaagaccttggtggtgtgcttgagctgaa    48540
aattccttccaatattctgaacaaggccagcattgacccgaattcaatggaagggagaat    48600
ggttgcagatcttatgcttgacgcagcaaatgcccatagcggggagcaaagtttctttat    48660
acttccgtctgatagagatagtctggtaaagagctttacttccatgacccctgaagggggt    48720
tgacggcatggtaagcagtattccactaaagatttgattgatgcccgtaagaaggcgat    48780
tcttgaccgttcggtgctggctttattaacctcggtaacgataacgttgatctttctc    48840
gctgtctgagtcaaaacaatctatccatggtcattttgttcagcgtgatatagatattat    48900
cactgaggccttcaataaagatcttattccacagcttctggcattgaatggtatcatcct    48960
tgaagatgatgatatgcctaaactgaaaacctggtctgattgaagaagtggacatggagag    49020
cttctccaagtttgtccagaggatcggtgctgtaggttacttgccaaaaactcctgcagt    49080
aattaataagattcttgaagtaggcgggttgatgaaagatttgacgaggacatggatca    49140
ggaagagctaatgaagctctgggccaggacatcagtagagctggtgatgaatggctgc    49200
aggatccactggcaacggcacttctaagatgtcatcaaccagagataactccatatctaa    49260
catggaaaattaaaaattatcaacacagggggttgcaaaacctccttggcgtgataaaa    49320
taatccacatgggaataagatgccacaggaagaaatgatttcctacgaaatcatctacg    49380
aacctgacactaaagatgctcacggcgagtggatgagtaaagacaccatcaaaaaggcta    49440
```

```
aagataactg ggacgcagca tacgccgcag gcctagtttc tgaaaacctt tttcacttga    49500
cctctacaga tgctttcacc attgaaaaga cgtggattca agaagagttt gatgttgtag    49560
tgattggcac tgagcaggtc atcaaggctg gctcttgggt tgctaaagtt aaatacaata    49620
atcctgaatt atgggaagct aagaaggctg gcattgttgg tggcctaagc attcaggcaa    49680
caggtaatgt tgatgaagag actggtgaaa ttaccaacgt aaacttcggg atcagtgttg    49740
tagaagaggg caatgaataa tgtctgaaaa aacgattact attaaagaga aggggattgc    49800
cctgtgccat aaggctcaag gctatagcgc taacaacaga cctgtatctc ttttgatgaa    49860
gagtgatctt cagcctgagc agttaacaga cgatattgtt aaggcacttc gccaagttac    49920
tgtggagctt agttttgaag aatacctgcg tcgtttcttc gatatgtggt atgatgatgc    49980
caaagcactt gcacacatgc ttggttttga gattgaagag gaggcttggg ctaaagcagca    50040 tcctgattgg gaatgggcgc aagctgacgc agagtcttgt attgcatggc tggaagagcg    50100
ttgtgataac gtgaccattc ataaagctgc aaaagaaggt aagcagctta gtgtggtaga    50160
tcagtacagc ctgttaaaaa cacaacagat ttttgaacaa gtaaccgctg atctcttcga    50220
taaagaaggg aacctgatca aggcggtaca ggaacctact gaggtagata aaactaccga    50280
ggtggatgat gttgcaaaat ccgcaaatac cgaggagaat ccggtggacg taaccaaaac    50340
taaagagtat ctggatctgc tgaagcaagt agaagagctg aaagcaaccc agagtaaagc    50400
tgaagaaatc atcaaggccc aggttgaagt tgaaaaagct aaaatgctga ctaaagctca    50460
agctttaagc tttgttggtg aagaagatca tgcaaccctg gttgacttca tgctggaaaa    50520
agctaacgaa cctattgtag ctatgctgga gaaagctcaa gccaaaattg aagagctgga    50580
agcagaggtg cataaaacca aagaagagtt tgccaccact gaacatggta atgatggcga    50640
acctgttgtg gatgatattg caaaatccgc agaagaaatt cttgctgaaa acgttgcaaa    50700
agcacttgct cgtgcacgtg cagaatctac caaataagac attaacgggg gaaataaatg    50760
attaccgctc aatattctga tatcgtgctc ggcaaagttg attctagcga tgctggctac    50820
aattttaaag agatggaaat tacactgaca gagcaccatc atgctggtac tgttgtaaca    50880
aaaactggca ctatcgctaa cgataatggc tcagatgttt atggtgttct tgtagaccga    50940
gctctggtaa aagatgcagg aaaagttcat ctcgctgagc ctctgcaaac aggtcagaaa    51000
tataaactgg ttgttgcagt tcacggtgtt acctttgcaa aagataagct gctggggtct    51060
aacggtgaag cagctaagca ggctgttctt gaaaagctgg aagctctggg taacaaagtt    51120
cacgtccaga ctcttggtga agagtaagcc ctaaattgtt cgggaaaata tttaagtttt    51180
actttggaga aataaatgat tactcgtaaa gatgaatttg gcattgttga tttaggtgct    51240
actctggacc ttgttccgcg tcaatttcgc ctgatcaccg gtatggatct gttcgaaact    51300
cgtctcggca cctcaacaat tgctcagatt gagcgtgttg atgaagttgt aaccgacatt    51360
ccggcacgcc gtcgtggtgg tgagcgtaac tacgttggta atgaacgcgc tcaggttaaa    51420
aacctgaaca tcccgttctt ccctctggac aaaggcatca ccgccgcaga tgttcagaac    51480
ttccgtcgtt acttcactcc tgatgctccg aaaactgttc aggatgtagt aacccgcgtt    51540
gttcgccgta tccgtgtttc tcatgaagca ctgcgtgaga agcgctgtt ccaggctatc    51600 ctgggtaaat cctatgcacc tggtgacacc acctgtcagt atgactacta cactctgtgg    51660
ggtgtgtctc agaagtctgt tgagattgac cctgcaaaag cagatcagga tcctatggag    51720
gttctggaag aagctcgtct gcacatcgca ctgcaagctg gtgataacgc agctggctat    51780
```

```
cgcatcgtag cactgtgctc accggagttc ttcagtgctg ttactcatca cccgctggta    51840
gaactggcat atacctatta cggctctgct caggaacctc tgcgtcgccg tctgggtgct    51900
ggcggtcagg acagcgtata ccgtgtgttt gaacataaag gtatcacctt tatcgaagat    51960
atctctggca atattcctaa gaaagaagct cgcattctgc cgatgggtat cgatcagatg    52020
ttccagctgc actttgctcc agcagacgat gttaacgaag caaacactcc agcacaggaa    52080
ctgtacatgt ggtacaaaca ctctgcatac ctgcgtgaag agaagattga atctgaaact    52140
tccatgctgg cagttaacac ccgtccagag ctggttgtta aagcaactct gaaaagtgaa    52200
taatcactaa ggtgattcat cccatatggg gaggggttc tcccctcccc tttttattta    52260
ttagggttta acaggagtgt cccgtgaaga gagccgtata tccagttgag tatgatcctc    52320
tattaagagt tttcaacaat cagttaagtt tctatcaatt tttagcacaa tataacccag    52380
aaatcaatgt tggtttatca gccctgctgc caccaacaga atttgttatt ggcagtgttc    52440
actatccatg cagaactatt gtagacttct tcgagaagat tgcaaaacat acaggcctgc    52500
caattgatac tggtatttca actatccgta tgggtgttat tcttctgttc ttcacagaga    52560
accttgatga aagcactta acactgcaaa gcggggatgt caatattaca ctcactccgt    52620
cagtgtttaa agaggtagat gctgctttca aagtttccgt ggcagaagga catctgtggg    52680
accctgcagg gatgcctaaa aaagttacca taaacgatga gcaatgcagc attgtttatg    52740
aggaagatac ccaaactttc accatcaaat ggcctaagaa acgctctcag gttgtaaatc    52800
ttggactgac ctctacagtg gctccagagc ctgaacctga agtgccggaa ccacctcttg    52860
agggtgacag tgaaggtcct gtagcagatc cacaagatgt ggctgtagcc tctttcgcat    52920
ctgcagctgt tgagaataag gatgaaatcc ttaaacaggc cgcagctctt aacaacgaag    52980
atgacaaaag tggttcaaaa gatgcactcc aaacctttgc taaagagtac ggtgttacct    53040
taagtaaggc aaaaactttc caaaatatga tgaaagattt tgaggctgca ctggcataat    53100
tttgttaagg ccccttccaa atcaggaatg gggctttatt tttacgaggt attttcaaat    53160
ggcatggtat gaagatgaag agattatccc gtccccgcct aaccaggatg gtgtagtcga    53220
taccccagaa gaaccaccaa agaagatcc tgtacctccg gaacctgatc cagaccaacc    53280
tcttattgat attatgaggt tattgcttgg caatgttgat gaggaaacac ttcctgatga    53340
ggtaattaaa acattccttg acatggagaa gctgaaacta aattatccgg cagatcctga    53400
taagctacct ctgcttaaat acaatgttct tgtgcagctt gtgcggtggc tgatgatgca    53460
ggaagtgtcc agcggtaatg caagtataac ttctcgtctg gaaaaaatag gtgatgagac    53520
catagagatt cgtggcgggt cttcttacgc ccagtggaaa gatttccttg attggctgct    53580
ggcacatccg gattatgtag actctgagct agacgcttac agcagaatga ttatcatcgg    53640
tggtgttcgt gtagacgaag gtattcgggt taaatttaat gaaaacagta acggcccgtt    53700
cgatgttcag ggaattacac ctatcagtgg tctaaataat caacctcctc gccacccaag    53760
acgcaaacgc agttttaaa aattgttgct tttgatgtat ctttgtggta aaatacatta    53820
gtgaggaata taatgctaaa ggttaaatgt caaaccaggt tcaacctaaa gcgtttagat    53880
cgcttttaca aagaccttgt gaaactcgaa agcaaaacaa taacctacgg cttttatgat    53940
gaacctcacc cgtcaggctt aaatatggca acattggcag ctattcacaa cttcggttgg    54000
aacgggctgc ctgttcgcaa tttcatggag acggcctttg catttcacag cacgcaactg    54060
cagaccttga cagaaaaatt gttgagagtt atggctagag gatcaagtgc agaggctgtt    54120
cttaagcaga tgggggacac aggggccaaa gctatccagt ttgttattga ggctgggcag    54180
```

```
tttagtaacc ctactgttag tgagcagtgg gcacaagaga agggcttcaa cgaggctatg   54240
cggcattacg atgtgctgct ggaatctgca acctttaaaa ttggacagca aaaataaggg   54300
ggttgagtgg cagcaggtta tagactgata ggaaagaaca ggctaatacc ccgtaaaaca   54360
ttcaaaggtc gccacagagt gtataacaaa acagttggtg gtccttttgc taacgagggg   54420
ttagaacttg agtatgaaga gtttgatgtc ttagagtgtg ttgtgcagcc gttgacagga   54480
agggcagcta aagattactc ctctcaaata aatcccgaag gtgacagaca gtacgaggct   54540
tttacagttt actcctcaac caagttgtat agtccagatg aaggaacata tgcaatggct   54600
gatcaaattc agctgcctga catccgtggt gacttgaaat ggtttaccgt tttaaaatgc   54660
gatgcatatg taacgtctgg tggtggaaga tatagatttt ttgtggtaga agagcctgaa   54720
ggagaagact gatggaagct ttcgaaaaag ttttttctga tcttgaaaca accattgcta   54780
agcttgtcaa ggttgccaca ggaagaactg tagttctggc agaaagctct accataccga   54840
agccggaagg tgagtttgta cttttacaaa ccttggcgat caatcccacc acttgggaag   54900
ataatgagtt tcaagatgcg gagggtaatg cttacgtaac acacagttac actgttacct   54960
atctgttaac agcttatcgt ggcagggcac atgctgcact tagcagagta ttgcaagcaa   55020
taaatcttcc aatgttttat gacaagtatt tccctctggg atcgtgcttt gcctactcta   55080
acaattcaac aatctcacct caaagagtgc cgttgaataa gcagacgtat gaaaataggg   55140
ccacggtaat gctgacattt aacgtaaggt ttgttgagac agacattggg gcttttgagg   55200
atcttcaggg aattaaggct gaaataacca cacacttccc ttcacccaat tctgataaat   55260
cggttacaga cagtggtcag taatcgttat aattgtgtag tgtaatgatt acactgcgtg   55320
tttgatatcc gtgcacagat attaagagga acaaatgcc atatttagat aaagtggtag   55380
atgttacagt taacctcgga acccagccta ttgacactgt aggtttcgaa accccgctgt   55440
tcatcgctat ccacaacaac tttactgaga gagctcgcgt atatgctgag ctggatcaga   55500
tggtggaaga cggtttcgca caaggctctg cagcgtatga gtttgcagca aaagctttcg   55560
gcggtgtatt ccctccacag tatgttatga tcggcagaca ggcaaaagaa aaaaccactg   55620
tagattttaa aggtattgct gccgcagctg ataccgatgt cgtaatgact attgcaaaag   55680
gtagctacaa tacttctctg atagtgccta tctctggtgg aacaggtgca actcagattg   55740
cagagtcaat gaagactaaa attgaagcag atgatagctt gaacgatatc actgtagcgg   55800
ctgaagacgg tgttctcacc atcacgggtg actgtactgt tggttatcat actggtaact   55860
atacaatcaa aaatatcgca aatgctgaaa aaccttctac agtagttgat aagatcaatg   55920
ctgagcgtga caattggtac ttcctgtgcc atgaagacca caccgacatt gaagcatgtg   55980
cgaagtgggc tcaggctaac tacaagctgc atgtctactc tactgcagaa gatgttactg   56040
gtaaagataa taacatcgcc accaaactaa tggctgcaca atatgacagt gttggcatgt   56100
acgatcctcg tgctgataaa gattttccag agggtggtat cgtaggcgct atggcatcca   56160
acgatccgtc ttacggtgac agcttgcatt taaaacagat gccaggtgtg attgcaccgt   56220
ctctgacttt aactcagcgt atggctattt gggaaaacca cgttaacttc tacagaatga   56280
ttaacggtgt tggcgctttc tgggaaggta agtgtgcttc aggtcagtat gcagacgcta   56340
ttcgttttgc acactggatc aagttcagat ctgaagaatc tatgtttggg tacatgcatc   56400
gtcgctccaa catgggtttta agcatgaaga tgtctgatga tgatcttccg gttatcaagt   56460
ctgtcctgat gaacaacccg atcaacactg gcattaagaa tggcgcgatc ctgacaggtt   56520
```

```
ttgacgaaga caacaatgtg ttctacgacc cgatcatcac agttcctaaa cgtgcagaga    56580
tcccaaccaa tcagctggct gctcgtgttc tggaaggtgt gaaagtagaa ctggtgtata    56640
acaacgccct gcacttcgtt cgtatccgga tcaacgtcct cctggacaaa gttggttcta    56700
aatccaccaa tgctgttgca atgactgaat aaggaagact agatggaaac tcaaattta    56760 actccttatg cgtatgaccc taaaaaggtc aaactgtatc tgatgcagca gcgtgtcact    56820
ggcttcgctg ctgacaccaa gatcgttgtt tcaagaaacg aagacaacat ctaccctcac    56880
gttggtgtgg atggtgaaat gtctgcggca ctgtctcgta accaatctgg tgttatgact    56940
gtatccttgc agaacacttc tgtatggaac gcttaccttt ctgactggca gaaacaggca    57000
tcgattactg gtctggtatt cttcccggtt ctgctggaag gtagccaagg ccctggtatt    57060
tctacaatcg gttggatcca gaaacagcct gacctgactt acggaaccga agtaggtcag    57120
ttggactggg atatcggtat tctggatgca tggctcaacc gtgacaacat cactggtgct    57180
ctcactggcc tcgcaggtct tgcaggtatt atctaagggc acactctagc ataggcctca    57240
ccttcgggtg gggcttttg cttttagggt tttgacacac gttcttgaat tgcttgaaag    57300
gttaaattga caatgcacca taatcatggt aaaatacaca aatatggtgc acaacatgac    57360
taataaggat gctataaaat ggctataaac tttagaccta caacagagat tgatttagca    57420
gggcacaact ttgtgatcac ccactggggt ccgatgaaag caatgaaaaa catgcctaaa    57480
atcggtaaga ttgtagctgt cccgctaggt gctatcggtg gatctattct ctcaggcggt    57540
cagaatatgg cagaggtcct tcctacagcc ctggcttacc tgttccaaga acttgatgat    57600
aactctattg aagagttatt taaaatcttg ttcgaagata ttaccgtgga tggtgtggat    57660
aggcttaacc ctgatgttgt gttttgcaggg catctgctgg agatgattaa gctggcaggt    57720
aaggttctgg aggttaacta cggctgtttt ttcacacaag acggtttagg aagccttctg    57780
gagatgttac agcagatggg tatgatccag caggtgaaca atctggatca gactccggaa    57840
gagcaggaat aagcaaggtt gttgtgaggg ccagtgagtg ggcagccaag aacagttcac    57900
ttaactggtt cgactttctt tggtgcaggg tgctcaagaa tttcaaaggg gaaaattttg    57960
aatcgctaaa tcttgcagat atggcgtatt tcctgaagct ctgtgagtat cttgatatcg    58020
aagaattcct agataccgtc caaaacaggg aaatggagcg ggagcagaag gctgccgcag    58080
ctgctgcgaa agctaagcgc aggagaggat aatctaaggg ccggattcct tttctgggat    58140
ctggcccttt ttattatgag gaaagcatgg ctacaaacaa aatagttgcc acaacagtca    58200
acaagattgg ctttgagata gagaactcct cctacaaaaa agctgtagag aaaattcgca    58260
gtattgggag ggagttcagg aaacttggcg aggattttaa ctcagccaac ccaatgagta    58320
gatggcaggc agtggctgtt aaaacccagc aaacaatgca acgggttgcc agacagcaat    58380
ctcaggcaaa tgctaaactg cacagggaga gcgtagcaca agccaagaaa gaggctgcag    58440
taagggccgc aatagaacgt agggagaacg cgagacgtaa acaagctgta ggcaatctta    58500
ccgctaaaaa tccagaaatg gctaggatgc gtaagttcta ccagcagcaa gctaaagagg    58560
ccaaaaaggc tgccaaatct acaccagtgt cttacggcgg ttataaggca cctaaggcaa    58620
gagttttggc taatgccaaa tctttcaagt atatccctgg taaccctaat atgggtggtg    58680
tggcttccga ccctaacctt gtgaaagctc agacagccgc tatgaatcgt tatcatagac    58740
agctaagaag ggacagtaaa gctggcatgg ataataggct tatgtcggat cgtgaggcaa    58800
ggagaaccca cctctacaac tctgcgataa gactttctgc caagtatgga gccggattcc    58860
gtggaagctt gcccggatac tcagagttag agtccaggtt tgctcgcggg gagatgaaaa    58920
```

```
agtcaacctt taacgcccac ctgtcagctc tgcagtctgg atttaaaagc gccaccagcc    58980
aaacgcttac acttggtgat gccatgagag acttacgtag gtctgttatt aatgcaacag    59040
ctgcgtatac ggcttttctct ggatttactg ctgtgaacag atctggtcac atgatggagg   59100
gtgcaagtgc tgctcttact gctgttactg agatccaaa caaagccaac agtgaggttg     59160
cgtttgtcca gcaagaggct atgcgtcttg gttttgatct caaatctggt cttcaaggtt    59220
acgcccagat gtcggtaaac gccaaaaacc agatgacaaa tcaggaagtg catgagctgt    59280
tttctgcata ctcccagtat gctgctgctt atggtgccga tgaggtaaaa taccagcgtg    59340
gtatcatggc aatccagcaa atgctcggga aggacaggt aatgtccgaa gaactgaagc     59400
aacaacttgc tgaagcattg cctggtgcat atgaaccttt tatcaaggcc accaaagagg    59460
cttttggtct ttctgaacta tccatggatc agttcatgga catgatgaag aaaggtgagg    59520
ttaagacagc caagatcatg aagtatgtgg ctaagtacat gaacgaggca tctgcagctg    59580
gttatgaaag aatgcagaag tctaacgtac tggcagaaaa cagactgaaa accttcatcg    59640
aactatctcg tcagaagctg ttcacccgtt gggctgatga attaacagag ttctattata    59700
cactgattcg cacaggtgag actttgcaat ttgtgtggga tgcctctggt gattttgtta    59760
gcgggtttgt gagaggcctc aactgggtag ttggtgaact aaacaatacc atagtcaaga    59820
tccgcatgtt tttccttgag tgggggatta aatggggatt cataacagct aagacgaagg    59880
aatattctga agagcttcat gacaccttta gctatgctaa atgggcaggg tttgctgctg    59940
ccatcatgct ggtagtgaac gccctgacaa aaggttttgt catggcatct atgcttgtaa    60000
aaaccttcaa attccttagc tctataagag gtgcagctgg agcagcagca gcgggtgcag    60060
ctaccacaga aggatctggt gggggtgcag caggaaaagg gggaggtggc ctcaagacac    60120
ctggtggtaa agttggcctg cttggtaagc ttggtattat cggtacaata ttaagtgccg    60180
gggagttatt taatgaccgt ttcaacccac tgagtgagag aaatcagcaa ctggatacta    60240
tcagcgatat gattcgcaaa gatatcatat cgggaggtaa cgggtttgtt gatcctttgg    60300 atacctacc gggcggtact cttccgttgc caggtggccc tggttttgct tctcaattaa     60360
gaactatgga aatgctacct ttagagatca gtgatggcaa aatcacgatt tcaatagatg    60420
agggtgagtt tagcaaaata cttgatgcaa aacttgagtg ggagaataac aaagatatta    60480
actttatgtc aacagatctt tggtaataaa cagcacacag ggggctccgg ccccctttat    60540
tttatcggtg ttgtaaaaac ggctattta tgatacaata tttagatggt atcggagtgt     60600
cctggagagg ttatgccaag caatatagtt gatgaaaaag acctgtacaa gcctcaagag    60660
gttaaatctc caaaggctga aaaggcagag caacaaactg aaagcgatgt aaaatacact    60720
atgtttgtca gcggtcttaa ctatggtggt cgcaatacgg agatgaaggg taaaaacttt    60780
actaacgatc ttgccatcat cttcgatcag attgagaatt actctttcaa acattctgtt    60840
gataagactg attttgcggt ggaagataaa tctaccctgt cagaccacgc tgtaattaaa    60900
gatggtgtat tttcttttac tggtagggta aatacatcac cacatataat ctatgagcaa    60960
aactacattg acaggaatac tgactctaaa aaccctgcag catctatgcg accgggcgct    61020
gcactggagg ctttaactga gatcattaat aagcgccaat tggtttcttt ggttaccgag    61080
gagagactcc ttgagaacta catcataacc agcctttctg ccaacaagtc tgttggggaa    61140
ggtgctgcga tggtgtttga tgtagaactt acagagttcc gcacattcta cttgaacaag    61200
gttgttaatg caactgtata cagcaaccct aagaaagtgg gcaagaccca gcaaaaaggt    61260
```

```
gctgtcaacg actgtaagaa tggtagtaac gtaggtaaca agagggacac aggggcattt   61320
gcagacaccg catccacaaa tgccgcagaa gagtggcagc catacaaatc tatgatgtgg   61380
acagatgaaa acggtgttac ccaatctgct gcggattggt attatcagga atatggaaga   61440
ccttctacca tagtcccatc tgagcaggga aactacaaca aagttaacgg aaaataaggg   61500
agcgtgtaat ggagcttaaa gattggtgca taatcacctt tgtgtgggac attgacggct   61560
ttcctgatca aaccatgcgt gttgttttag acaatgagac gtatgaaatg cgtatgcaat   61620
ggaatgagag ggatgagtca tggtggttat ctcttggtcc agtaggtgac agccctttag   61680
taaccagaaa agtaacagct tgtcaagata ttctggacgg actgcattac agagacgatt   61740
taccgaaagg tagattgatg gtgctgtcgt ttaaagacga tcaatattgg ggacgggttg   61800
gaagatacaa ccttggagca agatctgagc tgcaacttgt atacggtacc ccagttgatc   61860
tttacaagga acagcaaggg ttagaataat ggcagagtac agacgtagaa catggcgact   61920
gttgtttggt cgtcctgtag agcatggcgg taaatcaaaa accaatatcc caaaatctgt   61980
tgaaaagaaa ggagagagtg attccggagt ttatgagatt agctcggaca ctggtgctgc   62040
caatatagag tttgacatac aaaaggacaa taccaaagag ccaaacaaag gctatgtgac   62100
agtttacaac ctgtctgacg atacagttaa ctatctagat atgcatcaag ctgatgctct   62160
tgcagttatg tttgaggctg gctatgataa tgagaaccag ttgatattct ctggaactgt   62220
agagtttgtt gaggacagat gggaaggccc gaccagaaaa actaagttca tatttggtga   62280
tggcactgag aacatcatta agtgccaaag cacaagatct tatcagaaag gtacacctct   62340
gaactctgtg cttaatgacc tgctgaagga tatgaacttg ccaaaaggta gggttgttgg   62400
ttttggaaac cagactctac aatactccat ggctttctct ggaaacactg cagagaacct   62460
ccgcaggttt gcaaggctga caaactcaac attcagcgtt caggacggtg ctttatattg   62520
gaccaaggtt ggaaaaaggt tcaaggactc tgtgtttgaa ataagtgcag agtctgggat   62580
gcacggatca cctaccccta aaacccagaa acctgctaaa aaacgaaaag ctaaagctgc   62640
tgcgaaaggt ggcacaagta agaaaaagaa aaacccgaga gaggatgttg gtcttactgt   62700
aacaacatgc cttaacggag ctatcctccc agagtccacc atttatctta aaagcaggca   62760
atacacaggc ttctacaagg tgatcacggt gcatcacaag ggaaccatag aaggcggtga   62820
ttacactaca gagcttggcc ttggggaaac aataggtgga gttgttgaca aaactgagga   62880
ggtataatgg caataaatag gaaagatgct gccgtaagat cctttataga aaaaataatg   62940
agggactacc acaccagtat cagggctaga gttgtcagcg tagattacag tatcccttcc   63000
gcagccgtgc agccaatagc tgaaaccacg tttgatgacg gagatgttga gagatacoct   63060 cttatctatg atgtgccaat ccaggtgatg tctgcaaaca gtgggaaggc aaggttaaca   63120
ctccctatta aggctggaga tgttgtaggg ttgcagtttt cagagagaaa tgaaaacaat   63180
aacgatgatc aacaaactca cggcctgttt ccggggtggg caataacctc tgttcattca   63240
gactctaacg ctctgcagat cgatcctgat aatgtagagt tatggaatga tagggtttat   63300
tttaagctga caccttctgg tgattttgag cttcaaacac ctggtgggac attacggtgc   63360
gacagtagcg gggagttttc tttcaccaac ggagctgcca atttacgagc tgctgtggat   63420
ggaaatatta gaatgaatgg tgccacaata gacccatctg gtagaatcat aactgctgct   63480
ggtgtggatt tggactcatt ctatgcagaa tataaaggtc ataccactc ttgccctgat   63540 ggtgagacaa gtgaccgca ctaatagagg gcttgcatgg ctacgcttta tagtgatata   63600
ttgatggacc cacagacagg tgatttggcg atagacaaag gtcttgagtt gatagactca   63660
```

```
aaccaagtaa gtctgcgcca gcgcctgtgg atgaggttta ataccctggaa agggagctgg    63720 tactttgacg agttgtttgg cttcccttat atggactttc tcagtaagaa ggtcatgaag    63780
actgttcttg ataacaagat tatggaagtg gcaagacaag agccggatgt gctaaacatc    63840
ataaacttcc aatctaccat ggatcgaaga tcgagaacat atcaagcgtt ctttgaggtt    63900
gttaccaagg agaacgagat tgtaagactt gctttcgtag tcttgatca gtttacctat    63960 ccacaacctg attctgggac aacctctcta tgtgatgatg aaggttggat taagcgggct    64020
aataaactgt attacctgat caacttcaga ttgcctagaa ccggggatgc cacatggtgg    64080
aaccagtatg ctggtcctga gatggaaaac ccgatccctg taggctctct gttgactcag    64140
gataaagatc tgctgatgac tgaggcagaa caaaccatta accgcaatac ctggacgctt    64200
gctccagatg agcgcgaata ctctggtgtt attgctacct ccaatgatga ggctattgcc    64260
aaccagtctg gtcgtgctat tgatgttaac taaggagaaa tcatggctgt agcttatcct    64320
acaataccaa ttccagatct tgaagatgca gaaacagtcc tgagtgatga cttcttggtt    64380
gtcaaccaga ctgatgggac aagaaaggct aagattgacg atgttgtcaa cgatcttagc    64440
attactaaga tagtctatt cacagagggt ggttatctta agagcaagaa ggactttgct    64500
tatgacccag agaccaagcg ctactacacg tggaacgggg attatcctaa aataatcctc    64560
ccagactcta ctgtagaggg tgctgggggt gtgtctgcaa aagcctggtc tgttttttgga    64620 gagcttgctg caacttcttc tggtagaata gttgattacg ggtctattgg tggtcagctt    64680
gatatggatc ttgaagttgc tgacactttt aaagttcgac taacttcaaa taccacgatc    64740
tcttttgaaa atcagacaga aggtcttgaa ggggtagcga gaactataac cgtatgcatt    64800
actcagacct ctggcggcaa caaagtctat tggcctgata atgttaaatg ggcatacgga    64860
agagatccta tcctaacatt tacagctggt gcaacagata tttcaagtt agaaacctat    64920 gacaacgggt taacttggta cggggcactg attatcgcag gagctatcta agatgcgtat    64980
tcaacacaac attgataacg tatttcagat gattgagggg cacaggaagt gcctcgataa    65040
taacacaggc attaccaatc tccccacaca gaacaaactg gtaaaccagg atggacttat    65100
agcgtcaggt tggtcaggga gtaagataaa taatgattgg gcaatgcatg aagctcaggc    65160
tgtgttgatt ctgggatata ttgaagcata cagggcatcg aaaagcgatt tttatctaga    65220
tcgagccaaa gaagcttggg aagcctacaa tagtcatctt ctgggtgcat atgcagtaga    65280
aagtaaaatg caaagattgt cccactaccc tctatccaca gatggggttc catcacacgg    65340
tgggtttaaa gatgtggtgg tgtcttttac caatggtaga ggaaaaattc cagcaggatc    65400
tccaacatgg ggtgaatacc tggacaaggc attccaagcg tataacggtg gctaggaag    65460 aaacactgta gactctgatg tttacggcgg cacagatgct aacccaaatt ggacaacatc    65520
tggattaagt tggtgggttg agtggtatat agcatgggat ggtaaccgct attgggctaa    65580
cggtagcata gccgacagtg gtcatacgtc tgtagagttc ggcacaatcc aactgcagga    65640
taagggtgtt acaggcagcc acaaggtaac ctactgtgtg agattgccac aagagcaggg    65700
tggatcggtg atacctgctg atcccctgt aattgtaaac cctataaatg tggttgcaga    65760
caatcaagcc ccagagttgg acggggaaga atgtgtgt gacgcttgtt atcaactcta    65820
cactttgaca ggcgaggaaa agtattacac cgcgtttaaa cagtcttaca caagttgct    65880 taatttcagt gatataaatg cctacgacaa gttgtttaga aagaccacgt tgattaaggc    65940
accgttcaca gatggtactt gtctcgtcgc aggaacagtt cctgtcatga gcagggacag    66000
```

```
tgacgggtat atcaatttta gaatgaacgc acgtcagcct tgcgaaataa ttcaaaaagg   66060
gaccacatac aagataggca gagatgctga aattgttatg aatttcggag gagaaggggg   66120
tctgttccag ccacacttca ttcttaatga tggcaacaat aacaaaaaac agtataggat   66180
aggtgtccct tttggagggg cagaggtaac agagacagtt gccaaggtta ccgatttcgt   66240
agaggtggtt ggtaaagatg gtaacccgta tctcttacca aaagaggaaa acattgtcgt   66300
aagcggtggc gctagtgtta gtatgcagta tgataccgac atttataacc actccgacaa   66360
cttcacccgt tgcaacatag caagaggcaa ggtaactttc aattttggaa gagagatctc   66420
tttaaactca gtaacttatc gatcagatga tgagatggta agggtcaaat tcttgacaa   66480 agaccgttgg ttatggtatg ctgatctata tgccactaac ggacaatgga taacagaaac   66540
tcttacccta ggggatttta aactagaccc gacacaacct catcacacag aagatgagat   66600
taaacctttc tttgctaacc ctaaaggaat tacctctgta gatttcagcc tgagcgacag   66660
gcagataggc aatggcttgt tcgatctgta ttgcgtcaac acgctgccgc aattttatgt   66720
tgcagacaga gatgcttata tgatctggtt tagtgtatgg atggcaagca agacagaatc   66780
aacagccaag gtgggtgatt gctatgtcag aaactacaag caaggcgcat acagacacac   66840
tcctggtgtg ttccctgccg gaaaggtgat agataaggag aattatcttc tagaggaaag   66900
gccaaattgg ccctatcccg gcatgcaata tccggtagtc tactgtatgg gtgcggaaaa   66960
catagatcgt caaagattgg caaatacaat tggatttatg tacgactccc aagtttggta   67020
taataacaca tttagaacag aaggaccagt tgcatcccgc tatgtatggc agaggggtaa   67080 tgagggggttg actggttggt gggagatggt agataactct aaactccaat caagagcctt   67140
tgttgctgcg tgccgcacac tgtatgagct taagaaacat aaagaacctg ttgatgagag   67200
actgttcctg ttctgccaga aatgggcatg gttcctcaac agattccagt catctcattc   67260
cggaaatctc cctacagact ttaacacctc tggtggatat tcttatcaag acagaggga   67320 caggatgtgg gtggtaggtg aatggcttgc aggttgctgc tggctaggcc tttgcgggta   67380
ttcagaaaca ataccccaaa tagatattgt tgtagaagcc tgtgtgaagt tactgcaaaa   67440
gcaccacttc attaacgggg ataatgtttt aaacggctgc tgggcagttt ctgatccggt   67500
aggctatcac tctggcgaaa tccttcgcgg tctgggactt tatgctcaat accgtggatt   67560
gtacctttaa catagggggc tgtttgcccc ctttcaggag aaagaatggc tgatattaaa   67620
gttgtcagaa ttgaatctct tcctgccact accgcagtga cagaggatga ttacctggtt   67680
gttcaacaac cagacctgac ccgtcgtgta aaaattggcg atgttgtcca tatagatggg   67740
actgtttctc atgtaatctc ctttaaggaa ggtggtaagt taaacggccc aatggatttt   67800
gcctacttcg aagaggaaga cctctacctg cgttggaaag gcgaatttcc gcacactgtt   67860
cctgcactgt cttcaccgta cgccgatggt gggattactg atgctgcatg gatggtatat   67920
acagacccgt ccttaagaga ggagctggag tctaccattg gcgcatctat gatcatgaca   67980
gccgaagggc agtctgtcca ggatgtaatg gatgttacgg ttcagacagc caacgatgct   68040
aaagcacttg cacagcgggt agattttggt acagtgcata ctgtaggcga tgtcattcac   68100
cttgtcaact tgttggtcc tgcagttatt gaagagggaa gaaccactaa ctacccttct   68160
gaagcagctg gtgaaaaatt tctgaacggt gtggtatctc gtcgtgatac tacaactgtt   68220
gatggtattt tccgtggcgc tacctcagga gccatgtata ccattgcagt aaccaacggt   68280
gtagcaacaa caaaaagaat agcacttcgt gatgaattta acgcctggaa ggcaaacaac   68340
ccaacaagaa cagttatccg tgctggagat gatttaaaca cggcagggta cttgcagctc   68400
```

```
gatgcagcag gccgttgggg tatgtggaac cagcaaacag cttcgtggca acctcttgct    68460
atagagcaag gtggtacagg agccagagat gccgctggga tccgtatcaa tatcggtgct    68520
ttctataagc aacgtgtagc cattgaggca aatttcaata tcaataactt gactggtaat    68580
caggacggca tatactatca gccgatgact gctaatgcaa ctgaggcaaa tggttatcct    68640
gcaggttctg gtgctggtca cttgattgtt tggcagaaca atgctaacgg tggtacaggt    68700
tgtcgtcagg aatactatcc attctctaac gtggatgttt ggtatttgag aacctatcag    68760
gccaacacaa accagtggac tgcatggcag ccgatggtca gacctcggaa tgatgacacc    68820
ttcagatctc atatcggcct tggtaaaaac aactcccctg ctttcgggca cctttactta    68880
gctcaatact caggagatgt taaaaatgct tcaggtattc tccatggaga taaatatgac    68940
gctgatggtg ttcttgagca tggttatagg atctactccg aggtaagaaa cgacaataag    69000
acttggttaa cagtccacct gcacaaaggc gcaaaggat ctgaaactca tcggtattta    69060
ggattccgtg aagatggtgt attagattgt cctaagtaca tgcaggtcgg ggatctcact    69120
ggtcagctga caaactgggg acttggggaa tggattcgta gttcaggggc agaaagaggg    69180 ttctgggggtt ccaagaaagc cgctaagatg gtcgtctggg atggcggtat ggatgaatcc    69240
ggtaatggta ctctggaatg gggtgtttat aacaaccgga aggccaagtg ggaacccttta    69300 cctcaggcag cgggtggtac tggggctaca actttagcag atgctcagaa cctgtttaaa    69360
gttcctgtag ccgcaggagt aaaagatttc ttaacactgc caagaactgc agggatggaa    69420
gatgggaaat actacccgggt catcgttagg acagatccgg attatgctcc taccacagga    69480
acagatatta ctatagtcac caaatctgca actggaaatg cccctatgaa ctgtgctacc    69540
ttacagtgtc actacagaac tggtggctgg acggacaggg gtgattcttt ccaaggtgtt    69600
attaatttct accaaaacga gaaagcaatt cttgggtgca tagctccaac cagaagaaag    69660
caggagtatg ttgcattcta tgttgaggcg cgagctttcc ctgtcagtgt ctacgcaagc    69720
agaaacgttc ttgaagtatt taccagagaa aatgactggc aggtaggaaa tgtcactaac    69780
aaccaagatg gtgtcaagtt ttgcgctcct cttgcgtcag ataatttaag tcttgcaatt    69840
aaaggtgatg atgtaacaaa caccagacct cttgctgagt tcaagggcac atcggggttc    69900
tatacaggtg ggggcacagg ctggcattat gtagggactc ccgatagaat ggttctgatg    69960
agtaagacag aaatgccacc tgtagagatg tggtataatg gtcttaacta catttgccca    70020
ggtagccaaa caactcgaaa agcactgttc tctaatgcag ggttccaggc tgcgtcggaa    70080
ggaacagagg atctgatcaa caacaccttc acctctaaat gtggtaatgg tgcaaggctg    70140
caaggccagg cagagttcag atctactccg gaagctggtc aagttatcgt tcgcgatgtt    70200
gtaggtacag ctcataagtt ctacaatttc aacaaagacg gcacattttt ccctcctgga    70260
ggctatgttt gccagacagg tgctgactgg aacaatcagt ttggtaatac aaaccccctcc    70320 aagataatgg ctggcaatgt caacgggccg gaaggttcga tggttgttgg tggactgtct    70380
gtggcgtttt ctggaaacta tgctttccaa atggctggtc gccttgatcg attatacact    70440
aggtctatcg agggcggcaa ccataggggcg tggaacaaag tcatacaaca cagaggccaa    70500
ggtctgggga cagacgatct taatagatat gatggtactc gtgacggtat ctatcatcag    70560
ggtgcaaatt ctgacgcact cacatcccgt cattatcctg ctccgtacgc tggtacgctg    70620
attgttcatc agaatactgc taaccagttg acagggtgtg tgcaggagta taaacctat    70680 tttggtgaca gatatactcg tgctggcaac acgaatggtg aagattttgt ttgggaagag    70740
```

```
tggagacacg atgctggtaa gggcatccag ttaagaccta attacacttt cggtgagacc    70800
agtaatcaac tggaaattca tgttggtgct aatggtcttc cctccaacgc agatggctta    70860
cccaagaatg atgctgtact ccattattgg ggtaacggca gcacagggga tcgtccaaac    70920
gtgttagagt ttaaggttcg tgacgagtct caagcaaatt gggtatggca ttgcggtacc    70980
ttgccagata cctcaagata tctttctgta acggtgctg tgaattgcac atctgtcaat     71040
cagagttctg acagagacct gaaagataac atatctgtta ttcctgatgc gttagaagct    71100
atccggaaga tgaagggtta tacttacact cttaaagaga acggtatgcc ttatgcaggc    71160
gttatagcac aagaagtgct tgaagcgctg ccggaagcag ttagttcttt cgtgcaaaga    71220
aaggaaatcc caaaccctga tcaggatgga actcctctaa taacagagga aagattctac    71280
agcgtggatt acgcagctgt aacaggcttg cttgtccagg tttgcaggga acaggacgat    71340
aaaataaccg cccttgagga gcaggttaaa aaactaacag aggttgttac cgagttacaa    71400
ggaagattga agtaactgtt ttgccctcgc ttcggcgggg gctttttgtt tgtattgcgt    71460
attaacttaa aatctggtaa aataactatc atatttgttt aacctggagg cacaatgttt    71520
ttatgggaaa ggcctagata cctcccagat attagattgg agttactggc agacatcgtt    71580
acatttaaaa gcccgtttac aggtaagacg caaaaagtaa cctatgccac acctaactgg    71640
aaaggtactt tgacggtttc caatatcagt gaatctcagt tgttggagct tagaagtttt    71700
gttgatcagg tttacaaaga tggaaacatt tttcttatca aggcttatgg gcattcagtt    71760
acctccaacg agccaatcgc tctcggaccg actggtaacg acgattttt gaagacggtt      71820 ggttgggagc ctaacaggga tatagccaga gctggggata aatatctgt caatgatgag      71880 ttgaaagtgg tgacagcctc agtacgaagc gatggtgttg gggctgctgt tataaacata    71940
tctccaagac ttaggaaacc tattgccgca ggggatacca tgaagataat aactcaatct    72000
ccgaagggta gatttcatat cagagatctt tataaaatta gcaaaaggt tgatgctatg      72060 cagaaaggtg acaatatagt tatcaacttc tttgaggatt tctaagatga taagagcgcc    72120
attagataat ttatttcttg aaaagctaga gcttaatggt gttgagatct taattgctgc    72180
aaagctagag ctgccaacag ggactgtcag ggtgtgctca ggcactggtg ttgtagtgat    72240
tgagggtcaa cattttatag ggataggtgg atcagcaaca ttgactgctg tatctgagaa    72300
agatgccacc aactttggat ctgtggtagc aacattgaac gggtttgatc ccaagtatgt    72360
aggtgatctg ctgaagacgg agtattctgg ttgccgtgcc acgttatata tcaccgctat    72420
ggagaatggt ttacctgtca caactaatgg cttgtttgac ggtcttataa cagacatggc    72480
tattcagaca ggggagaata gtgctttgtc catatccatc tcttccatct tcaacagctg    72540
gttaagaggt tttccttacc gatacacaga ggaaagccat agctcaagaa acgataatga    72600
cagatttttt aaatatgtgg atcaggtggc gagccgcccg atcatttggg aggtttaatg    72660
agcacacatc ctcgtttagt agactggcaa gaaagattgt ggaaagtatt tgacgaagaa    72720
gccaccgtcc cgtttgaatg gggattccac gattgttgca cttttgcggc taaatgtgtt    72780
gatgcccaat acggaacaga ttttctttct aactttgaag gaacgtataa acagagttg     72840 gaaagcaaga gatggtgcat gctccgtttc aaaaccacac acctgcctac tattttgat     72900 ctcttttga ctcgactaga tactcctaaa caggttcagc gtggtgatat tgttatttc       72960 gaaggtctga acggcctcac cgctggtgtg ttctggaaca accagatttg gcgaaaggt     73020 gataaaggga ttttacgtt cgatatgaaa gattctatcg ttgttgatgt ctggaggtat    73080
taatgccaat tgcaatgatt gataacatcg ttgcttctgc aagatcttca agttatgact    73140
```

```
ggaacgcatc caaggcagct ctggctgaca gcctgaacac tgttaccacc agaactctgg   73200
ataagatttt tgagggcaac aaatcttaca gaagtcagca agatagacaa aagcttctca   73260
gatcttctgc tgcaccttgc tctgtagtgt atggaaagac acgcacatcg ggattgcttg   73320
cgtttttgga gcaggataga gacaaaaccc tccattgtgc tattgttctt gccaatcacc   73380
ctctggaagg tatagaagat atacttatcg atggtaatcc tatttcctcg tatggagatt   73440
tggtatcgtg ggagttacat aacgacagaa aaacctctga tcctttcatg ggtacacact   73500
gcccatcgtg gtcaccggac atgataggta gagggatcag ttggctacgg gtcagcttca   73560
ggtttgaccc taacaagttt cctttt gggt tgccaaacgt cacactcgtc aaggttggta   73620
aaaaatgcta tgatcctcgc accagtaaag aggtgtatac caataacgct gccttggtga   73680
ttctggacta tttaagaacg taccttaaat gtcctgacga aaccatcaac tgggagtcct   73740
tcaaggaggc tgccaacata tgcgacgaag ctgtaagaaa cgcagacgga accagtgagc   73800
gtcgttacac cattaatggt gagtttgaca tggatgaagc accagcaagt attatggcag   73860
aaatgctgaa agcttgtggt gcagatctta gctatgtagc tggtaagcat ggtctgctgg   73920
taggtgcata ctatggccct gcaacaatga cactgagtga ggactgtgtt tgcggtgagg   73980
ttaagatcta tccggaagcc tctttcgata aagatcgaa cacaataact ggcagattca   74040
ccagtccaac caaaggatat tctgaaacag acttcccatc ggtgttcgta cctgagtggg   74100
tagagaagga tggagaaaga aagataattg atatagatta tcgttttgtt accagtcctt   74160
atcaagctca gcgtgtttcc gcaatattct taagacgtgc cagagctggc aggattattg   74220
aagtaacctg caatatgcgg ggttttaaat ttaagcctgg gcgttacgtt acgatggacc   74280
ttccaagtat tggtatagtg ggccaagaaa tgagggttct tgaatgggag ttcaccaaaa   74340
agggcggtgt caaggtaaaa ctccgtcaag atgctaaaga gtggaatgat gccacagggc   74400
aacttccgga ttctggagat gtggatattc cgatatcccc gtccggtgta gctcaaccgc   74460
aaaacttcag atactctgtt cttcaagctg gggaagtaac tcatggtgtt ttggcttggg   74520
acaacgttgg aacttatgct caaaatattg tgcaggtaag aaagaacgga gagattattt   74580
ggacagcgca aacagtcgag cagtttgtcc gcgtagaagg attgaccaaa gggtcatata   74640
cagcaaccgt ggttgcaaca tcttataagg gtggtgtatc tccagaagcc tactgcgagt   74700
tcaacattca agcacctgaa gctcctgttt ctgtagaagt taagcaggga tactttgcta   74760
tcaccttgat tccgcacagc agggacttag caagtgtaag cacccagtat gattttgga   74820
catctggtat gacaaggttg cctgacacaa gtgatgcaac cgttacttca aaagccaccc   74880
gtatgggtgt tggttcaact tggacatctg aaggtctgca gaacgataag atttattatt   74940
ggtatattcg aaccacaaac gcttttggta gttctcagtt tgtagaatgc gctgcacgct   75000
gctacacctc tattgaagat ttgatgcctc agatagatgc tgaatttaaa aagacagaaa   75060
cttataaaga gttgatgagc actttagatt cctctatcga ggaggttgaa aatcgtgtca   75120
cagagcttaa caagtacatg gacggaaggg tagatgaggc attccaacaa cttggagata   75180
ggataggtgc ggtagttaca gagacaactc agaagtttga ggatgtcaat ggaaatatca   75240
cagctctgga taggaaactt gttgctgcac agaacaagtt caccaacgat ctgaacactg   75300
aaagtggaag actggcatcc ctgatcgaga caaccaataa agcaaccact gatcttctga   75360
acaaaaagac agaggcttta gacgagaaat tggttgcagc caaaggggag ttggtagaac   75420
aaataagtgg tgtggagagc ggataccttg ccggagataa aactctagat ggcaagatca   75480
```

```
atacccagag aacggaactt gatgcaagca tcttaagcac caaccaggcg acagtggatc   75540
ttctcaacag gacatctgaa actctggatc aaaagatcag tcagacaaac gcgacggtat   75600
ctaagaacta taccacccct tgatggtaaga taactaccgc aaaaactgat ctcaatacct   75660
tgattgccaa taccaacaag gccaccacag atttgttgaa tcagaaaacc tctgcactgt   75720
cagagcagat aacttctgca cgtggggaga tttctaccaa caaacaggcg attaaggatt   75780
tggatgggaa gctgacctcc acaaaaacag cgctggacgc tacaatctcc gataccaaca   75840
aagcaaccgt ggatcttatt aacggcacag cgtcagctat tcgtcaagaa cttgctgttg   75900
ctaagcagga gatcattgat gatgtcggtg atgtgtcaga gctcagagct gcagtggcta   75960
caacatctaa agctgtgacc gacttagagg gcaaagtaaa tgctcaatgg ggcacaaaaa   76020
tacaggtaga ctccgcaggg aataagtatg tggcaggtat ccaattaggc atggaaggct   76080
ctggaggcca agttcaatca tacttcatgg ttagtgcaaa caactttgcg gtatacaacc   76140
ctggaaatgg aacagcaacc cttgctttcg caattaagaa caaccaagcg ttcttgaaag   76200
atgcttttat agagaacggg acgatctctt ctgccaagat tgcacaagaa atttcgtcta   76260
acaactacga tggcaacggg tatcataact acggttggta tattaacaag aacgggcacg   76320
cccagtttat ggatgtgtgg gtgaaaggta acatcaacgc cagttctggt aacttcacag   76380
gggcagttaa cgccactagt ggtaccttcc gtggggatgt ttatgccaat aatggtagct   76440
ttagaggcac catagatgca accggaggta ccttccgtgg gcgtgtagaa gcttctgtta   76500
tccgtgctaa ccagttcgaa ggtgcaatag ttgcacacag aacctacggt gactgttctc   76560
cagtatataa ctcgcagcag agggtttgcc gttggagatg gagatatgtg gacaacgtac   76620
aaggccaagg taagaacgta acattcttct ttaaaactgaa cggtacgcgt gccaactctc   76680
aactgaatgc gtggatagct ggtcatcagc tccttgctgg caagaagtac ggaaacgaca   76740
atgacggtat gtgcgctatc gggataacag gccttggaga acaaaccata gacattatcg   76800
ttgaaattta cacgccgtgg tcaacagggg gcgtgacagg catcacaata tcctgtccta   76860
ccgttgtagt aagtcgttca aactctagct tccagggacc ttggaacgag tctcacgact   76920
aacctttaaa gccccgcttc ggcggggttt atttttatgc tcagattgac tattgttaca   76980
aaatttggta aaataccttg tagagatttt cataccggag gagtgacgtg gctaagtatg   77040
gattgacaga ggctggtttc gttataccaa ccctaaatga cctaatcgtt gaaactaagc   77100
aaagcctgat ccgtgctttt ggcgaaaact tcaacgtaca aagtaactca gttgcagata   77160
agctgaccac tatcttcaac gagcgagaat atcaacttat tcttatgca gcatctgtat   77220 acgcatcgca gacgctgtac ggggcagaag gtatttacct tgatgaactt cttgggagac   77280
agggtattta ccgaagaggc cgttctaaat catcaggtac ttgccagttg acaatcaaca   77340
caactgtgcc gtacaatatg atttatgatt ccaaaaccta cacgctggat agtggcaact   77400
ttgttcttag cagtgacgtg caggtggcgg ggaatcttat tgctcacagg ataaacgctc   77460
cagatctaag aattggtaaa tacaactttc aaattaccaa ccaggcagac ggaagtatca   77520
aaacaaaaag tctggtttta accgataagt ctctggactc ttctgatttg ccaagctttt   77580
acggcgagat taagcaattc attgtcgata atacaaccct gttgaacgac gatttaattc   77640
agatagatat gttgacagga acgttgtgga taggatacaa ttcgaatctt gatcaagttg   77700
ggcttaatag cagagtagat ttcagagtat ccccgattgt aggtgaaaga actatcaccc   77760
tggatgttat cgctaacgag gcaggtgagc tgtcaagaga ggcagaaact gtaacaacaa   77820
tgtcgcctac tccaagcgga tttatcaaac ttaccaaccg agaaagattc aatgatggca   77880
```

```
gggatgttga gaaggactca gagtatcgct taagagcttc cagcactaag cagttgacat    77940
ctaaagctac tcgccccgca atccttagcg ctgtgagcga agtgaaaggt gttgagaaag    78000
taagagtgtt ctctaacaac accgataaaa cagatgcgaa aggtatacca ccttacaagt    78060
ttcaagtggt agtgttcggt ggtgcaacag aggatatttg tcaagcgctg tatcaaacca    78120
tagcttgcac aaacagaact tatgggagta tcttctacga tattaccaca tcagacggtc    78180
agactgaaag gatttattat tctaaggcaa acacttaccg cctggatatg agaattactt    78240
actcgggtgc tgcactttcc actaccgaaa aagatgccat tacagaggct cttttgcagg    78300
ttgttaacgg cttggatgtt gccgacacgt tgtataatat ccaattagtt ggcgctgcat    78360
cggctgctgt gtcaataggc agatttaaca gacttgtaat tcaagttaaa cctgtgggag    78420
cctctgacga agcttacact acaaacgata ttgttgcaaa catgaccgag gtgtttgacc    78480
tcgacgaaag taatataact ttccaacaaa ctatttaagg cggcgagata tggcagagat    78540
taagtcggat gtcaaccaca tccacactct gccagattt gttcagggag gtcttgacta    78600
cctgcctgga gattttctgg ctgagaaggt taatttagtc acattcttaa ccgtgtacct    78660
taaaaggttg gagaatgttg ataagatgct ggtaggtttg gctgaaggaa gactgcttaa    78720
caatgccagc ggaagatacc ttgacgaagt tggtaatcaa ctcggtattc ttaggaatgg    78780
gctttcagat gcagttttc gtgctaccct ggttattcag caagcagcag catcaagggg    78840
cgggactcgc gaagatgtca tctccacatt gcgacaattg ttcggaagag ataatttcga    78900
tacgtggaaa ggtgacaact tcagatttga cataaatatt agaaaaactt gctttgacat    78960
attacagtcc atagatcaga tcttagatat gctgccattg ccttgtcatt tgcgtcttac    79020
agaatcgcaa gggcaagctt ttggttttga aggggactcc acagctcttg gcttcggatc    79080
agtatgggaa gaaaaccagt tcggagttgg tgggctggct actttgctgt atgttcctga    79140
cgtaagacct gattgggaca ccacaactat ttattgtgaa agtattacag taaacgcaac    79200
tagacaggag ggttaatggc aatagctgtt tttaaacctt accgtgatta ctctacaatg    79260
gctgcacggt ttcattatcg cacagttcaa gatactgccg ttccaggtag ggattatgat    79320
catgttgagg gcgatgtaac tatcccggtc ggggcaacca gtattgagat tcctgtagaa    79380
attgttgaca aattgccaaa caggttgcca agaagcttct ttatggagtt ttcatcaaac    79440
tcccaagggg ttatgattgg aacacaaaga gcaaatgta caatagtttc agatgagaat    79500
cttgacagaa tatcttggga taccgttgag gagaggatgt ttcacccaag atattgggtt    79560 acaaacacgag agcagactga aagcacctgt attgttgcgg ataataactg ctgtattaac    79620
cgtttagtgt caagaacata tggaggcatg gctggtgca tttgggaaac agttgacaag    79680
tatgaccatt tcggcattgg atttgatgat cactatgaga tgagaaacac caagctttgg    79740
ttcagaatgt caataactaa tgccagcaac ttctccaccc ctgaaaagat gattatgact    79800
gtagaccttg ttgatggcac aatcatctat gttcctttag ctcaatatgc tgtcagcatc    79860
tcagaggata agaatgttgc agaaattcat attgatttcg aggactgcgt cgggatggac    79920
cagaacaaca acatgatggg tgttgatcct cgacaggtga aaggattct aataccactt    79980 atgcctaaag attgggtaag taatagcaca gacccaagaa cggaaaatgt agagtgtgag    80040
ttgcgcctag atttgcttca gccagacaca ggctggaaaa tgatgcaact taacaatatt    80100
caggtgagag agcacgacgt tgggatctgc accgcatatg acgatatgtg gaacgtatct    80160
cctttaaggg tgttgaacaa tatcaagcgt ctgggctata ccggaaccat aaaccattat    80220
```

```
gttggtatga gtcattatta tgactacaca tggtcaggaa cccaatggtc tataaacaga    80280
acaggagcgc taaacgctgc agcttataaa tggcatgatg attttatgta caatgccaaa    80340
cgacataact tcgacgttat gcaatctgta agttttgagc ttttcagcga tgcctgcccg    80400
ttggaatgga cccaaagaga ctggaacgat aactacgcta aaacaggata tacaccttgt    80460
agctacctcc tgtctccaac cattgaagag ggtatgaatt tccttactgc agtatttaag    80520
aattttgcat cagccgctat gagaaacaac ctgccagtga ttatgcagat tggtgaaccg    80580
tggtggtggt tcaataccga tactcgtaag ccttgtattt atgactaccc tacaaaacag    80640
gcgttttatg atgagactgg tgaatatgca ctagacattg gactattga cgatcctaaa    80700 actggcggtg tttatgacaa gtatgtagca ttttgtcgtg gtaagcttgg agctcgtatt    80760
gcagctattt caaaggcaat aaaagcacac gctgcatcgg ctcagatgac agctttgctg    80820
tttttcccga ccattatgga aaccgagctt acgcaaaagc tgaaccttgc tgaccaatat    80880
aaaaaggaag caggtgctct tgatttcttc tgcactgagt gctacgattg ggtgatgcag    80940
ggtggcattg aaaaggcaaa agaatctgta acataccta tcgttaagtt aggttggcaa    81000
ccgtctgaaa tacaataccct tgcagggttc gttcctagca aagagcttgc tccggtatat    81060
ggctacgacc caaccaggaa ttaccaagaa tttttatgga gatgtatctg cgggaacatg    81120
gcaaccatag agtatagata ccctgaggta aaacagtatg tgtgggcata cccgcaagta    81180
atgtctgaca gcatcactgt taccgccaga gattctaccg tgcttcatat ggggcaggtt    81240
gctctgaaag ggtatgtaga agatgttgtc ccgccagact tctcataatc aggagataaa    81300
atgtcaaaac ctagttttcc attagagatt tgggcagagg aggatcaggt tctgcctaac    81360
acccacagac agaacaggct acgcccgatt gatgatttgt ggagaaaagg ttgggatctt    81420
ggtcaaaagc catcctgtga agaacttaac tatattttca atatgctcgg gacttgggca    81480
aaatacattg ctgacgagca gatccccgct caagaaggcc gttatctggt acgtgataat    81540
aacttgagtg atcttttgaa catccctgtt gcccgtagaa accttgggat tattactaag    81600
gaagaggcag acgccaggta tgtaaaagtt acaggcgata caatgacagg cccattgggt    81660
ttgcaacgta tcaactttaa agctgccgag acagataagg cttggataga cacaactatc    81720
ggcccagata agacaaccct tgactttggg ttaagtgata atattggggc gttcgatgat    81780
ggtggcacat ctacagtaga tgcgttccgt tggagatttc agccaactcg gccgacatt    81840 aacccagagt tcactttgat gtatttgaac gcaatcacgg ctaatcgtgc gttgttgaaa    81900
gtggtgggta atgttgaagt tgtcgataac atgcggtgta ataacctcac cattagcagc    81960
acagcaacat ttaccaactg caatgtagtt agtcagttga cagctgggtc ggtatatgtc    82020
aatggcggtg caagttgtga cagtatggtt gtaagaagcc agcattgtgt tgtcggtaac    82080
agaaatgtgg tgcgctctgt gaatggagtg acggctaacg gcaacggaga tgtaacgatc    82140
accatcccgc agacaggtgt acaggatatc agaatcggtg caagacttgt cgatggtgtt    82200
tctgaatctc cagttcgcaa tggctacgtt gtcacaggtt ggcattttgg tgataaaaaa    82260
gagatgcgtg gttcaaccta ctgggcaggg cctttacaga aacttgtaaa tggtcaatgg    82320
atcactgtta attatgcgta gatcggagga ctagcatgaa aatacttcaa gagtttaagc    82380
tttaccagcc gggatctggc gaataccaca ccaacaaagg caccaaggag ttgactcctc    82440
aggaggttga ggattacacg acatacactg gatattttt acgtaatgat gatggcgatt    82500
ggtatgtgca atcacgaaca ctcgacaag aaaatccagg ctgtatcttc ctacttgttg    82560
acgagaaggg tattcttaag acatctacag aagaacctga tgccttgtgg cctgctccag    82620
```

```
gtcttcgtgt ggttatcgcc aaaaaagaag aggtaccaga aaacattatg ctccaccacg   82680
acgctttgcg tttagttggt gacgaatttg tcacagacaa tgaattttt gttcaacagg    82740 cagagggtgt catagagaca gaacttgctt gggctactgc tagaattggt gcctatcaag   82800
acatgattga ccttgaatac gatcttactg atgaccaaaa acgcaacatc agagatttga   82860
aaatgtacag ggtaaaactt cttgaaatag atacatctaa agcccctgac attttcttcc   82920
cggaacgacc taccctctaa gaggaggtgt tgtggagttg gatttggcgg cattatacgg   82980
tatctgcatg ggtaccgttg tcccgatctg tgtatgggct ttcaaccagt ggcacaccaa   83040
atggaaaggc atttccaaga ggctggatga gctggagaaa gacctcattt tagtgaaaaa   83100
tagcatggtt acaaaagata gacttgattc cattatcgag acccggttaa gtaagctaga   83160
ggccgatatt aacgacctta agcaagatgt caggacagat gtctccggta tcagagccga   83220
tgtgcaaaag attttacaca tgcttgtaga gcatagtaaa aggtaaacaa aggtcagaac   83280
ggcaaggatg ccgttcttgc attttgttct ctaaaatgtt aaaatagtcc ttaagaaatt   83340
ttctcaggag aacgtgatga ctaaaccagt tatccctctt gatatttggg ccaatcagga   83400
tgttgtgctt gaaatacag gagagttgaa caaatctcaa ccgagcaaag aagagagatt    83460
gaaaggttgg gatatgacac aaaggatagc atgtgaagtt gttaactttg aactccacat   83520
gctctctgcg tggctaaagc atttaacaga agatgttgtc ccaggatggg ataacagatt   83580
cttaagggtc actaataatc tggcagacgt tccagacaaa gctgctgcac gtcaagttct   83640
caatgtatac tcacctgaag aaatggatga cctttatgtt gacaaggctg gagataaaat   83700
gatccagact caaactttag gtcttcaaag gatcgagttt gcatctgcgt caacagataa   83760
tgcggcgata tataccacca taactccaga caagacgatg atggatttct ggattatgga   83820
caacatcggt ggtgctgacg gcacagatct tgatgatcct tctcaccaaa tagacggttt   83880
ccgctggaga tttcaaccgt ctggtgggca gcctgtgttt tcggctatga agctaaatgc   83940
tataactgcc aaccgtgcaa gactggctat ccaaggaaat cttgaatgca atgatgcaaa   84000
aagctcctct gcaaatgcta atgcggtaac aataccgaga gccactgtta atggacaaca   84060
atcctgcggc agcgctcaaa taggtggaag agtagattgt aacgataaaa ccgccagggg   84120
tcaatatgca acagttggtg gaagaaacgt ggtccgcagg gtaaatggca gtagcgcaga   84180
cagtagtggt aaccttacta ttcctatgcc tagtaggggt gttgaggatg taaggatagc   84240
aaaccgtttc agaaccacct acagagaatc aagagtatat cctgggcatg taatgtgctc   84300
cggcaattac gcctataaac acccgtatca gggcgactat tggactggag ctattcaaaa   84360
atttgtaaac ggtcaatgga tcacgatatc ttatgcttga agagggtaaa tgaaattaac   84420
tcagttttta tggggactgg ttgcagcatc tgatgaccct acaaaagtgt cccaatctaa   84480
gctatggtca acataggca tggcagtgat gactggggtg tttattcata tggggtacaa    84540
tgatacgctt cctgaatggt atgcgtggat atacgcacct tcagtagcct gcccccagct   84600
tattagcaaa ttcatctcgc tccggtgggg ttgccagcac cctgaccacg ttaaaaacga   84660
agagcaaaaa gcttaaggag aaatcatggc gcaagacatg acaagctttg agcaggcggt   84720
agatcaagta attgttgatt ctgaacgttt gcacttggtt gtcaacggta acgctgtgga   84780
tgaagttgtc gtagaggatg ggaccactat ccctacggta cgaaaagcca tgcttgacaa   84840
cctttatttt aaaacgccac cgatcccttg ggcgtatggt gcatccacaa cagttttaa    84900 ccagctgtat gagtttaaag gagatacagg ccctcaatgg tggtacgctc ctgcagcatc   84960
```

```
aaaatctaac ccagttagga tgccagcaga tccttcacaa tctccgaact ggagattata   85020
taccgattct gcagtaatgg caaaatacta cgcaaaactt aacagcccaa ggttcgaagg   85080
tgacccgcga gtacctacac ctccaatgga cgataagtcc gagtctatag caaacacaga   85140
gtttgttgtt gactatgtgg acagcatatt taaagccatg gaggggatga aagttactgt   85200
agggtctttg gtggtaaaag gtcttacaga acttgctaac accatagttg ggggcacact   85260
caccttacat gggcctgtta atggagcaga ttctactgca cgctttagga atctaatcct   85320
cacggcaaat acttctacac ttacttttgc gtggagcgat cctaagcatg cagactggag   85380
aagtacagag ctgcaacccc atgaagtgtc cacccacagg gttatagctg atactataac   85440
ttctgggaaa ccagtggcta ataataacga tgtacatttt gatggtctgg gtaataactt   85500
ttttgactac gtgtacattc gtggtaatgc catgaaggca gcaaccgaac caacattaca   85560
ggttgctggg accaccaggg ttaagaacct tgaggtgaca ggtaccgtta cagggataac   85620
ctactctgta gatggcacca tgatctaccc tagctatatt gaaagcacgg gggatgcact   85680
gatcaatggc gatttagagg ttggcggatc tgtagttatt cgaggtacag catctatcca   85740
aaacatatct ctgaataccc taagagtcaa tgagcgtgca acttttgaag gagagggact   85800
tacagccaac aaaggtgtaa ttaccgagct gacaaccact actttaactg caacgactgc   85860
aaactctgaa aactgcaacg ttaccaggaa cttgcaggta atggcgatg ttagcttaaa    85920 tgacaacggc acaggaacaa cacgccttca taaccttgaa atatccggca cagtgactgg   85980
gtggctacca gacttctcta atgtcaactt tgtttgtaat ggtattaact ccagcggtaa   86040
gataaccacc tctcaaggaa ttgaggctgg taaaaccatc actgcccccta ctttccacgc   86100 aggaaaagta gactttgact tagaggaggt tgacgcgtcc agcgggacat ggacacctaa   86160
cgggcaggcc agtatgtatg ttgtccacgc gaaaggggga tttacaatag acagtggcc    86220 tgggacatca gcggaagata aaccttatcc attcactgca gttatctatg tcattcaaga   86280
tgctgtaggt cacaacgtga ctttgcacga taagtatgct atcctgtcgg caacacctgt   86340
tattaacaac aaggctaaca gtgttacctt gctgcaatta acgtattgtg gtgttggtga   86400
tatcgtagac gtagtaattg cacaacgtta atatatctaa ccgctcctga cggggcggtt   86460
ttcttatctg gagaacacaa tgcttccaat ccctttgcta aaacttggtc gtcatttcct   86520
cgataagagg ggtggaatta aggaacttgc tgttctgtca tacccaatag acaacagtga   86580
tggcacaagc actacagtac cctatgtaaa tagcttagct atacttttg atgatggtca    86640 acttaatatc acgggctata acaggttcgg agagtccgt actggggatc ttgacacgat    86700
aaactatccc aacgaggctg cctggaacgt tgatcatgtg tggagagcag accgtgcgtt   86760
tgtaatccga acttttgata atcagttttt ctacatcggc tgcactgcag gcttattgg    86820 gtctgatgcc gcaggcggta atgatgtttg tgtaagagag tggacacctc ttcctgaaca   86880
gatcgttaaa gggttgcacc ttgacaccca cccagagcgc cttattgagg tgatgggtgg   86940
tattaacaac actgtctggg ttattgcaga ggcagaaggc actggtatac tgaacctgta   87000
cgggtctggt aacaacacct acggatcttt gcatgtagat aaaaatcagc atgcaacccc   87060
tgtaaagatc ggtgagacat cggaaaatcc tgaaacaggc ccttggaaaa acccaagcat   87120
taactgcgag gtgcatgaca actctgttat tttcggcggt cctagaggtt tctggattgc   87180
tggatacgat tttctgagaa acaacagtag aaacgacctt gtttggcctc ctgtgcagat   87240
tactcgtaac gatttgaggg gcattcctgc agatgaggag tggaaagggt ttatgtgcgg   87300
tcctaacggg gcaataattg ccacgcagag gatgcacaca cccaatgacc agcagcttgt   87360
```

```
taacgtattc tacgggcaaa acgtctgggg agatgacaca tggcgttcct taaatatcac   87420
ctacacccat gaggtgataa tggctcgtgg atacggcaca agtggcattt tcttcaataa   87480
tggcactaag cagtatcgtg gattctctcg caacttgtgt aatgatattg gcgcacaatc   87540
tgcaaacaat agccctaggg ccaattttat ccactatcaa gctcttgcca cagccaaata   87600
cgttgagcaa cgcctcccag ttagctggac agagagtgtt tatttccaag gcatccacag   87660
ggaaggtttc ttaggaacct ttactgttgt taatggtaaa ctttggtggt caggcatccc   87720
aaggggaaat tttgcaggat ctaataacct gtttggcggc agacttaata gccaagggtt   87780
cacagaggtc cccgagaatt ggtataaaaa tgtcccagta gacagttggg gtgttgagga   87840
tattttcgac gttaacggtg ttagcagcgt tagcaatatt tacattggtg atacggtcaa   87900
gatgaaattg aagcctcagc cagaaggggc cacgttcatt attgacaaga ttgaactggt   87960
aaatgctgca ggtacggttg ttacagatgc aaattaccaa ttctctacca actggaacca   88020
cggcggggcc aacgaagtta ttgttaccca gtataacagg aatgttaaca ggcgtggcct   88080
gtactctgta aaaataacct atcatgacaa acatggcaca ggaagaaccc acacaacaag   88140
gaatttgaac tggaacacta tcgtcccagc gtatccgtct gatggtaaat ggcatactgt   88200
aggtagaaac aaacagttcc atgttaacga cactgtatac tttggactaa atgcggccca   88260
gcctgcagta aagggggata catcgtatat ggtcagactc catagaatgg atgctggatc   88320
agtaacttat gatgttaccc aagagattta taatcagcga cgaaatacct atgataactt   88380
ggtgcagaca caggccctat gggagttcaa cccaaacgga aggggtggta aaatgttgca   88440
ggtcaacgaa caaaacggga catcgttgac tgttcacgaa cacccaaacc cttggcctga   88500
tcctgggaaa ccgaatccag gtgctcgtac actaaaaatt gtcagccatg acgtaggata   88560
tttcggaata cgttgggaag ccacagtaag atatgccgac gggacaacaa acaatattgg   88620 gattacccctt ggcggcacca gtgaggataa ctcactgaaa attgcctaca ctcctagagg   88680
tatttctatt gataatatgg atgttgttcg caatggttac ggcgatgtga atgtcaaagt   88740
tactcttggc gagcaccttg gtggggaaag gattatcatg tatgcttttg atcatgatcc   88800
gcgcaccaat ggaacttatg caaatcaggc atggagttac ctaataaatg cacctgagcc   88860
gaatactaaa gagttctact atggtatgaa gcgagatgtg tgcaagaaaa caggaacaca   88920
tgactggatt gctatctgcg ttaaagatga gcgcacagct tgggatgagc ctgttaacag   88980
atggttcata ggtattccta ccagaagtga taagtatgtc gcagagtata ttgtatgcat   89040
gggcggtacc aacctgaaca tgtgttggaa cgaagatgta aacaaatact ctacttatga   89100
ctatatgagg gattacgctt gtaatctgtg gtttagccaa actacaggtt accctccgcg   89160
tcaggcgaga gtaaatcctg caatcttcac agatacgcag gttttcttga caaaacaggc   89220
taacgaggtt cagaccttta agaacaaata cgaccctaac aagtggttct caactgttc   89280 cggagcaata ttctggggac ctgctgaact gcctgataca ggttcttgct tagggggctgc   89340 aacctatggc agtgactata ttatgggtca ggtcaagaag tacaagataa ttcctggacc   89400
tgcaattcta ggtaatgctg ttgacccgta cataaatttc gcagctatac atgctaatat   89460
ggatggaggg agatatccgt tgttgttcc gttaaactgg gggtacaaac gtgtcgtaat   89520
gattattaaa tgcgatctga tcgggaagca agttcttgca gaaaacggaa cctcaacaca   89580
tttattcgag actgctctgc actaccagtt tgcagactca ccatatgcag gggataaaag   89640
aatatccgac acagactcta agcgctgtaa gaaagtttta cttggagctg ggtggtggtg   89700
```

```
gtacgagttt gatttgacag ataagttcac agatgatacc aaaactctca caggtatccg   89760
tctggacctt ggtgagaaca tgcataaaag tgtttgtgat ggtacctacg gtgaccctac   89820
ggtatatcta agtatgtttt ctcttgagca tcgcgaagag gatgtttatg gtccaaaact   89880
gagattgttt ggctcatgga ttgctaaaga cagagtaggg atgggtaaga aggtgagagg   89940
cttcttgata gatgcaggga cagaagacat gctggttaat gcagtatggc ctgaattacc   90000
aggaactcag tgggacaact ctgccaaatc tataaactgg tacaacattc acagagccat   90060
gtggaccacc aactgctact tgtggagaga gcttaacgat caggctttcg gcttcagtaa   90120
cggtagaagg atggcaatca tctgctggac aacgctgcaa agatgttatg accatgacta   90180
cgagattggc ggtagggcat ggaaagatat tagggataga atcatataca attttgcaga   90240
tgataatggt ggcggggcgt ataacttcgg cacaagcagg ctcatccatt tgaacggatc   90300
cttggcctac aagaaagaag gctactctgg gtccatgatt gagtggggtc tggtgaaaga   90360
tgctcgcgta ttgatgggtc aacaacttgc tgctgcaata ggacctaacg cagtgcagtc   90420
tgtcaaacca gcgtggttcg atatcccaat atggtcacct ggaacaccgg gaactgcggc   90480
aatcaaccct accactgggg atctggaaat ctcttgggag gacttaaagc aggtcggtgg   90540
ctgggataag acaggctacc aggtgcaatg gtggagatct gacggatcgt tagcggctga   90600
tgagtttgtt aaggacaatt tctacaccat gtcctctgca aaagcacagc aattgtttgg   90660
tcaggccact ccgtcaacga tcaccatgtc catgtgctgt aaagacacca ggactggagc   90720
tctggggcca agggttgcta agtttttctc aggtattaaa tggaatctcc ctgttcaagg   90780
tgtttcatgg aagcaaatag gcgataacaa gctactggtt actcctgcct gccagttcga   90840
tgcaactctt gacgttgatc cagctgttgc agcaaactca gccagagctt ctgacttctc   90900
tgtgtctaac actgctatgg cagatgtgag aaagattgac acactgaatg ccagaattac   90960
ctgtaaaaac acttatggca cattccaaat catcaacaac ttcacagata ctgattctaa   91020
ggtggtgagc acagcaagcc agactatgca gttgggcact ctggcatact ctgccctgat   91080
cactgaacag tcctccactc tccagggtgg tggtgttggt aagttgatca caaccctgt   91140 gtggaagcca acgagtggg ttgtgtttga tttgactgtg gacttctcca gcgataataa   91200
ctggacatgg gtgaggaatt gcttgtcaca gctgatgggg ggcccaaact ccattagtga   91260
tagccatgac tctactgacc cgagtgtgtt ccaggttggt aaaactcacc cagagactgg   91320
ggcactgttg cctgacagga agtatgcttt ggtttgcatc tccaacggca aggcagatgt   91380
aaccttctca gggacacaca catataacgg cacttacaac ttctctaaaa agtacagcct   91440
caaggcaggt aacattgtag acgaggttgg tgcgttgtat aatccaggga acgggatagg   91500
gattgtgggt ggtaagctgc agatgcagga accttctatt accccttcca atgtgccagg   91560
aattaggaag acttgggaaa gtagtgatac caacattgca acagtggatg ctaccacagg   91620
gctggtaaca tttaaagcta ctgggaatgt tactataagg tttgtagtta cagatgatgc   91680
aggacgcaaa acgtcttcaa catcgtttac tgtcaaacag atggcaccac agtggagaat   91740
gtggataggt acagcaacaa acggggcata tcctaatccg gcagggactt ctggtatgaa   91800
gactttctct acaagcaagc cgatggagta cggcagcggc cctaaggtag ggcagatggt   91860
gtactttggt gcgtatattc ctgaaattat agggcttccg agaagtcagc ttcagttgct   91920
gtttggggct ggtgttgacg atcttgccac tttcgggtat agagacaaca tcgatgctgc   91980
aaggagttca ggatgggtag ggttcagaat ggagtctgga aaggaaggca ggattctagg   92040
gacagcctct ataggtgtta tgttccctgg tgaccagcag tatcgtctag aagcctacgc   92100
```

```
aaccttttct cgttaacaag aggggtaaat aaaaaaaagg ggggccaaac ggcccctttc    92160
tttttatagt tagtaatact cccaacatgc cccatcttca gacggcttga cgcgcttacc    92220
tttatggtca acataggtat agccacaacc ttcacaaata acaggtgctg catagccttc    92280
cttccactgg tcctcagtga tcagaccttc caaatctttg cagtcaaagc caaacaactc    92340
ttcagagcaa tctttacaaa aatcggccat ttctcagtcc tcgcatttaa caaattttc    92400 tacagatccg ccaagcacag cttgttgctt gatggcactt ccttcatcat agtggataga    92460
tttatgctcc gttccaccaa acttccctgt gtggaaggtg tgcacccaaa tctctttggg    92520
aagggattta ttctcttcct ccaccaactc ccacataccc cacaagtgat ctgtgatatc    92580
tctgatgaaa tatctttcgc cgaggtttgt ccacacacct gccccaactt taccatctat    92640
cccattgtat acatctgcct catactcttt tcctggtgta aagtgtacac ccatcctaag    92700
ggctgttatt ccgttaggat ttttaaatct agcaaatttt actttgctca tattacttaa    92760
tccttgcagt tacagtagcg ttataccccca tgtagttatg agacataaag aatgtaagcc    92820
ctttaagttt aggattcttt ctaagaaatc gtttcaattt tcgaatgcaa ttaacaccat    92880
gatcatagtt tgagtaatta aatttaatac cctgctccat catagtgatt acttcttcat    92940
gggtatgcca ctgttgatcg tggtcacaaa accaataacc aataccttct ttttcttgga    93000
tatgcaaccc ccaaaatact ttatgcattg gatattttgg ttttctacca tgataatgta    93060
gtgattgtca ttaccaaaca cggcgcgata agctttagca gcaccatggt ataacttcca    93120
catcaagtaa tggtatcttc gtttcatggc tctttctccg gttcagggtc tgggtaatct    93180
tcaataataa agggccatcc attacgctta gcgtcagact tatactcaat ttccttcatt    93240
gcaaattcta gctgattctt agctggaatg caagctggag aatcatcaac ccagatgtcc    93300
gggtagatat caaactgcgc cagataagcg gccttttgaa cacctccagt ataaaacact    93360
ccaacatcaa gttccttgcg ccagtattca atgtccacat tatcttgagt gatgaatcga    93420
aaagtcacaa ggtagactgt ccacccttcc ttcttcaggt ccttaatcaa gcgggagaag    93480
atgaaagggc tcgcattaaa cgttccatca aagtcaatgg ctatgatatg tgtgccgtgg    93540
cgagtctcat atggattgct cgtggtaaga ttgctgtagt taaaaggcac ttcttccccg    93600
cagtagctgt agtccatatt cacaccttct cgttaataaa tttacgggcg gtttggtgag    93660
ttgtttctgc tgtcttcaga ataatattaa ttttattgtc aagatcattc atctccgcag    93720
ttaattcagg aatctctcca gcatgcatgg tgaaatcata catagacatg cctagaatct    93780
cgttaatgcg gcggttgcat tctgcagcac gctggttcat tttccacgct aacaccaaag    93840
cctcctgtgt ggcttctaat gcaaagtcta atacgtcggc ctcttctttc gtcatctcag    93900
tctctcctgt ttattgttga taggtgcatg aatgccttat aactaactct ttattcaaat    93960
tgcaatagca agtccaccac cgcgctaggt ctgtcaacaa actccccagg cccacatgcc    94020
catagagggt atccgtccac atacctccat atccaacctg aagtgtggag ctcaagaagg    94080
gcagtaccgt cctcactgtc aaccactctt tcccacagtg ttgggcagcg aagcttgagg    94140
atcggatccc cgcccttata cccatccatg tagatacccca ttgcaaagtt cagcatcatc    94200
tttttgtgca ctgacctctt actgagggtg ctcatcactt cctccttgtg gatgtttgta    94260
agcttctcct tggctacctg cagatcgttg cagccattgt tcaggagatc ttccagacac    94320
tttaccctaa ggtcgtggat atctttgtcg tgcaccgttg gtacagggtc gtagcgtat    94380 agcactgttg atacaaggtt gctagggtgt gggtctgaca gcagcccata accccaatac    94440
```

| | | | | | |
|---|---|---|---|---|---|
| tcttctgtat | ctgaaaggac | aagacaccca | atatctctgt | caagctttcc | tgtgttgtaa | 94500
| gccacattga | ccgccatgat | tatagctcca | ctaacaaagt | gctttcaaaa | tgcctctcat | 94560
| gcagaccgct | ataaggaacc | acttccacaa | caccgtcgcg | gatatatgga | gtcatcatgg | 94620
| caacataatc | accgaatggg | ttggcattat | cactaaccac | aaccacatgc | tgcccctcct | 94680
| tggcagagtg | ccagatagat | ctgcatttca | tcatgtgttc | gagagcgcca | ggtaaaatct | 94740
| tgttacgttc | tttacgggtc | ttcataaaag | gtatagctcc | ttatgaaagt | gggctttcaa | 94800
| tttctcaccg | agaaacttct | tgataccttc | ctctaaggtg | ttttcgatgt | agtccagctt | 94860
| aactgcttcg | atggacatat | catagatcgc | cagctctaag | ctgtcaagtc | ccatcatagc | 94920
| atgaaccata | agattttcat | cttcagatac | attcagggga | ctacctataa | catctggggg | 94980
| cagaatagtt | tcccaattat | tctgggtggt | agatctctcg | ccatccacct | tacgtcgcag | 95040
| ctcgaaggtg | tttttagtgt | aaaacacttc | ataagaaacg | atacgactgt | cgctctcgta | 95100
| ataaacgaag | ttcaggtagg | atccgagccg | tagtcggcaa | acttctactc | caaaccattg | 95160
| tttcttataa | gaattcagac | tgatgctttc | gcattcacgt | ttgctcaaca | cggctctctc | 95220
| cttttgttaa | tcttcgtaaa | tcaggatctc | tgctttaggt | tttcgtgctt | tcaggtccag | 95280
| ctctatccag | tgcaccacag | ctgtttcaag | aaaaacagcc | tgtatacatc | cgtcttcagc | 95340
| gtgtcctacc | aacataacaa | gatcttcacc | ttcgtcatct | tcatcacgaa | catacagaat | 95400
| ctctccggac | tcaaagtctt | ttacaacctg | attattagat | aatttacgaa | ttttttgccat | 95460
| attagaatcc | ctctacaaag | ctcttgtaga | aaacaatctc | agtatctaca | ccagtcacga | 95520
| tcttgtcgtt | cctgatttca | tctgtaagat | aggtatcaaa | acgcagaacc | tgtgtggtgt | 95580
| tgtcacacat | ccactcggct | gtaaccatgg | cgaaaatctt | agcatcttca | ttgtccggtg | 95640
| tgaatgttac | atttaaactt | ttcgataggc | tgcgtgttag | ctttcggttc | tgcaatggtg | 95700
| attttttgtgg | tcattactct | tcctccatag | tttcaccaaa | tacttcgata | cgagcgtcaa | 95760
| gctctgttgc | tttcagctct | ccaacaaaat | cttttagttc | tttctcgtca | agatcgtatg | 95820
| cccacacaca | agatgagcat | gcagatttca | cgattagtag | tgtagataca | cggcctgact | 95880
| ctgtaatcat | gctcacaatg | gttcctacag | ggaacgtgtt | gatagctttt | ttaactgggc | 95940
| gttcagattt | aattactact | tctgttgcca | tgaataacat | cctcccttat | ttggcgtact | 96000
| cgattaattc | tacagttttc | ccaaagctcg | ggatataatt | tttattatac | ccttcggtga | 96060
| gaacccataa | agtatcgtac | ttttttccact | tgttgtcaac | agccttttgt | tcaaagttat | 96120
| gctcaaagta | taggtcggtc | aggacgatga | catcttttgc | atttggtatg | ttagcgtcca | 96180
| gatactcgaa | cacgcaagcg | gctgttgtgc | cccatgttga | gtggacctca | tagttaatca | 96240
| tctcatcgat | gtttccgcga | gtgtatactt | taacctctcc | aacctcggtt | gaccaacaga | 96300
| acatcgtaac | cttgaactct | ttatatagat | tgcacaaccc | agtgatctca | ttgaacattt | 96360
| tctttaaagt | tctttgtgag | atcgacccag | aaacgtctaa | agccaccaca | atatctatag | 96420
| tgttttccgg | attacgacca | ggaacaacaa | cgtgctgatt | cttttttata | gccccaactt | 96480
| ttcgcattgt | gctggtcaaa | gatccagatc | ggcgaccggg | ttttctgtag | gttagttcag | 96540
| cctttcgttt | agacaacata | cgttgcttaa | tgatgtctat | ataattgatt | acaggcttac | 96600
| ccctgttctt | gacaaactca | cgcaccgcct | ctgggcaacg | acctccagaa | gcttgcattg | 96660
| ctgcttccaa | catgtcacca | gagtcctgca | tggcttgatc | tttatcagat | tgactgatca | 96720
| ctggttgtgg | ctgatcatac | cccatcgcct | ttccaagatc | atcaccagtg | ccaccgttcc | 96780
| cacttatgtg | atcatcggtt | tgtcgtttat | ctccttgaga | gttctcgcct | ttaccgttct | 96840

```
tacttttacc gctattctga tctctttgct tatcaagaac cgcatagacg ttctcagcaa    96900
tccatccatg gaacctcatg tcacagtagc aactggctaa gaagccaaaa ggcttacctt    96960
ttacgaactc cgtgcttttc cccttcggga agaaaacaca aggaggcttg ctaaagtcaa    97020
ccacaagacc tgtgttgata acgtgatcac aagcaatatt gaacagttcc ggctcaaagc    97080
ttttaccacg gaccaaatga tcacagataa tatgccccac ctcatgtgac agaagaaagg    97140
ccacctcttt cacagatttt ggggaataga aacctcagc catctcaaac tgcttgtcag    97200
tcagagatgc tttaagaatg gttttacgct catctgccaa ccccataatg aactcagggc    97260
tgtagtagat gcgtttatgg tctgttgcca tagtggagca ccatgtgtgg ttttctacga    97320
actgcaaccc tgacaacagt gtgccataaa acggcagctt tcaagaagg tacatgcgag     97380 ctgcctgcag cattcgcaag gcatcatctt tttgtgcggc aatgatttct gaacttctgc    97440
tatccattaa aactccagaa ggggcctttg gcccctgtca ttatttaacg tgcttgaaaa    97500
taccagccaa ctcggtcatt gtcatgcgag tggtcttcat aaggtctgtc atagccttct    97560
ccatgattgg agatactacc atgaagttcc ctttggtgaa acctttgttc cagtcggtaa    97620
ctaatagtgt tttaagtccg gccccgagac gctcaccagt taaagcacaa cattttcgaa    97680
tgtacgtgct cttaaattga ctgaatgaca gatcaacttt catacctgca tcgtagaacg    97740
tctgacaata gaaagtgtaa gctttggcaa tctcaacatc gtcaggcagt gcagaaacct    97800
cttctgtaag ctcttcttcg acctttttgag gctctttttc ctcttcgtga gcctgttgcg    97860
tcatttcttc aatctcttct gttacaggct catttacgat gtcggaaatg tgcttgttgg    97920
cttcacgatt agccatgaag ttttttaaaat cctgcattgg tgacatatct tcctcccatt    97980
cttcgtcaaa gagtgccagt ttatcctctt ccgttccata ttgcaagatg aaatcttcaa    98040
aagtgtaatc acctttcaat ttctccatgc gctcttcgct caggtggagc atcatctgct    98100
gaacaatttt tcgatcagtt ttgtctttaa tcaagactgc ggtctttta tctaccagac      98160 agtccttcag aaagttgcac ctcaacccta ccacacaaca gttatcaatt gcgtaaggac    98220
cttcatcatc tatccgctct aaggatgggt agaaaggatt cccaagcccg ttttcatctg    98280
tgtgcatgtc aaaaggtata agggtatagt cgcacactcc ctctcctaaa agttttttac    98340
caaataggag gtattcttcc catgacaggt tgaactctat atctcgtttc cgtgcattat    98400
tctgtttgcg tctatatttt ttgagcaggc gctctaactc ttctggtgta taatatttt     98460 caatatccat gagttgtctc ttgtgctctg taggtgaaga aatcctatca agcgcctcaa    98520
cagatgtcaa cctcaaaaac gggttgactt tactctaaat ccacgatata gtgcacccat    98580
tcgaaagaaa acgaacacag gagcacttaa tcatggcaaa tcttaacagc tttagcactc    98640
ggtgaaaaca agatatcaca accaatctct cagcaggtga tatcctttct gcaatttacg    98700
aggctttgga tgataaagct acttcaaaat cggtttgtac caacccgtta attcctatag    98760
taatgaaggt gattgagcgt aggctggtat ccggatctga taagtggaca tatctggata    98820
atggaggcca cacttactcc aacggctatg tcgatataaa agtagaatat gcggtatcat    98880
atcgccggag cggctctgta actttcaact tctctggtgg tttccgatct ctggcaactt    98940
caccttttgt ttcctcagag gagaagtttg aacttccgtt cctttggatg atggctaacg    99000
cgacaggcaa aaccccctgta agcattcgcg taaaatacaa ctacaacgga tctagtaaga    99060
tctatgccga gagtgtctca gcaagttttt attttgtgat gggggatgga atcctcaaac    99120
atataaaaat gtgtgatatg catgatgtta taaatgaagt gactgataag aatgttctgg    99180
```

```
tgaaggatct caacaatttt tatacaccag gagactatta cgtcaaccgt ccactgtgca    99240
tctttaatgc tgcacaccct ttaggtgagt atttgattgc caatagtgat attgccaata    99300
acctcttcga gttagcaaga gtacagaatg aggtgttgac atcttgcaag agcggtgata    99360
agtttaccga agaagagatg ggtgttttag agatgatggg atataagtgt agcctttggg    99420
tagatgaggt gtttaatgac ggcatctatg acaggatat ctacccgtta aagaagtata     99480
ctgattccag tctaatttac gcggagattt gactatgatg aagtcatgtg gtagtgtata    99540
ttatgttggt gagaatgttc aggcagatag tgtgtggaaa tccattaagt ccaccaccga    99600
tgatgccttc ttgagcgggt tatgtttccc caatcccaga gacattctcc ctcaccctgg    99660
ggattttgtt gtcaacaaga ctgacggcta tactgtgtgc ctgatggttg aaaaaatctt    99720
tttagacact agacacaatc accgtcttgt gttaaaattt caagaatgta aaatgacagt    99780
tgcctaagga ggcctaccaa tgtctaaaat tacttatcgt gcagctattt actgcaatga    99840
gcaaccaatc aacagtgatg gtcactgctt ttttaaagaa aatcagttgg gctgtattgt    99900
cctccctgat gaaggggaag gctatatgat tgcattgaca gggtttgagc ctgaagcttt    99960
ggaagccaat ctggactatc tggtagaaga gggtgctgca gacctggttg ccaatggcct   100020
ctccataagc cttgacgaag tggagcgctt catgggaaat taccgtgtag tgcgtgagtt   100080
tactatcgag gtggaaactc cagagtgggg tagcactgaa actaatgctg aagaaaaga    100140 agaggggta gaataatgaa agtgcaaatc ttaactaatg ccgagaagat gtttatcgaa     100200
gatacgcctt tgaaactgg tgagctacag tttgtatatt tgttgactt agataaggtt      100260 tttcctgcgc tgaatctagg tttggagaaa gtaccttata aaaccctatg ccaagttgtc   100320
cgtgccttag cggcagatgg ggagttccac acccttgaag atatccagac ctacgggtat   100380
cttgaactgc aacgagaaga agaggtgaac tgataatggc ccagtggaag acaacagttg   100440
accttcatga tcagtggtta ggacgcataa ctgaagacgg gaaactggta gagtgggaca   100500
acaagcatgt tagcgagttg gcaagtattg tggctggcaa gttacgctcc aagttccctg   100560
aacaactgaa tcctgatagc tcaaagttcg atcctgagtt ggaggatgtt gtatactact   100620
tcgataccgt tgatgactac gacgcgtggt ttgcagcaca ggagctttac ccacaaggct   100680
ctgctatgcg ccagatggaa gaagattatc ctccgtgtga gcaattcaat agtgcaatga   100740
cttgcctcta cgattgggca gataagaacc ttgtctggat tcggactgca ttttagtggg   100800
cagggatggc ggcaaggatg ctgcttaagg agtagtagag atgttatacc agcagtacga   100860
acttcgtgca gaaaaagaat taaattttga caaagatatt cacagatatt attatggaa    100920 agttagaggg caagcaagaa agtgtactcc aacactcttt tatgccagca gacgactagc   100980
gccagaagag gcaacagcag aaagggttgc atatggctgg aaagttgcgt atgatattga   101040
cagatccgat gtgatgtctg ttttggaaaa ctttgaaaac acttacacac aagtagagga   101100
cttttactaa tgtcaagaaa cgtattcgaa agtggtcaaa tcactgtccg cgagttgcca   101160
gctattattc aatttgccca gcgtcataac cgatctgtcc tgattttggg accgatgggt   101220
gtggggaaga gccaggtgat gaagcagatt gctgataata tgttcggtga gcgagatgac   101280
aacctggttg acgtgcggct gtcagataaa gatcctgctg acttatccgg actgcctatc   101340
cctgtagagt cagatggaac tacacgcaca gtgtttgcaa ttccagaatt ttggcctgca   101400
gattcggact ggagcggaat tatctttctg tgatgagctta ctcatgcaga taactacttg   101460
cagaaggttg caatgcaaat tatgctcgac cacaagtgcg gcacctatgc atttcctaag   101520
ggatctgttt ttgtagctgc aggtaaccgt gctacagatg gtgctgttct ttcagcgctc   101580
```

```
gaagctcctc tggctaaccg ctttatcatt gtagaagtta caagcaatgc agaggtattt    101640
attgaggact acgcattcct taatggtgtg cattcctctg taattggata tctgaaaaga    101700
gttccatcag ctatcgataa ttatgaggct atggctgaga ttaattgtcc gtcttttgcc    101760
acaccgcgat cttgggttgc tgcatctgac atcttgcacg attttgacag cggtattatt    101820
tctgacgcta tggctcgtgt tcttctgcaa ggtgctattg gtcacactgc agcggtagaa    101880
atctggacct accacaccaa gaaacgaaac ttgccagaaa tcggtcggat tatggcaggg    101940
ggttgcaaag aatatgtagg ccctaagcag ccagatatct gtggattct tgggtctgaa     102000 ggttgtattg ctattcggaa tatgatggaa aatgcaagtg tctcagacga agatcttgtt    102060
agctgcgtgg caaacttcct cgatttcctt tgggaaaatt tcaaagatga aaccgagac    102120 tttgtattct cagtctttat ggcgatgatg aagcccaacg ccctgggaaa tgccttactt    102180
attggtaaag gccgggacaa gatcgttgct cagctgatca aagcatatcc aaacctgatg    102240
aagattgtaa aagagtttgg tgaagagttt agcgccattt tagctaaagc ttgaggaggt    102300
tgtatggcta aagtaggtaa gcggggaaac tacttggtgg tattgaccga ggagccggag    102360
aaggagtacg aatgcagctc cacttgcgtg atcgatatcc gagaaaaaga tgtagatgaa    102420
atctggttta aaatattgga cgcttgcgac agcagtgact atttcttcat ctatgtcaac    102480
gataaagcgg ggttcttcca tgacgatgga gagttaccgt atgaaatcta tgaacttgta    102540
gaggcttgcc atcgtggaga tgcggagttg tttggtctac ggctgaaaag tggtaagttc    102600
ttctaccaag acgaatgcat gaatcttcac aacttcgtag agggaacttg caacgatgga    102660
gagattctgg cacactacga ctaatttcta agaccacccc cgcttcggcg ggatttttct    102720
atttggagtt attgtgaaaa ttaaaatctt tgctattatt ttgagcgcat ttttatcgct    102780
gcctgttgtt gcagcaccaa acaaaaagt atatcacacc tgcaagccat cggatactaa     102840
ggaaaacatt ctagcatgca atatctacag ggaggctaga ggggatggca cgatgggtat    102900
gctggcatca gggtttgcca cactaaacag gaaatctcat cccaaatacc cggacaccat    102960
aagaaagatt gtctaccaac ctaatcagtt ttcgtggaca aaccacggca aaacttttaa    103020
ggtgacagaa aaagattcat gggatcacgc taaaagtctt gcaaagatgc ttctaaaggt    103080
atataataac aaccatgttg catacatggc tatggatata acaggcggag caacacacta    103140
tcatacaaca aaagtacgac cggaatgggc aaaaaagatg cagaggacag ctcaattcgg    103200
gagtcatatc tactacaagg agcgcaataa atgattgtaa acagtaatga aactaaagca    103260
gtgctaacgg ggaatttgga ggtcacaagg ggatcaattt ctctgaacaa agagactttt    103320
gggttaatca ttaaagggat ttatgaagat aaggtgctgg caagctgccg tgaaccaatc    103380
ttcaatgctg tggactctca tgttgagtct ggacggggtg atgtaccgat catcattcac    103440
tctcctacag atcttgaacc atacttcttt gtgcaggacg ttggcctcgg tatgtcagaa    103500
gagatggtcc gaaacacttt catgaacctc ggtgagtcaa ccaagcgcaa cagcaacgct    103560
ctggtaggca ataaaggtgt tggttcaaag gccccgttca gcatggtaga cactttcgat    103620
gtaatcagtg tgcacaatgg tgtggaaagc acatatctac tgttcttgga tcagggcatc    103680
ccaaatgtca ccaagatccg tgagcggaag actgaagagc acaatgggt aaaagttcag     103740 tttcatgtta agaaagagca tgttctgaaa tatcgcaccg ctattgcatc atgtctgcgc    103800
tatgcaaaat ttccgttcac tgtcaccgat ccgatgacga gcaagatgct ggagggagac    103860
aaagtagagg cgcagtatta ttatgaaaaa gatggttgga agatgaccat cctgaagggc    103920
```

```
tataccaacc agctctgacg agagtcgtgt ggtaatgggt caccaacctt accgttctaa   103980
gttcctggaa acactaacag attatcctgc aatttgtgta gagatcccta tcggagactg   104040
caatattaac ccagggcgtg aatggaccat agaaggtcac gatgatggtg gattccaaga   104100
gcgtttggaa gcttttgtca agaaggtat  tcgccttcgt ggagcagaag ttgttgcaga   104160
actggagaca gcaaaaacat cctcagaagc acgcgagatg atgaagaaca gtggagtgtt   104220
cgggcacatt ttcggtaaga attttatgta taaccgttgg gaagaaacag ggttaggtag   104280
tttgggggac tgcgagatct tcgcgggtgg cttaaataaa ggccgcatag gctacgcttg   104340
ttacggaaag gtagaattct tacgaggagt ctatttagta tttaacgacg gagacggtaa   104400
atataaccga aataagtgta actacttaag cgagatcacc ggacgcaacg ttttctattg   104460
ccggaacacg gatctggtaa aagagtttaa agaggcggca caccatccgt tctttgcaga   104520
tacggtcaaa ttgttatcag agctccctcg ccgacctgtg aagaaaggtg aaacaaaaac   104580
tcgttatgag cccggttatt gggttaaaaa acttgagaag gatggttact tccgtcgtga   104640
gcgtattacc aaggcagagt tcaggaagat taagcactgc ataccgtatg agggggatat   104700
ccaacgggga agttgttggc tagggcagat gagtaacatc taccagcaaa attatgaccg   104760
tgtgcgtgcg gcactccaaa tccctgaagg ggaagatctg tacctggtat cagaatctcg   104820
tctgcttttgg actgatccta attgccaata tgttacagag aagaatgtgg aacatttgct   104880
gaaagaggat gcttggaaat tcttactgac tcgcgcagca aatgaaactt catatgcacag  104940
cctgtacaga cagttaggta aaattatacc catgcaggat tttggaaatt atcggccaca   105000
ttttcacaag tgggaaggta gcaccacgtg gaagtacggt gagctgaatc atcgtgccaa   105060
agtcttaatc gccaaccgag ttaagtgcgg gaaggcctat attgcgagat tggaaaagaa   105120
atatccgctt ttgaagcatg taggcttgaa atattgggac actcctgcta tgattgaata   105180
ccgtgaactg attgatacaa agaataacat caaataagga gaccaagatg attttcatct   105240
acgaacattt caaaacccgt aaagaagcac gagaccgccg tgcagaactt gagaagaagg   105300
gtttcacatg cgctattgag aaaggtaaca aacctggac  actggcagtg ggtgccccag   105360
aggtgttcga tcctgaccgt gacagcgttt gttacacccg tgaggatttt gaaacccgtg   105420
aagaggcccg tttatttcga tatgggctgg aagataacgg taagtacgcc atgatcttag   105480
acttaggcga aggttccgtt aaacgttggg gcgtggtata tccactgtgt gttgttcacg   105540
gtgtagggtt cactggggta gcaatcaaat cagaagagcc ttcggtagaa gtcaaagatc   105600
cggtgctgga ggtggtgagt agtgtgtctc aacaacaatc acgaagcatc gagccccttag  105660
tggttatttg cggggaactc ctccagatca cctgcaacga aggtattttt gaaattcgcc   105720
gtagcgaaag tgaggaagtt taccagaaag tcttcgacca tatctctgtt taggaatatg   105780
acgaggcaat tggtgaaatc cttatctggc tggaacgcaa gaatgagttc actacactgg   105840
cagacaacct gatcatgaaa gatggtaagc tctactacta cggtgtagag atgcgatcta   105900
ccattgcaaa gaaaattgag aaagattatg cagatggaac actggatgac cgttatgtga   105960
aattcctagt tcgcctgtta cgcaatccgt ctgcaaaatc tgtaaacatg ctctacgatt   106020
ttatgcaggc aaacgacatt cagattgcag aagatggtcg aatcatttgc tacaaagggg   106080
ttcagtttaa cggcgacaag tgggtggatt ggcacagtgg taaagtccca caataccagg   106140
gagcttttgt atccatgcct cgtaactttg tagaggatga tccggaagct gcatgctctt   106200
atggcctgca ctgtgccagc aaagagtatg caaagagcta cggcactgtg atgacggtta   106260
tggttgaccc tgctgatgta gtcagtgtac cttaccaaca caacagcgct aagtgccgtg   106320
```

```
catgccgcta cgaaatcgta gtagctccag aatcgcgcaa agatggagac ccaatcgagt  106380
acgtggttga ccgcgacggc aacactatcg acattatcta cgaggaggcg taatggaaaa  106440
agggcagtac gatgtaggca cagatgctgc ccttgttgca atcatgagtg gtgagaatgt  106500
cttcgtaagt ggaccgggtg gaaccgggaa gacatatctt atcaacatga tccagtctat  106560
gtatggagac tcttgcataa cggttgcccc gacagggta gccgctttaa acgttaatgg  106620
agcaacagcg caccgaactt tcgatcttgc cgcaggtgtg agcatggagt cagactggac  106680
agcaataagg gcaaaaacag caaagcctct gaaaagcaag gcatttacca tcctaattat  106740
cgatgaaatc tctatgatcc gtgctgacaa gttcatagag atggatagaa aacttcgctt  106800
tcttcggaaa aatgacaaac cttttggagg cattcaggta ctattgtttg gagatttcta  106860
ccaagcacct ccagttgtct cttccatgga gaaagaagcc tacttcaact tctaccacac  106920
agatctgtgt tgctatacag aatcttggga ggatcttaat cttcacaata tagccttagt  106980
agaccagttc cgtcaggaat ctgttcgctt cgccacaatg ttgaactgtg ttcgtgaagg  107040
tcgtcgcata aaagaggttg tagcagagct taacactcgt tgctatcatg gcggtgtccc  107100
aacagatgcc ttgaccatct gcgccaccaa taagcaagca gaggaggtga acagacgttt  107160
ctatgatgcc atccaggccc cagagaagac ctacattggt aaaatgaaag gtaaattccc  107220
ttccacacta cctgtggagc aggaaatgag gctgaagata gggatgaagg ttatgataac  107280
ctcaaacgat gttgacccta ctcacaaagt tccgtattat gtcaacggga cacgtgccac  107340
agtggtaaaa ttcaagacca aatccgtggt agttgagcta aagacggga cacaggtcga  107400
aattgagccg agattgtggg agaataacga gtacaaacct tcccagaggt acaatattgc  107460
cgaaaggaag atggagaagt tcatagagag ggttgtgatc gggtcttatg agcaactccc  107520
tttgaaatct gggtacgcag taacatcgca taaaagtcaa ggacttacgc tagattgtta  107580
caacctggac tcggaaaga acggagcttt ctctcccgga atgacgtatg ttgccttgag  107640
tcgggttaag acgatacaag gaataaactt gttgcgtcca ttaagagagg tggatattat  107700
tgttgacccg cgagtcgtag agtttttataa tacaactttc cctggcttag acgaaaagt  107760
caggaaagat tttgaaacta gagcagaaaa ggggggacgta tgagtttgtg gagaaatata  107820
gttaactacg tgtgtggcaa tccaaatcct gaagagaagg ctgttgtgat tcacgatttt  107880
actaaaagat ctcgtgaaaa agacctcctg ctaacaaagg tgatcgataa agaccctgta  107940
ggggactggg cagggtttgc gtttacatct gacaaataca ccttttaacaa aggtgactac  108000
cttgttgtgg atttttaacga agacatcgag ggtgctgaac cttactatca gacccttatc  108060
gttgcggagt gtgttgagct ctctgcaaac atgcacagtt tgattctttt tgagcttgac  108120
tctgaagacc ttcagtagtt agtaagacgt gagtataaag gggaggaact cctccccaca  108180
aaactgggga gagcaccaaa cgacgagcaa aaccaaatta gagcttacct ggataggtaa  108240
aaacgagcgc aaaaagttag agccgcacat tttattagaa gattctagca ggtcttaccg  108300
cagccagaaa gtgaccgaaa acgatatttt tgataataaa ctgattttg gagataactt  108360
attagcattg aaggcgctag agcaagagta tgcaggcaaa gtgaagtgtg tttacataga  108420
cccgccattc aataccggga gggcttttga gcactacgat gacagcctgg agcactccat  108480
ttggctgggc ttaatgcggg acaggttaga aataattcgt aatctgctaa gcgatgatgg  108540
agtaatattc gttcacttag atgactgcga aatggcttat ttaaaagttt tgatggacga  108600
gattttggt cgtgcaaatc agttaaatac catatcgatg accacaaact gtccttcagg  108660
```

```
ctttaaggca acaggaactg cagttttctc cacagcaaac ttttttgcttg tatatgcaaa   108720
agatcgtacc aagaagccgc ttaacaaaat ctatatacct aaaggatatg atacgggata   108780
taacaaatat ctattaaacc cggatgacca ttataaaagt tggacgtggt gcggtattgc   108840
cgatgcgttt gcaaaggcca atggctataa agatacaaaa gaggccaaga aaaaactgcc   108900
tgatacattt gatgatgaat tagcacaatt tgcaattgat aatgcagaac gtgtatttca   108960
atccgttgca atcggcggtg gtgctaagat aaagagaaaa gaaactatcg agaagtcaaa   109020
gaaagacaga gataaggttt atgtacatcc aaatgaggat gtcgaaggct tttatattgt   109080
aaatggcagg caaatggtat tttactctaa taggcttttg gaaattgacg gtgagatgca   109140
gcctgctgaa ctaataactg atgtttggac tgacattagt tggaatggaa tagcaaatga   109200
aggaggcgtt agtttcaaaa atgggaaaaa acccgaagcg cttttaaagc ggattttcga   109260
aatgtgtacg cgagaagggg atttagtctt ggattcgttc ggcggttcag gaactactgc   109320
tgctgtagct cacaagatga aaagacgttg gatttcggtc gagctaggtg atcattgtca   109380
tacccatatc atcccgcgct tgcaaaaagt gatcgatggc gaagatcaaa gtggtatttc   109440
taaatctgta aactggcacg gtggcggggg cttcgctat tataaacttg ccccgaactt   109500
ggttgtgaaa gataagtttg actcagaaga agatttagag taatatttaa aacattgaag   109560
gggaggtcta ctctccacac aagataagga gaacaccgaa tgatgaagcg ttataaacca   109620
tacacttttg aaatcgattt cgaacttgac gatatgctca ctgtagaggc tcaggcagtt   109680
gtccagttgc cagatccgga gtgccgtgat tctgatgttg attattatgg atttagacaa   109740
attaccgatt tacatgtcta ccacaacgga gaagaggtgg actttcatca actaccaaac   109800
gatctgcgac actcgattta caaacgtgca gcccgtgaac tagagtccta tctggatgca   109860
gctacgacag cagctgcatt tgccgaagaa gtgggaggtt tctgatgatt acaggtgtga   109920
agattatcca ataccactta accaagttgg aagatgctga gaaagagctt gcagaagttc   109980
tgaatagtgg gtatactttg ctatcatgcg cctgctcaga cacctacgct gtgtggacac   110040
ttatccggaa ggaagagcct gcagggatct tggtgccaaa ccctaagatt attagtgagg   110100
tggatgacta tccccaggac ggcctgccag aaggctggga agtatgggaa ggtggtgaaa   110160
accctgcacc aggtaagtgg gtaaaataca aactacgtag tggtgcacag tacgctgact   110220
actctgatga cctagactgg agtcattctt caccaggatc atctgcaagt tcatatgata   110280
tcgttgcttt tcaggaataa ggagagggtg ttatgtcaga ttttatgtgg aaagtaggct   110340
atgccactcc tgaaatgtgc gaggcttgct ttgtgaaaat aggccgcgag gatatcgaca   110400
aagtgatcct taagtttcgt gatgtggctg tgatcggcaa ccgagtgctt aagcacttaa   110460
agaatttgaa gctcaccaaa aagaagttct tcgggatttt cgaagagaaa gttgatgctt   110520
ggacccattg cattcaggaa gctaaatctc actacagtgc tatcgttact ccagaacggg   110580
tagctaagat ggaaggattc attaacagca cagaatttga gtgtctgaaa gctgcactcg   110640
atagttatcc gaaatgcctt aagcacttgg acaagtatgc agaaaaggat ggggaaatgt   110700
atctaaccct ggacgcatat tatgagatgc aagaaatttt aaatttagat ttgacattgg   110760
tatccaccga gtatacaata ggtatccggg tttaacacta ggccctgccc gaaagggtgg   110820
ggctttttgc attaggagac agcaaattga aatttatcta caaagaacac taccacaaag   110880
gtgttgtgtg gagtctattt gacgggtccg gtggtgcagt cattgactgg gcaaaagctg   110940
ggtacctgtg cctgtgctt aatgcagaag gcgctgatca cggcagttat gcagaggtga   111000
tcaccgatca tcccaacatt aactatgttg attattggat tgacccatgg ttccctcagg   111060
```

```
aaacttttg catgtatccg gctccagact ttattcttgc atttcctccg tgcacgcatt    111120
tagcggtatc aggtgctgca cattttaaga aaaagctggc taaggacccc atgatccaaa    111180
ttaatgctgt aaaggatgct cgggttgcgg aagagctggg agagatttac gattgcccgt    111240
ggcatgtaga gaatcctgtg ggtgttatgt ccacactgtg gcgcaaacct gattaccgtt    111300
ttcacccttc ggattatggc gggtatttac cggaagatga tgtaaaccca tggtttcctg    111360
aatttatagc tccacgtgat gcctatccaa aaataacttg cggatggata ggtaatggat    111420
ttataatccc ggccacaaaa cctgtcccgc aaatagttga cgtggttagc gggtattcca    111480
tgcaacacgc caagctgggt ggaaagagtg caagaacgaa gatgattcga agcctcacac    111540
cacgtggctg ggcaaaagct gtattcttag caaacgagcc tgtagtaagg agcagaatta    111600
atgggaagta aattcatggc atctgcatac aaccgtttcg gtgagccaaa cccgaaagca    111660
actaagtata aaagtgggggg aagtgtgaaa cgagactatc gtgatgaaaa agaagttgaa    111720
actgtagaga ctgttttaga aaatactaaa attgtccctg tcccacaaca aaatatcggt    111780
ctgatggctg cacaatattt tggtgtgcga tcagcattat cccaagaaga cggtgtgaca    111840
gtcactgcaa catatttccc atattacgac cgctacggaa atctgtccgg tttcaaaaag    111900
cgtgactgga cgattcctaa agagcaaagg ggccatttct ccgttgttgg catagtaaag    111960
gccaactccc agatgtttgg gcaaaagctg tgtgcatctt ccaacaaccg taagcaaatt    112020
aacgtttgtg aggggggaagg tgatgttatt gcagcatggc aggctgcata tcagatacag    112080
gtaaaaggga ttctcaccaa cgctaaagcc ccggcaaagg tgaagcagtg ggctaaagag    112140
gtccaggacg ggatcgacgc agttataaac ggtggtgatc tggcaggaaa accctgccta    112200
ccttttgttg gaattaactg tggatgtgca aacgcagtag atactttgc aaacaatgag    112260 aagtttatcc gtagctatgg aacagttgtg ctggcaatgg ataacgatgc agctaacgag    112320
gtagagaagc aaaaacacgt cattaaaggt gttgaggcca cgcacaatat cgcagcattt    112380
ttgatggctg ataacgttta ccacgtagaa taccctggtg aagtaaatga ccctgacggt    112440
gtaaaagata tccgagacat gctgaaggct aaaaagctgg aagatattgt caacatgttc    112500
cggcatcctg ttaaatatgt gcctgatgcg gtgtcggatt tagaagactt ctctatcgag    112560
tctttgcgga aaaagacttc caacggggta gatatcagcg cagagttccc aaaactgcaa    112620
aaaatgctaa aaggcttgca caaagggaca ctagtaatgc ttacaggtcc atcaggtggt    112680
ggtaaaacaa ccgtagctaa aaaactggaa cactgtattg caagatacct aatggacccg    112740
acatgcccga aggctgatga ctatgaagag gatgatcgtc tatgtatgat ccatcttgag    112800
gaggacccag aggaagcaat taactccttg tatgcaaacc agctagggtt tgatgttaaa    112860
gagtttgttg aagatcctag ccagttttta actgatcaag aacacgcaga gattcaccaa    112920
tcatgggcaa aagctggaaa aatcaaagtg ttcaaacatt tcgggtctat tccggtggat    112980
gagttgatta ccaagcttaa gcaaatggtt tgcctgtacc attgccgtta tattgtgctg    113040
gatcacctgt ccatggtaat ttcagggctt aatgttaagg atgagcgaaa agaactggac    113100
atggctatga ctcagctggc tgcgttttgt aagcagttta acgtgtttat cttggtgatc    113160
gctcacctca aacgtacaga gattgtgcct cctaaggaca aggatggtaa cccgttacct    113220
ttctggtatc ctgtgcgaaa agagaatttg cgaggatcgg cggggcttga acagttgagt    113280
tgggtagtca taggtgtcga ggccgaagaa atggtggatc gttctcgtgg acgtgtccgt    113340
ctggtaggtc ttaaaaaccg tccagcaaaa actctaggta ttgctgacac tttggttatg    113400
```

```
gacccgcaca caggtaagtt ccatgatgcc agtaattggt actgggacaa agaaatgcaa    113460
atgtttacag acgagaagg tggggaggtt gtttggagac ctcaggctat gtttgaggat    113520
caggagcatg cagttgtaga aacacctatg ggcaaggttg tggctgataa ggttgtaact    113580
cctactgtta agcctgttga cacgcaggaa gacctccagt acgatgatcc atcctctgac    113640
caggttcctg gttttgagga tgatgaaacg ccttttttaat gtttaacaaa gagtgggagg    113700
ggtagtacaa ccgcctcccc tttaaggaga actgtatatg agcatgtggt cgttcgattt    113760
tgagtcatcc ggtttgctgg aagacccaga tctttattat cactgcggtc tgtttaaaga    113820
gctgaataag aaccgtttta tgctgttcct tcctctaaat gaccgcacac actactccga    113880
ggaggatata gagaaggcta agaactttat tctggcaaag aaaactcttt ataaagattt    113940
tgaagttcgc atagcagatt tttcggagtt ggaaggttgg ctcacaggca attccgactg    114000
gtcaccaaca gctttgaact gccataactg ctacagttat gactttatgc tgatggaaag    114060
attatccggt attcattttg atatgttccg tgatcctaaa tgtatgggga ctatcaacga    114120
ccaccaggtt aacctgtttg atacgttggc gatgagccga atcttatggc ctgatcgccc    114180
tttaccaaaa ggttgtcctg actccgtatt caacccggtt actaagaaaa tgcagcctgt    114240
tggtcctcac ggccttatgg catggggcta cgcccttggt aaccagaaag ttcaaattga    114300
tgactggcgc gatcttccgc tgtggaagta tgtggatcgt gtattcgagg acgttatcat    114360
ccaggagctg ctctggaaag agctggtagc ggaatcaaaa ggtgtattct acggcaaatc    114420
tgacatgcag aactttatgt acgatcctgc caaagagaag ccgaaagggt tcaagaagat    114480
cacctggaag aacgcattgc gccggggtat gctgcaacac ttcctgatgg agctgcaggc    114540
ccgtcagggt gtgtattttg acatagatgg ggctattgct ttacgtgacc gttgcgatgc    114600
gtggatgaaa gaaatcgctg atcgtgttga accacaacta cctttaaaag agctgtcaat    114660
gtctcagcgg cccaagttcc ctgaaaagcc gtttaaccaa gatgggacaa tctccaataa    114720
tggttggaaa tggttaaaag ataagcttgg ctatcctgtg gacatgagcg ctttagagtt    114780
caaagcccca cctaagcgag catttacctc cacaggggat gtcagtaaga tggggataaa    114840
atggtgtgaa gagatgggct gtaaagaccc tgataagatg gctgatttct tgaggggcta    114900
tattaagggc acttccacac cacaacccttt acctaaagag ctaatggatc aggcaataag    114960
tgacctacag cagaagcgaa tgcctgactg caagatacct atgaaaatca gcaatcagga    115020
cgacatcaag cgatacctga tcagtgctgg ttggcttccg acaatgtgga gaactaagga    115080
tgtaactaaa gacagcaaga agaaagctct acctgatgca gatgttgatg cacgagtata    115140
tgcatatatg gacgagcttt tagagtcaga gtattgtgac ctgattatca acttctggaa    115200
caaaactgat gctaagttcc agacaaccgt gcacaagttc cgaagcttttc ctaactccga    115260
aaggattaaa aaggaagtat tcgggaaaat acgtagaaaa gctagggcac ttattacttc    115320
tccgcaactg aaagatacgt ttggacacct atgccccaat cttgaaaaat tgaacggaga    115380
gatggctaaa gatatcgtct tgtggttatc attgcgaaac cgcagatcgg tacttgatcc    115440
aatcaaggag gataaggttg atactggtct tcttaatcac ccacgtttga agattgacca    115500
taagcttcct gctaaaagtt ctgggttaac aaacacttcc cgacagaaac acagtatttg    115560
tgcgaacatg cctaaaccat ctcctaaagt ggttatgggt aaagagatgc gtagtctgtg    115620
gggtgttcct ccgggatact ttgagatcgg tattgacggg tccaacttag agcagcttat    115680
cggggcttgg ggtgcctttg agttcgacaa cggcctgtat tatgatgttg taagtaacgg    115740
cgatgcacac tgctattcag gagatacaca aattctcaca gagaaagggt ggataaggtt    115800
```

```
tgaagatctt gatcaggaaa cgcaagtgtt ccagtacgat cacaacacct cgtcaatgag 115860
ccttgttact ccactaaact acgttaagcg gagttattgc ggggatatgt atcatttcca 115920
caacagcagc gtggatttta tggttacaga tcaacacaga atgctgactg ttgaccacag 115980
aagcaataaa ttgtttgagg atttggcaaa agacctgaaa gcaggtaaag ggtctaattc 116040
aggaagaagg tttatccatg cggcagagtt ttatgggaat acaaccttat cccctgctca 116100
gattaattta cttattgcta tccacgatga cggaaacttg catacaaata agatggaag 116160 cagcgtatgc agggtccagg ttggaaaggg gagaaaagtt gcaatgcttt tggatacctt 116220
ttctgctcta aatcttgatt atacagagca gtgcggaaaa acaaccaaag gaggtttgct 116280
ggcaagaaga ttccaattcc acgtgccgtc ttgggtgttt aagttttggg acagcaacaa 116340
agatttcacc tatagtttga tggatcttga taaagaatct aaaaacctgt ttatagcttc 116400
tttatctaac tgggacgggt gggtatcttc cgaaggtgga aaagttattt actactccca 116460
ggctgagtgc aggaagaaat ctgtagaagt ggtgtctgcc ttggctactc agtgtggttt 116520
acggaacaac acggtgacaa ttcacagaga gggtcgtgcc gtgcagcaca gaattacaat 116580
tggtagcaaa cagaaagcag gtttactaac actggataaa gatcttgtcg aggtgagtaa 116640 ttcttttggtt tattgcgtca ccgttccctc cggagcgatt attgtaagga gaggtggcaa 116700
ggttgcagtg tgcggcaatt gcaataacgc caaagcctac tctgctgtag caggtaagga 116760
aatttcccgt aacgatggta aacctgtcac gtatggggtt atgtacgggg cacaaaaaga 116820
taaagttgca gatatgctag atatctctcc agaactgggg cagagagtaa ttgacgctct 116880
ctgggatgcc aacccaggcc ttaaggggcg caaagaggat ctggagaaat ctgggaagc 116940 aacaggtaag aaatttatct attcttttga cggccatgcc atctggaccc gctctaaaca 117000
ctctttgctt aatgcatatc agcaaaatgg cggtgcctcg ttgtgcgact tggtcggaat 117060
cctcatgcac caccagatgg tgaagcgtgg atggtatgat gagggtgttc gtcgtattat 117120
ttattaccat gacgaatatc agcttcaagt ccctgacaca cctaagtata agactgtgta 117180
caccttcgac acaattgaag aactggaagc atttaagtcc cagcaggagg ctaaacttca 117240
tgtgttcgac ggtcataagt acaaaaaggc acgcaaggat gaggacggaa acgaagtggt 117300
tgacaaggac ggaaatacgg tatacgatcc tatcttgaac gatgacgaa agcttgaact 117360 tatctggagc cctgtgggcg aaatggtggt gcattgcttc tggcaagctt ctaaaatgat 117420
gggagtcccg ttccagatca caggtgaata cttgtgtggt cgtaattggg gtgattgtca 117480
ctaatgtaaa ctgtcagcac agggaggtgc tgttgagcaa agaggagatt tttatggtag 117540
tagaaccaac aaaaacattt acatccatga ctatccctgt tattatgcag gtggagtgtg 117600
ttcaggtatc tcaagtgtgg cctggcacta aaatcccaac agggcctgat ttctttcagg 117660
taggcaaagt gtacaatgtc tggaaggcac cagattgtta ccctttcatt aaagatgacc 117720
gtggaatgct gtggtatctt ggaaatgatt tgacactgca ccttgggaat gctattattg 117780
cagtattcag acttaacaag aaggagactg atcaatgacg gctttggtta aagctacctt 117840
tgtagaagaa aagatgacag acctgtcatt cttaagaa ggaaagacct acgaggttta 117900
ttacgataaa gctcgtgcaa acaagatgat taaagacgag gaagggattg cctggttat 117960 ctcccatctg gcaaacggtg agtatcatat ctacggaacc accctgcttg ccaagtttgt 118020
agctgttgaa gaggacctat gaaagtaaag tatctggctg agggtatgag taggtatttc 118080
acccttggtg aagaatattg gcccttaca agcaacggcg atgtctacgt gaaagataat 118140
```

```
ttcggcacgc catggttttt gcactctaac gggttagggt attctattta tcgcagtgca   118200
atgagcgaca caacccttgc agagtttgta tagaggaggt agaatgttag taaaaggtac   118260
ccacacagtc aaacaacgta tcgaagttga gatcgatgac tgtgagctga agcatatttt   118320
acgatcatgc tccaacgttt tgctcctcag tattctccag gagcgagctg agaacgagtt   118380
cttaaatgca ctggcaggcc gtcctgggga cttctgtgtg cgtaagcgtg aagatcataa   118440
gtcatggttg tgggaaatcg attccgactg ggattaccac aaaaatgagg gcatagatga   118500
gcctattcgt gaattgacag ataaagagat tcagatgtac aatgaagttt gtcattgggc   118560
aaaacgccaa caaatttacc tcgaccctgc gtggatgatt gaaaatagcc attgacaaga   118620
agtaagattg gatataagat gcttcacaca aacagagcgt tgatttttaa ataactaagg   118680
agactgccaa gatgaaaatt actttgaagc ctctgagctt gacggtgccg atggtgttat   118740
tatagtttct gatggaaagg taacattgac ctctggactg acctatgagg acactaccta   118800
cgcattggga gatcttgcct tgttgaaatc aacaggcgac tctctggaag aacgtctgca   118860
aggatttgcc tttaaagaag gcacaaacac cacactgatg tgcactacac gcactgttca   118920
gttgggcaac ggggtatata tggtcattgc agtgtgcccc aaattcagca acattaataa   118980
agatgatgct gacgctgtca acgacgtggt tgtcctcttc gtgggtgacg ctatggcaga   119040
tctgatgaat gcaggagaag cagcaaatga agactgaaaa cattcaccca gaaggattcc   119100
tgaaagtata ccgtgaacta ttgtatacca cagaggatag tgttctagag tacccagaat   119160
atcttttgct gtataagtat ctgcaggaag ctggtgaaaa tcttccaatt agcgcagaag   119220
gtggtccaaa ctgggtctac agtgcatgga gaaaggttga cattctccca gatcccggta   119280
aagatatggt agtttggcag cttatcaaca acatcgggat tccaatcttt gatgaagctg   119340
ttaaaatcta ttttgaactt gacgattaat atcaggagac cttaagatgg ctgaagtagt   119400
tgctcgtgca ggacagaaag tgcgttgtgt tgaagtgggt tttggtggca agggtgtca   119460
aaacttgact caaggtaagg aatacactgt tgtttctggc ggtggtgacg aaagtattgt   119520
gttcgatgac catattctgg atgttgaaaa ctttgaaata attgatgatg atggtgatcc   119580
gatcacctgc ctgctgaacg ggagttgggg tactttcgaa gtaattggct aacaaatatc   119640
tgttgtaatt tacagaagga gatgctaaaa tggtgtctcc tttatgttgt tcaaataaaa   119700
tcggagattc cataatggaa caaatgaacg atcaagcgtc ggttgcgatg aacgagcaag   119760
aacaacctca agaatttttc ttagggttaa gcaaagatca ggtgtctctc ctgttagtgc   119820
tctcttcttt catggggaga cttcaggagc tcacacaaca accagaggct gaacaattat   119880
ttcaggctct gcgcgaagaa gaaaaatatc gtcgtttaga ttatgcctta ggttgggtag   119940
ctcagcaacg agatatgcta atggcccttt ctgggacgac aagttttgca atgggcctgt   120000
tggctcaagt gcaggacaaa ttaattcaag cagggtttgc acacacagca aacaccaacg   120060
aagaacaagg agacaaataa tgggcgttat tcaacaattt gccaacccga tgaatccgcg   120120
tgaaactgtt ttactggctc acggcatgat taaacgtgtc agcatcaaac ctatcaaagg   120180
tgctgatcct acaacaggta ttaaaaccac tgtgtggcaa ggtaagaaaa tcgagtccag   120240
tcacaccatc tctttactga tttctgaact ggattcttct gataacctac ttcaaggtgg   120300
tgaagaagtt tggatcagca tgggtgataa attgctcaaa cctggtcatc aagattccgt   120360
ctctgttaaa attgatgaca agtgggaaac agtaacgcca ggatggatcg taaatatccc   120420
tttaaaggca aatgagcata acggtaagac ctactacaaa ggctcattgg ctaaaatggt   120480
taagctgggg gcaggagagg ctccagcagc tccacagcaa caaaaacagc aacaaggcac   120540
```

```
acaatcacaa ggccagaagc agaaacctca gcagaatgcc aatcaggacg ttttacgcat  120600
ctatggtgat gtgactcaga ttgttggtaa cgtggttact gtcaatgacc acaagatcgg  120660
cgaaggtgct atggttgtct ccgatgagca gcttaaagac ctggtggttg gcggtcgtgt  120720
tgcagctatt gttgacaaag acaccgggaa tattatcagc ggcttcaagg cctacccgcc  120780
taaagcagag aacggtacac aaggttctgg tggtaagcgt aaatcctctt acgacccat  120840
tggtgtagag acagggcaca gtatcaatgc gttgcagatc attctggatc gcgggtttaa  120900
gattgacagc cctttagatg tggctaaaac attgcacgtg gtcaccatcg agcttaagaa  120960
agagtacgct caagccacca accggactga agatgaagta ggtgccagtg ttggtaacgc  121020
ggtattgaac gcttgtcgcc gtattgacaa gaaaacgaaa gttgatgatt ttgcagtagc  121080
aattactgca gaggcaaaag atgtcttgac taatcttgct gaaccgttgt acgattggat  121140
caagaatggt gcgggggacta ctgagcatca agaacctcaa gctgccaaac aggaagccac  121200
tccacagcaa aacactgtag acgcccctcc tgtagatgat gacggagatg acccgatgga  121260
tcagaatccg gcacaataca cctttgatga tgacattcct ttttaacatc tagttaacat  121320
agccctgccc gaaagggtgg ggcattttg tataaggaga tctgaaaat gacattagaa  121380
gatatcattg ttaaacctga gaactatgac caatacaatc tatcaactca atctgtggac  121440
cttggatgcg ccactgtcag tgcgtggctg gttaacggaa aagagctgga taatgctta  121500
gaagctcaca tgtctattaa caagtttctg gatgaaaata ctcactggct tgagggtgca  121560
ggcgtatatg gctatgccag agttcaagct accaaaggag ggtgctgatg tttaagctta  121620
aatctgcatg gaacattgct gtaggcgatg agatccgcat tccgggtggg aagaccgtta  121680
tgaagatatc ccgtattgaa tacgaaggtg accgtgtatt ccatattttt gcagaagatg  121740
gtcgagaaat ttatatacag gcaggctcac acatctatat tcgtaaaggg gatgacaaat  121800
gacagagatc atcatttcaa ctgcagggta tgtattcctg acaatcattg cgctgatcat  121860
cttggtggtg gtgtatggat ttgttatcct gcctattctt gagacattta gtttgtgtcg  121920
gtgttggaga aaggcttacg gaccacagcc gtggagagac tggccccacc tgttacgcat  121980
agcgttctct tatgcctatg atcactccag tagtgcatgc ataaccgggt atcacgccca  122040
caactggaac tgggaagggc tggggagatg gagtgttata aaaactatac ctctacgcat  122100
gtacaagcct aaaaacaaag atagttgata cttgaaaatc cctggcacat caaacataag  122160
ggggatttct aaaatggatt tcctcctttt gatatttac ctagccggat attttaaaat  122220
tcctagaaaa tcagaaaatg gatcgaaaac taaaatggat ttttcaaga caggcacgat  122280
aagctgcgct gctcattcta tcattcgcac cgtactccaa atcaccgttc cagattttcc  122340
gcacacactc tcacccttct accagaactt tcccaactta ccttcagcct tttatgacaa  122400
taagttaatt attatcagta agttttgata catctctctc agtactcgat ctgtttttca  122460
tttcaaagat tggattttct gaaaattttt ctcgataaat ttttcggtac tcgatctgtt  122520
tttcgttttc tgaatcagat tttctggaaa tcgttccggc gctcgacctg aaattttgg  122580
ggacgaaatc gattttttcgt tttcagaaat ggatttttaa aatttctata tgggaatatt  122640
ttatgaggta ttatttttata tagaattgta acggtaggta attagcatgc taactaaatt  122700
tatgaaatgc gaaaagttct catttagaat tttgaatgat aatcattctc gtttgcagaa  122760
taacgggcac ccccggtgat tgtctcccgg cccctactgc cccggcttgt tattatagta  122820
tcacacagga caaagaaagc aagaagtttt tgcataaatt tttagacgat aatgataatc  122880
```

```
gttctcattt catgcagcgc ccatccccgg tggttgcctc ccccgtcacc ggtgcctgcc    122940
gtcctttcga tatgtatatt gtgccacctg gcggggccgc tgtcaacact tttcaaaaaa    123000
aattctaacc tgatgcgcta accgctgcaa cctggcgggg ccagcctggt gggcctatgc    123060
tataggatag gtaacaattg aagaggaggt acaaaaatga aggtaatag  gatcccctg     123120 gaaaatgtag ctattaataa cgctgaggct atcgccctgg tggaaaaggt tatggcggga    123180
gcgttggaac ataaagaaga gtacgaaaaa atgatggtca acctggcagg ggcggcggct    123240
ggagaattct acccaaaaaa taattttaac tagtggttga cagctcggac agttttgtt     123300 attcttatcc tcgcaaggtg aacaacacca cactaattaa cagagaggat aaaaaatcat    123360
gaacgcctac ggaattaaag tacgtcgcag cactcgccag gtggtcaccg atcaaatggt    123420
ttgccaggtg gatgtgacca tcaacaacgg gcaaggcctt tataaattcc gtcgcggtca    123480
gagctatacc cggcaacagc ttaatcgttg cgccctgaca aaaggccaga tcaaccactg    123540
gtttagtaaa aaaataagta ttgacatata ggccgacacc aaatacacta aaagcacaaa    123600
agacactgag aggataaaat catgaaaacc accacctta  attttgataa tgcggacttt    123660 tcttttctg  atgtcaagaa ctgccgccgt gatcgtggat tttacaaggc ctataatctg    123720
gtgggcctgg acgatgacaa taatttgcac gaagtagctg agatccggta ttatgccgcc    123780
gccagcggga acacttacta ctgcgttttt tggatacacg acaacaagaa caatgagtac    123840
ggctatactg gcggcaaggc gagcggtcac ggttatgata agccaacgc  agcacttgag    123900 agcgcattaa atgctatggg gatcactgcc gacggctgga tctacgaaga agagttttg     123960 gcggcacttg ctgaccgcct gggctataaa agcacattg  tgacatgtgc ccacgaataa    124020
aaatcattga cacgctgcaa aattcaagta aactaggcac aaaaggcggg aatgtctccc    124080
gccagaacaa aggaaaaaga tcatgaataa gaacgtacgc cgcatcatga acgagttggc    124140
aaacgatgaa aaaattattg acatgcattt gatcaacatt tgccgccgtt gtgtaacata    124200
taacaaccgc gccgcaaaag cgcgtgagat gaacgcaaaa ggcaccttaa agcccttcca    124260
ggtggtggta aaggccatta agatgtaac  taatacagca aaccaggtac aggggaacac    124320
caacgagagt accaatattg atccggctta catcatgaaa cggatccgga cctgtaagaa    124380
taaagagcag gtatataacg tcatagattg gttggattct atgggcgacg tggtgtacaa    124440
taggttttct gcagctattg agatccagct tgacaggttg gacgggaaag tactgaaaac    124500
ttattaagtt tatttttaga tggccttgac tccagggcca tcaataaagt aaactagtct    124560
caactaagcg aaaaggggg  ctttaagatg agcactacac gccaatacac aaaggtaact    124620
attatcgttt gcgttgtcgg ttacatcctg gcgcaaatgt taatgagtag cgccaacagt    124680
tttgcaaaat ttttcttaaa ttttaattg  acaagctaac ctaaatcggt atacttaaac    124740
acgtaaacgg gaaaacttcc caaaacacaa aaaggagaaa acaccatgac tactatgacc    124800
gccgcagaaa aagctatgca gatcgccgcg ctgaaaaaac agatcgcaga tcttgagaac    124860
aagatcgata actttgaaat cgacgaggac aagtacgacg aaaactatga tgaatggtta    124920
gacgagatcc acggcgaaat tatgatcggt aacatttctt ttcttccgtc gcgtatcctc    124980
aaggagttag atcctatcgc ttaccgctgc ggatttagcg actacatcga cagcctggat    125040
attgaggacg atgaagaata ccaggaattg cagacagagc tggaagaagt gaaagaggag    125100
ctttcagagc tggaagaaaa cgagtaaaat ttatttttag atggccttga ctccagggcc    125160
atcaataaag taaactttac actgttaaca ctgaactaat gaggagttaa acccatggc     125220 agcactaatc acaaaatatt atgcgcccac caacaccaaa agcgcccgta tcatggtaaa    125280
```

```
aggcttcgga cgtaaaaagg tctacacctg ggactattcc ctagacatgg aagacaacca    125340
caccaacgca atgaccgatt ttattaatga actaaataaa cagatcttga caaattataa    125400
agttaccgat gttgcttaca taggtgaagg cgggatctgt tttgtaggca ttgtgaaata    125460 gttattttt cggtggtcct ggttgcaggg ccatctataa agataattta ttaacaccat     125520
gaaaggagaa agtgcacatg atcagcggga ctagtttat tattggcgct attgctacgg     125580
ctttaattgt aaacaagatc caggataaaa aggaaagagg aagtaccgcc cttgcagaat    125640
atccattttg gacattcaac gataacgaag attatattat aaagtataaa aataaagaag    125700
gtgaccaagt aacaccgcga ccgatcccgg cttacaaaat gcaggaaaca ctataccgcc    125760
tggaggcggg gggcgcaaaa attgttgact tttggggata cgaccacaca gatcaggaag    125820
ttataaagcg ccgtatccgg gctattcagg ccaatattga ggttaacaag ggggaatat     125880 atgaaaatta atttcgagaa aattgtaaag cgccctcatg attccgaaga gctgccagaa    125940
cgccgacagc gcaacaataa actgaataag ccaaaaaggt ttgggaagat ctggcggaat    126000
cattatgatc gtaaattgcc cggcctactt ttggaacgtg aacgacaggc agaacgatac    126060
cgccataaag acaaataaca accaacgccc cgccattgtg cggggctttt tatttctatc    126120
ctacgaatag cgcccctggt tggccctgta agcgccaaaa aggcccccac ctatgcaatc    126180
gcccccttta acctgaaaac atcgctcagg gccgttttat agcgttaaaa atatcattga    126240
catcgtcaac aggttacaat ttatctttcg acgtgctgac cgacgaacaa aaagaaaaag    126300
ccattgaaat ggtccgcgaa agagaagaac gcagcgagga tgattttttc gcagaaaatg    126360
taattgaata ctatgaagaa tatgtctttc cagagtacgg ccttgaagat accgaagtac    126420
attggtccgg cttttggtgt caaggcgatg gcgcatcgat cagtgctgaa aatgtagact    126480
tagaaaaatt cttgcgtaaa gtcaaggccc tgaccaagtt ccgatcaatt cgtcacttgt    126540
tcggcacaat gcatgatggc gaactatccg ccagtattga acgcgacaag tacagccgtt    126600
acagccatga aaacactgta agcgggtaca ttgataccac atggctagat ctgaccgcta    126660
aacaagaaaa caaagtggaa gacctggaag agctgatcac cgagacggta cgggagctat    126720
cccgcaaggt ttacgtagac ctggaggagg cttatctaga gcagttcacc gcagaaaacc    126780
tgatcggcct tatcgcggcc aatgattgga ggtttgatgt ggatgaatat ggggaaatga    126840
gttttcataa ataaagtgtt gcaataacct aaaaacctgc tatattaaaa ctcaaggggc    126900
aagacgtttg ccccaacaca aaacatagag gataacatca tgaaaacac caccaaggct    126960 attgacaccg ttatgtttaa cctggtcaca ttccgtgaag atatgaaaga tcttccgcgt    127020
gaaacagtgt gcgaccatat cgaaaactat cgcaaactaa tcaaagagtt gcctttaaaa    127080
cgtgatcaat atgcggctaa cgccatgctt aatgccatga tcaaaaagat gatccagtgt    127140
gatttaaccc tggcctatga ttatgcaggc ggtcgttttg cagtatacaa tcagcccgtg    127200
cctggtatga gcaccaccga agaattgcac gcgctcaatc taaaacaaga cgtgtgggat    127260
agtatgcctc gcgtggtggt atgggtagaa agcggaaaga tttacggcga taattttaa    127320 tcaggtagca ggcggcatat ttgccgcctt attgttgata agaactgcaa aagaggtaca    127380
tagaatggaa tttattattt tggctgtgtt ggtcgcctta tttaacgcct ggatcgctgg    127440
caagatggga agatccgcct ttttatggtt tattatatct attttcctgg gggtggttgc    127500
aactattgta ttaattatcc ttgcaattgt tgacaagggg aataatagaa agggtaaagt    127560
attttcagac ctgtacgacg ctcaaacgtt tgtcaacgcc tattatagtg atctcccgat    127620
```

```
ctccctacgt tgcagccttg cgcaacaggt tttcgatgag gctaaaacca gagatcacgc   127680
ccatgagatt tgtttaactg aggcggatcg cttatttgag aggagtagaa atatgtggg    127740 ccagccgttt aaataatacc acgttaatta atccatttag tgaagatttg aagccagccg   127800
cctggcggga tggattcaat aacgaaggat ttacttttag gcctgatctt gaggaatttt   127860
ataacaatgg atcgaacaac gacagagata attttttcttg cggtgtgtgt cgtgatcgga  127920 ctactgggg ccattgcaaa ccacgtaacc gctaacagga ggaaaggggg agacgatgac    127980
acccaaggat aagccccgca ccgataaggc gcgccgtgtt atggtatggc tggagatcct   128040
cgcccttgaa atattgttag gcgtaggggat gtattttatc gctgtacgta cctgataacg  128100
gcccccgatc cctgggggcc taactttttt caaaaatttt ttcttccgag gtgttgcaat   128160
ccggtcctga atatggataa taacaatcaa cggggagaca ctccccacca cacagacaaa   128220
gttccaaaag gagaaacaaa atgagcaaca atatccgcgt tattaacttc aaaaagaag    128280 aaaaaattgc tgtgctggtt gatggtcaag aaatattcaa ggggtattat gaagatcatc   128340
aggcggcgat cagtattacc cgcgtgattg gttaccataa ttttttaccct caaggcgctg  128400 aggcagcagt aaaacgaatt aaagacattg taggcctgta agtttatttt ttagatggcc   128460
ttgactccag ggccatcaaa taaagtaaat ttaaaccctg ctaaataat cagcgcaaaa    128520 aggagcaatg atcatgttta tacccgccaa taatctttat ttcttttgatg gtcagatcgt  128580 agacggcgtg gaagttgaga tcactggatg tcaaggcggc caggtaatga tcttccgcaa  128640
tagtgccttt aacgatcaat ttattacaat gactgtggaa gttaaaaagc tggatgataa   128700
gaagacactt attgactatt ccgtgaaaga tcatccagac taccacatga tctatggtga   128760
tttgtgcatt gttgaccgtg acaaggtggg cggcattgtg atcgctattg tgaacgatgt   128820
tttctccaga taattccggc aaatgatgca aaataaggcc cgtggcaggg cctgcagcga   128880
cataatcaca taaagtctat gcggttgcat ggcctttatt attttagcgc tacagcgacc   128940
ccccagggcg tttaaaaaat ttttaaaaag tgcttgcatc aagccctaca atatggataa   129000
taggacgtat caggggggcgg ccccccaatca ttaaccggat agagaggagt taaaatcatg   129060
gctattgtta cctttggcga tgtagtagaa atggaagcaa atacttaaa agcgggcatg   129120 catatcctac gcaacgatct tgagttagtc ctgacaatgg tcgactataa tcccggtcag   129180
gattatccaa gcattgacta cttttttccag tatgttgatg aagaattaaa agaggatgag  129240
gcttatcagg gtgaattttg taacttcttt tgccctgatg aggttgtaaa agttatctat   129300
caacctggcg tacctttccc gctgcacgcc atcaataaat aagcctggcg gggccgaaaa   129360
aggcccctcc tgaaactatg aaaaaataaa gataggtaaa aacatcatga aacgtcttga   129420
tcagctcaaa ctagttcagt acatggccta caaagttctt gaagtccaaa aaggtagcaa   129480
aaaagaggtt tgcgagaaag catataagat ctttacccgt aaaaagatg attggatgtt    129540 acgccagact aaaaaggctg atatcctggg gtacctggaa gaagagatcc ggcttgaaga   129600
gcaagaagag atccgccgca gtgaggcaga ttatcaggca gcttgggaaa gctggatgag   129660
taacaaataa tacaacatta tcaaggggcc taggccccctt tcttttttgtc tgctctttc   129720 ctaccataaa cggccctacc tgacaagtgg aataattgac gagccatcaa tcccgcacac   129780
tgtacaaata tacatgtaaa atatctattg tataaccttt cattgtgtgg tagcggtgct   129840 attttaccc gttttctctc ccaaaattgc acgtaatgca gctattgcac aaaatttaac   129900
ctgatgcaca tcttcagcat actgtcaaca attaaaaacc cttataagtc atacacttac   129960
acaaaccaaa aagcgtgtcc tacgtgaaaa atcgggtgta actatagccg acagatctca   130020
```

```
gaatccacgt acgatcacca ttctatagcc tgcaaagtat ctattccaac cgcagaataa  130080
cggaatagtc aatacttgta tacaataatt attcgtataa actgcataac ataaattttc  130140
tcatgtgtca acattcttcg taaacagtcc gaaattgtca cgataggtta ctataatcag  130200
agaaatcttt agtcgtctaa tgtttactgc acataactat actgactgga atcattagat  130260
gactaagaga aagataagaa atagttaaca atgtaattgt tttacctgta acaataaggc  130320
aactatgcaa acgaatgtca tggcgcgacg gagtcgcgac ataatataaa agcagtaaca  130380
atcacccccg tgatagtttg tctgcaatct attaatcaga tcatagttgc cttgtattca  130440
gttaatcatg acataataag caaggcaact atagatctgc taatagttgc cctgctttta  130500
tattatgtca tatattatta acctgttaat tgtcagcttg ttggctgtta gcttgtcaat  130560
tgttatcttg ttaattgttt tcatgcaaac gaatgtcatg gcttatcatc tatgcgtaaa  130620
ctgtcagggt gtagactatt caggtgtaaa ctatccaggc gtaaacagtc tatgcgagaa  130680
caatctgcac gtgaacaatg aaacatgaaa taataacagt cgttattgtg tcgaaagtgt  130740
ataaggtgtc acattgtgtc atattgtgtc cggtgtataa ggtgtca              130787
```